(12) United States Patent
Choi et al.

(10) Patent No.: US 11,965,014 B2
(45) Date of Patent: Apr. 23, 2024

(54) IMMUNE SYNAPSE-STABILIZING CHIMERIC ANTIGEN RECEPTOR (CAR) T CELL

(71) Applicant: TICAROS CO., LTD., Seoul (KR)

(72) Inventors: Kyungho Choi, Seoul (KR); Eun-Young Choi, Seoul (KR); Giri Nam, Seoul (KR); Hyung-Bae Park, Seoul (KR); Ji-Eun Lee, Gyeonggi-do (KR); Hye-Ran Yeon, Gyeonggi-do (KR)

(73) Assignee: TICAROS CO., LTD., Seoul (KR)

( * ) Notice: Subject to any disclaimer, the term of this patent is extended or adjusted under 35 U.S.C. 154(b) by 0 days.

(21) Appl. No.: 17/638,923

(22) PCT Filed: Jul. 28, 2021

(86) PCT No.: PCT/KR2021/009828
§ 371 (c)(1),
(2) Date: Feb. 28, 2022

(87) PCT Pub. No.: WO2022/025638
PCT Pub. Date: Feb. 3, 2022

(65) Prior Publication Data
US 2023/0118625 A1    Apr. 20, 2023

(30) Foreign Application Priority Data

Jul. 29, 2020  (KR) .................. 10-2020-0094624

(51) Int. Cl.
*C07K 14/705* (2006.01)
*A61K 35/17* (2015.01)
(Continued)

(52) U.S. Cl.
CPC ........ *C07K 14/70596* (2013.01); *A61K 35/17* (2013.01); *A61P 35/00* (2018.01);
(Continued)

(58) Field of Classification Search
None
See application file for complete search history.

(56) References Cited

U.S. PATENT DOCUMENTS 10,766,943 B2   9/2020   Bachmann et al.

FOREIGN PATENT DOCUMENTS

| JP | 2017-530724 A | 10/2017 | |
| WO | WO-2018071583 A2 * | 4/2018 | ............. A61K 35/17 |
| WO | 2019/136419 A2 | 7/2019 | |

OTHER PUBLICATIONS

Notice of Allowance issued in corresponding Korean Patent Application No. 10-2020-0094624 dated May 4, 2021.
(Continued)

*Primary Examiner* — Zachary S Skelding
(74) *Attorney, Agent, or Firm* — Morgan, Lewis & Bockius LLP

(57) ABSTRACT

The present invention relates to a novel chimeric antigen receptor comprising a CD99 region which participates in immune synapse stabilization as a backbone of the chimeric antigen receptor, an immune cell comprising the same, and the uses thereof. CD99-based CAR-T cells are capable of forming very stable immune synapses with tumor cells compared to conventional backbone-based CAR-T cells and can exhibit improved tumor therapeutic efficiency, so they can be useful for immune cell therapy for the treatment of cancer.

19 Claims, 8 Drawing Sheets
Specification includes a Sequence Listing.

(51) Int. Cl.
- *A61P 35/00* (2006.01)
- *C07K 14/725* (2006.01)
- *C07K 16/28* (2006.01)
- *C12N 5/0783* (2010.01)
- *C12N 15/86* (2006.01)
- *A61K 38/00* (2006.01)
- *A61K 39/00* (2006.01)

(52) U.S. Cl.
 CPC .... *C07K 14/7051* (2013.01); *C07K 14/70517* (2013.01); *C07K 16/2803* (2013.01); *C12N 5/0636* (2013.01); *C12N 15/86* (2013.01); A61K 38/00 (2013.01); A61K 2039/505 (2013.01); A61K 2039/5154 (2013.01); A61K 2039/5156 (2013.01); A61K 2039/5158 (2013.01); C07K 2317/569 (2013.01); C07K 2317/622 (2013.01); C07K 2317/76 (2013.01); C07K 2319/02 (2013.01); C07K 2319/03 (2013.01); C07K 2319/33 (2013.01); C12N 2740/10043 (2013.01)

(56) References Cited

OTHER PUBLICATIONS

Office Action issued in corresponding Korean Patent Application No. 10-2020-0094624 dated Sep. 24, 2020.
Gattinoni et al., "Adoptive immunotherapy for cancer: building on success," Nature Reviews Immunology, 6 (5): 383-393 (2006).
Mardiana et al., "Supercharging adoptive T cell therapy to overcome solid tumor-induced immunosuppression," Science Translational Medicine, 11: eaaw2293 (2019).
Van der Stegen et al., "The pharmacology of second-generation chimeric antigen receptors," Nature Reviews Drug Discovery, 14 (7): 499-509 (2015).
Pata et al., "Association of CD99 short and long forms with MHC class I, MHC class II and tetraspanin CD81 and recruitment into immunological synapses," CMC Research Notes, 4:293 (2011).
International Search Report issued in corresponding International Patent Application No. PCT/KR2021/009828 dated Nov. 9, 2021.

\* cited by examiner

A

B

SEQUENCE LISTING

<160> NUMBER OF SEQ ID NOS: 44

<210> SEQ ID NO 1
<211> LENGTH: 185
<212> TYPE: PRT
<213> ORGANISM: Artificial Sequence
<220> FEATURE:
<223> OTHER INFORMATION: CD99

<400> SEQUENCE: 1

```
Met Ala Arg Gly Ala Ala Leu Ala Leu Leu Leu Phe Gly Leu Leu Gly
1               5                   10                  15

Val Leu Val Ala Ala Pro Asp Gly Gly Phe Asp Leu Ser Asp Ala Leu
            20                  25                  30

Pro Asp Asn Glu Asn Lys Lys Pro Thr Ala Ile Pro Lys Lys Pro Ser
        35                  40                  45

Ala Gly Asp Asp Phe Asp Leu Gly Asp Ala Val Val Asp Gly Glu Asn
    50                  55                  60

Asp Asp Pro Arg Pro Pro Asn Pro Pro Lys Pro Met Pro Asn Pro Asn
65                  70                  75                  80

Pro Asn His Pro Ser Ser Ser Gly Ser Phe Ser Asp Ala Asp Leu Ala
                85                  90                  95

Asp Gly Val Ser Gly Gly Glu Gly Lys Gly Gly Ser Asp Gly Gly Gly
            100                 105                 110

Ser His Arg Lys Glu Gly Glu Glu Ala Asp Ala Pro Gly Val Ile Pro
        115                 120                 125

Gly Ile Val Gly Ala Val Val Val Ala Val Ala Gly Ala Ile Ser Ser
    130                 135                 140

Phe Ile Ala Tyr Gln Lys Lys Lys Leu Cys Phe Lys Glu Asn Ala Glu
145                 150                 155                 160

Gln Gly Glu Val Asp Met Glu Ser His Arg Asn Ala Asn Ala Glu Pro
                165                 170                 175

Ala Val Gln Arg Thr Leu Leu Glu Lys
            180                 185
```

<210> SEQ ID NO 2
<211> LENGTH: 558
<212> TYPE: DNA
<213> ORGANISM: Artificial Sequence
<220> FEATURE:
<223> OTHER INFORMATION: CD99

<400> SEQUENCE: 2

```
atggcccgcg gggctgcgct ggcgctgctg ctcttcggcc tgctgggtgt tctggtcgcc      60
gccccggatg gtggtttcga tttatccgat gcccttcctg acaatgaaaa caagaaaccc     120
actgcaatcc ccaagaaacc cagtgctggg gatgactttg acttaggaga tgctgttgtt     180
gatggagaaa atgacgaccc acgaccaccg aacccaccca aaccgatgcc aaatccaaac     240
cccaaccacc ctagttcctc cggtagcttt tcagatgctg accttgcgga tggcgtttca     300
ggtggagaag gaaaaggagg cagtgatggt ggaggcagcc acaggaaaga aggggaagag     360
gccgacgccc caggcgtgat ccccgggatt gtggggctg tcgtggtcgc cgtggctgga     420
```

```
gccatctcta gcttcattgc ttaccagaaa aagaagctat gcttcaaaga aaatgcagaa    480
caaggggagg tggacatgga gagccaccgg aatgccaacg cagagccagc tgttcagcgt    540 actctttag agaaatag                                                    558
```

<210> SEQ ID NO 3
<211> LENGTH: 25
<212> TYPE: PRT
<213> ORGANISM: Artificial Sequence
<220> FEATURE:
<223> OTHER INFORMATION: CD99 TM

<400> SEQUENCE: 3

```
Ala Pro Gly Val Ile Pro Gly Ile Val Gly Ala Val Val Val Ala Val
1               5                   10                  15

Ala Gly Ala Ile Ser Ser Phe Ile Ala
            20                  25
```

<210> SEQ ID NO 4
<211> LENGTH: 75
<212> TYPE: DNA
<213> ORGANISM: Artificial Sequence
<220> FEATURE:
<223> OTHER INFORMATION: CD99 TM

<400> SEQUENCE: 4

```
gccccaggcg tgatccccgg gattgtgggg gctgtcgtgg tcgccgtggc tggagccatc    60
tctagcttca ttgct                                                      75
```

<210> SEQ ID NO 5
<211> LENGTH: 100
<212> TYPE: PRT
<213> ORGANISM: Artificial Sequence
<220> FEATURE:
<223> OTHER INFORMATION: CD99 EC

<400> SEQUENCE: 5

```
Asp Gly Gly Phe Asp Leu Ser Asp Ala Leu Pro Asp Asn Glu Asn Lys
1               5                   10                  15

Lys Pro Thr Ala Ile Pro Lys Lys Pro Ser Ala Gly Asp Asp Phe Asp
            20                  25                  30

Leu Gly Asp Ala Val Val Asp Gly Glu Asn Asp Asp Pro Arg Pro Pro
        35                  40                  45

Asn Pro Pro Lys Pro Met Pro Asn Pro Asn Pro Asn His Pro Ser Ser
    50                  55                  60

Ser Gly Ser Phe Ser Asp Ala Asp Leu Ala Asp Gly Val Ser Gly Gly
65                  70                  75                  80

Glu Gly Lys Gly Gly Ser Asp Gly Gly Gly Ser His Arg Lys Glu Gly
                85                  90                  95

Glu Glu Ala Asp
            100
```

<210> SEQ ID NO 6
<211> LENGTH: 300
<212> TYPE: DNA
<213> ORGANISM: Artificial Sequence
<220> FEATURE:
<223> OTHER INFORMATION: CD99 EC

<400> SEQUENCE: 6

```
gatggtggtt tcgatttatc cgatgccctt cctgacaatg aaaacaagaa acccactgca    60
```

```
atccccaaga aacccagtgc tggggatgac tttgacttag agatgctgt tgttgatgga    120 gaaaatgacg acccacgacc accgaaccca cccaaaccga tgccaaatcc aaaccccaac    180
caccctagtt cctccggtag cttttcagat gctgaccttg cggatggcgt ttcaggtgga    240
gaaggaaaag gaggcagtga tggtggaggc agccacagga agaagggga agaggccgac     300
```

<210> SEQ ID NO 7
<211> LENGTH: 58
<212> TYPE: PRT
<213> ORGANISM: Artificial Sequence
<220> FEATURE:
<223> OTHER INFORMATION: CD99 58EC

<400> SEQUENCE: 7

```
Asp Asp Pro Arg Pro Pro Asn Pro Pro Lys Pro Met Pro Asn Pro Asn
1               5                   10                  15

Pro Asn His Pro Ser Ser Ser Gly Ser Phe Ser Asp Ala Asp Leu Ala
            20                  25                  30

Asp Gly Val Ser Gly Gly Glu Gly Lys Gly Gly Ser Asp Gly Gly
        35                  40                  45

Ser His Arg Lys Glu Gly Glu Glu Ala Asp
    50                  55
```

<210> SEQ ID NO 8
<211> LENGTH: 174
<212> TYPE: DNA
<213> ORGANISM: Artificial Sequence
<220> FEATURE:
<223> OTHER INFORMATION: CD99 58EC

<400> SEQUENCE: 8

```
gacgacccac gaccaccgaa cccacccaaa ccgatgccaa atccaaaccc caaccaccct     60
agttcctccg gtagcttttc agatgctgac cttgcggatg gcgtttcagg tggagaagga    120
aaaggaggca gtgatggtgg aggcagccac aggaaagaag gggaagaggc cgac          174
```

<210> SEQ ID NO 9
<211> LENGTH: 45
<212> TYPE: PRT
<213> ORGANISM: Artificial Sequence
<220> FEATURE:
<223> OTHER INFORMATION: CD99 45EC

<400> SEQUENCE: 9

```
Asn Pro Asn Pro Asn His Pro Ser Ser Ser Gly Ser Phe Ser Asp Ala
1               5                   10                  15

Asp Leu Ala Asp Gly Val Ser Gly Gly Glu Gly Lys Gly Gly Ser Asp
            20                  25                  30

Gly Gly Gly Ser His Arg Lys Glu Gly Glu Glu Ala Asp
        35                  40                  45
```

<210> SEQ ID NO 10
<211> LENGTH: 135
<212> TYPE: DNA
<213> ORGANISM: Artificial Sequence
<220> FEATURE:
<223> OTHER INFORMATION: CD99 45EC

<400> SEQUENCE: 10

```
aatccaaacc ccaaccaccc tagttcctcc ggtagctttt cagatgctga ccttgcggat     60
ggcgtttcag gtggagaagg aaaaggaggc agtgatggtg gaggcagcca caggaaagaa    120
```
ggggaagagg ccgac                                                          135

<210> SEQ ID NO 11
<211> LENGTH: 35
<212> TYPE: PRT
<213> ORGANISM: Artificial Sequence
<220> FEATURE:
<223> OTHER INFORMATION: CD99 35EC

<400> SEQUENCE: 11

```
Gly Ser Phe Ser Asp Ala Asp Leu Ala Asp Gly Val Ser Gly Gly Glu
1               5                   10                  15

Gly Lys Gly Gly Ser Asp Gly Gly Gly Ser His Arg Lys Glu Gly Glu
            20                  25                  30

Glu Ala Asp
        35
```

<210> SEQ ID NO 12
<211> LENGTH: 105
<212> TYPE: DNA
<213> ORGANISM: Artificial Sequence
<220> FEATURE:
<223> OTHER INFORMATION: CD99 35EC

<400> SEQUENCE: 12
ggtagctttt cagatgctga ccttgcggat ggcgtttcag gtggagaagg aaaaggaggc    60
agtgatggtg gaggcagcca caggaaagaa ggggaagagg ccgac                   105

<210> SEQ ID NO 13
<211> LENGTH: 11
<212> TYPE: PRT
<213> ORGANISM: Artificial Sequence
<220> FEATURE:
<223> OTHER INFORMATION: CD99 jTM

<400> SEQUENCE: 13

```
Tyr Gln Lys Lys Lys Leu Cys Phe Lys Glu Asn
1               5                   10
```

<210> SEQ ID NO 14
<211> LENGTH: 33
<212> TYPE: DNA
<213> ORGANISM: Artificial Sequence
<220> FEATURE:
<223> OTHER INFORMATION: CD99 jTM

<400> SEQUENCE: 14
taccagaaaa agaagctatg cttcaaagaa aat                                 33

<210> SEQ ID NO 15
<211> LENGTH: 41
<212> TYPE: PRT
<213> ORGANISM: Artificial Sequence
<220> FEATURE:
<223> OTHER INFORMATION: CD8 EC

<400> SEQUENCE: 15

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp
        35                  40
```

<210> SEQ ID NO 16
<211> LENGTH: 123
<212> TYPE: DNA
<213> ORGANISM: Artificial Sequence
<220> FEATURE:
<223> OTHER INFORMATION: CD8 EC

<400> SEQUENCE: 16

```
accacgacgc cagcgccgcg accaccaaca ccggcgccca ccatcgcgtc gcagcccctg      60
tccctgcgcc cagaggcgtg ccggccagcg gcggggggcg cagtgcacac gagggggctg     120
gac                                                                   123
```

<210> SEQ ID NO 17
<211> LENGTH: 112
<212> TYPE: PRT
<213> ORGANISM: Artificial Sequence
<220> FEATURE:
<223> OTHER INFORMATION: CD3 zeta intracellular signaling domain(wild
      type)

<400> SEQUENCE: 17

```
Arg Val Lys Phe Ser Arg Ser Ala Asp Ala Pro Ala Tyr Gln Gln Gly
1               5                  10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 18
<211> LENGTH: 336
<212> TYPE: DNA
<213> ORGANISM: Artificial Sequence
<220> FEATURE:
<223> OTHER INFORMATION: CD3 zeta intracellular signaling domain(wild
      type)

<400> SEQUENCE: 18

```
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga agataagat ggcggaggcc tacagtgaga ttgggatgaa aggcgagcgc      240
cggaggggca aggggcacga tggcctttac cagggtctca gtacagccac caaggacacc     300
tacgacgccc ttcacatgca ggccctgccc cctcgc                               336
```

<210> SEQ ID NO 19
<211> LENGTH: 112
<212> TYPE: PRT
<213> ORGANISM: Artificial Sequence
<220> FEATURE:
<223> OTHER INFORMATION: CD3 zeta intracellular signaling domain(mutant)

<400> SEQUENCE: 19

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 20
<211> LENGTH: 336
<212> TYPE: DNA
<213> ORGANISM: Artificial Sequence
<220> FEATURE:
<223> OTHER INFORMATION: CD3 zeta intracellular signaling domain(mutant)

<400> SEQUENCE: 20
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagat ggcggaggcc tacagtgaga ttgggatgaa aggcgagcgc    240 cggagggca aggggcacga tggcctttac cagggtctca gtacagccac caaggacacc   300
tacgacgccc ttcacatgca ggccctgccc cctcgc                             336

<210> SEQ ID NO 21
<211> LENGTH: 42
<212> TYPE: PRT
<213> ORGANISM: Artificial Sequence
<220> FEATURE:
<223> OTHER INFORMATION: 4-1BB co-stimulatory

<400> SEQUENCE: 21

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 22
<211> LENGTH: 126
<212> TYPE: DNA
<213> ORGANISM: Artificial Sequence
<220> FEATURE:
<223> OTHER INFORMATION: 4-1BB co-stimulatory domain

<400> SEQUENCE: 22
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 23
<211> LENGTH: 242
<212> TYPE: PRT
<213> ORGANISM: Artificial Sequence
<220> FEATURE:
<223> OTHER INFORMATION: alpha CD19 scFv

<400> SEQUENCE: 23

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 24
<211> LENGTH: 726
<212> TYPE: DNA
<213> ORGANISM: Artificial Sequence
<220> FEATURE:
<223> OTHER INFORMATION: alpha CD19 scFv

<400> SEQUENCE: 24
gacatccaga tgacacagac tacatcctcc ctgtctgcct ctctgggaga cagagtcacc        60
atcagttgca gggcaagtca ggacattagt aaatatttaa attggtatca gcagaaacca       120
gatggaactg ttaaactcct gatctaccat acatcaagat tacactcagg agtcccatca       180
aggttcagtg gcagtgggtc tggaacagat tattctctca ccattagcaa cctggagcaa       240
gaagatattg ccacttactt ttgccaacag ggtaatacgc ttccgtacac gttcggaggg       300
gggaccaagc tggagatcac aggtggcggt ggctcgggcg gtggtgggtc gggtggcggc       360

```
ggatctgagg tgaaactgca ggagtcagga cctggcctgg tggcgccctc acagagcctg    420
tccgtcacat gcactgtctc aggggtctca ttacccgact atggtgtaag ctggattcgc    480
cagcctccac gaaagggtct ggagtggctg ggagtaatat ggggtagtga aaccacatac    540
tataattcag ctctcaaatc cagactgacc atcatcaagg acaactccaa gagccaagtt    600
ttcttaaaaa tgaacagtct gcaaactgat gacacagcca tttactactg tgccaaacat    660
tattactacg gtggtagcta tgctatggac tactggggcc aaggaacctc agtcaccgtc    720
tcctca                                                                726
```

<210> SEQ ID NO 25
<211> LENGTH: 21
<212> TYPE: PRT
<213> ORGANISM: Artificial Sequence
<220> FEATURE:
<223> OTHER INFORMATION: hCD8L

<400> SEQUENCE: 25

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 26
<211> LENGTH: 63
<212> TYPE: DNA
<213> ORGANISM: Artificial Sequence
<220> FEATURE:
<223> OTHER INFORMATION: hCD8L

<400> SEQUENCE: 26

```
atggccttac cagtgaccgc cttgctcctg ccgctggcct tgctgctcca cgccgccagg    60
ccg                                                                   63
```

<210> SEQ ID NO 27
<211> LENGTH: 511
<212> TYPE: PRT
<213> ORGANISM: Artificial Sequence
<220> FEATURE:
<223> OTHER INFORMATION: F58BBz

<400> SEQUENCE: 27

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125
```

```
Gly Gly Gly Ser Gly Gly Gly Ser Gly Gly Gly Ser Glu
130             135             140
Val Lys Leu Gln Glu Ser Gly Pro Gly Leu Val Ala Pro Ser Gln Ser
145                 150                 155                 160
Leu Ser Val Thr Cys Thr Val Ser Gly Val Ser Leu Pro Asp Tyr Gly
                165                 170                 175
Val Ser Trp Ile Arg Gln Pro Pro Arg Lys Gly Leu Glu Trp Leu Gly
            180                 185                 190
Val Ile Trp Gly Ser Glu Thr Thr Tyr Tyr Asn Ser Ala Leu Lys Ser
        195                 200                 205
Arg Leu Thr Ile Ile Lys Asp Asn Ser Lys Ser Gln Val Phe Leu Lys
210                 215                 220
Met Asn Ser Leu Gln Thr Asp Asp Thr Ala Ile Tyr Tyr Cys Ala Lys
225                 230                 235                 240
His Tyr Tyr Tyr Gly Gly Ser Tyr Ala Met Asp Tyr Trp Gly Gln Gly
                245                 250                 255
Thr Ser Val Thr Val Ser Ser Asp Asp Pro Arg Pro Pro Asn Pro Pro
            260                 265                 270
Lys Pro Met Pro Asn Pro Asn Pro Asn His Pro Ser Ser Ser Gly Ser
        275                 280                 285
Phe Ser Asp Ala Asp Leu Ala Asp Gly Val Ser Gly Gly Glu Gly Lys
290                 295                 300
Gly Gly Ser Asp Gly Gly Ser His Arg Lys Glu Gly Glu Glu Ala
305                 310                 315                 320
Asp Ala Pro Gly Val Ile Pro Gly Ile Val Gly Ala Val Val Val Ala
                325                 330                 335
Val Ala Gly Ala Ile Ser Ser Phe Ile Ala Tyr Gln Lys Lys Lys Leu
            340                 345                 350
Cys Phe Lys Glu Asn Lys Arg Gly Arg Lys Lys Leu Leu Tyr Ile Phe
        355                 360                 365
Lys Gln Pro Phe Met Arg Pro Val Gln Thr Thr Gln Glu Glu Asp Gly
370                 375                 380
Cys Ser Cys Arg Phe Pro Glu Glu Glu Glu Gly Gly Cys Glu Leu Arg
385                 390                 395                 400
Val Lys Phe Ser Arg Ser Ala Asp Ala Pro Ala Tyr Lys Gln Gly Gln
                405                 410                 415
Asn Gln Leu Tyr Asn Glu Leu Asn Leu Gly Arg Arg Glu Glu Tyr Asp
            420                 425                 430
Val Leu Asp Lys Arg Arg Gly Arg Asp Pro Glu Met Gly Gly Lys Pro
        435                 440                 445
Arg Arg Lys Asn Pro Gln Glu Gly Leu Tyr Asn Glu Leu Gln Lys Asp
450                 455                 460
Lys Met Ala Glu Ala Tyr Ser Glu Ile Gly Met Lys Gly Glu Arg Arg
465                 470                 475                 480
Arg Gly Lys Gly His Asp Gly Leu Tyr Gln Gly Leu Ser Thr Ala Thr
                485                 490                 495
Lys Asp Thr Tyr Asp Ala Leu His Met Gln Ala Leu Pro Pro Arg
            500                 505                 510
```

<210> SEQ ID NO 28
<211> LENGTH: 1536
<212> TYPE: DNA
<213> ORGANISM: Artificial Sequence
<220> FEATURE:
<223> OTHER INFORMATION: F58BBz

<400> SEQUENCE: 28

```
atggccttac cagtgaccgc cttgctcctg ccgctggcct tgctgctcca cgccgccagg      60
ccggacatcc agatgacaca gactacatcc tccctgtctg cctctctggg agacagagtc     120
accatcagtt gcagggcaag tcaggacatt agtaaatatt taaattggta tcagcagaaa     180
ccagatggaa ctgttaaact cctgatctac catacatcaa gattacactc aggagtccca     240
tcaaggttca gtggcagtgg gtctggaaca gattattctc tcaccattag caacctggag     300
caagaagata ttgccactta cttttgccaa cagggtaata cgcttccgta cacgttcgga     360
ggggggacca agctggagat cacaggtggc ggtggctcgg gcggtggtgg gtcgggtggc     420
ggcggatctg aggtgaaact gcaggagtca ggacctggcc tggtggcgcc ctcacagagc     480
ctgtccgtca catgcactgt ctcaggggtc tcattacccg actatggtgt aagctggatt     540
cgccagcctc cacgaaaggg tctggagtgg ctgggagtaa tatggggtag tgaaaccaca     600
tactataatt cagctctcaa atccagactg accatcatca aggacaactc caagagccaa     660
gttttcttaa aaatgaacag tctgcaaact gatgacacag ccatttacta ctgtgccaaa     720
cattattact acggtggtag ctatgctatg gactactggg gccaaggaac ctcagtcacc     780
gtctcctcag acgacccacg accaccgaac ccacccaaac cgatgccaaa tccaaacccc     840
aaccacccta gttcctccgg tagcttttca gatgctgacc ttgcggatgg cgtttcaggt     900
ggagaaggaa aggaggcag tgatggtgga ggcagccaca ggaaagaagg ggaagaggcc     960
gacgccccag gcgtgatccc cgggattgtg gggctgtcg tggtcgccgt ggctggagcc    1020
atctctagct tcattgctta ccagaaaaag aagctatgct caaagaaaa taaacggggc    1080
agaaagaaac tcctgtatat attcaaacaa ccatttatga gaccagtaca aactactcaa    1140
gaggaagatg gctgtagctg ccgatttcca gaagaagaag aaggaggatg tgaactgaga    1200
gtgaagttca gcaggagcgc agacgccccc gcgtacaagc agggccagaa ccagctctat    1260
aacgagctca atctaggacg aagagaggag tacgatgttt tggacaagag acgtggccgg    1320
gaccctgaga tggggggaaa gccgagaagg aagaaccctc aggaaggcct gtacaatgaa    1380
ctgcagaaag ataagatggc ggaggcctac agtgagattg ggatgaaagg cgagcgccgg    1440
aggggcaagg ggcacgatgg cctttaccag ggtctcagta cagccaccaa ggacacctac    1500
gacgccttc acatgcaggc cctgccccct cgctaa                              1536
```

<210> SEQ ID NO 29
<211> LENGTH: 498
<212> TYPE: PRT
<213> ORGANISM: Artificial Sequence
<220> FEATURE:
<223> OTHER INFORMATION: F45BBz

<400> SEQUENCE: 29

```
Met Ala Leu Pro Val Thr Ala Leu Leu Leu Pro Leu Ala Leu Leu Leu
1               5                  10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80
```

-continued

```
Ser Arg Phe Ser Gly Ser Gly Ser Gly Thr Asp Tyr Ser Leu Thr Ile
                85              90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
            115                 120                 125

Gly Gly Gly Gly Ser Gly Gly Gly Ser Gly Gly Gly Gly Ser Glu
130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
                180                 185                 190

Val Ile Trp Gly Ser Glu Thr Thr Tyr Tyr Asn Ser Ala Leu Lys Ser
                195                 200                 205

Arg Leu Thr Ile Ile Lys Asp Asn Ser Lys Ser Gln Val Phe Leu Lys
    210                 215                 220

Met Asn Ser Leu Gln Thr Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Asn Pro Asn Pro Asn His Pro Ser Ser
                260                 265                 270

Ser Gly Ser Phe Ser Asp Ala Asp Leu Ala Asp Gly Val Ser Gly Gly
            275                 280                 285

Glu Gly Lys Gly Gly Ser Asp Gly Gly Gly Ser His Arg Lys Glu Gly
290                 295                 300

Glu Glu Ala Asp Ala Pro Gly Val Ile Pro Gly Ile Val Gly Ala Val
305                 310                 315                 320

Val Val Ala Val Ala Gly Ala Ile Ser Ser Phe Ile Ala Tyr Gln Lys
                325                 330                 335

Lys Lys Leu Cys Phe Lys Glu Asn Lys Arg Gly Arg Lys Lys Leu Leu
                340                 345                 350

Tyr Ile Phe Lys Gln Pro Phe Met Arg Pro Val Gln Thr Thr Gln Glu
                355                 360                 365

Glu Asp Gly Cys Ser Cys Arg Phe Pro Glu Glu Glu Glu Gly Gly Cys
            370                 375                 380

Glu Leu Arg Val Lys Phe Ser Arg Ser Ala Asp Ala Pro Ala Tyr Lys
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
            420                 425                 430

Gly Lys Pro Arg Arg Lys Asn Pro Gln Glu Gly Leu Tyr Asn Glu Leu
            435                 440                 445

Gln Lys Asp Lys Met Ala Glu Ala Tyr Ser Glu Ile Gly Met Lys Gly
    450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495
```

Pro Arg

<210> SEQ ID NO 30
<211> LENGTH: 1497
<212> TYPE: DNA
<213> ORGANISM: Artificial Sequence
<220> FEATURE:
<223> OTHER INFORMATION: F45BBz

<400> SEQUENCE: 30

```
atggccttac cagtgaccgc cttgctcctg ccgctggcct tgctgctcca cgccgccagg      60
ccggacatcc agatgacaca gactacatcc tccctgtctg cctctctggg agacagagtc     120
accatcagtt gcagggcaag tcaggacatt agtaaatatt taaattggta tcagcagaaa     180
ccagatggaa ctgttaaact cctgatctac catacatcaa gattacactc aggagtccca     240
tcaaggttca gtggcagtgg gtctggaaca gattattctc tcaccattag caacctggag     300
caagaagata ttgccactta cttttgccaa cagggtaata cgcttccgta cacgttcgga     360
ggggggacca agctggagat cacaggtggc ggtggctcgg gcggtggtgg gtcgggtggc     420
ggcggatctg aggtgaaact gcaggagtca ggacctggcc tggtggcgcc ctcacagagc     480
ctgtccgtca catgcactgt ctcaggggtc tcattacccg actatggtgt aagctggatt     540
cgccagcctc cacgaaaggg tctggagtgg ctgggagtaa tatggggtag tgaaaccaca     600
tactataatt cagctctcaa atccagactg accatcatca aggacaactc caagagccaa     660
gttttcttaa aaatgaacag tctgcaaact gatgacacag ccatttacta ctgtgccaaa     720
cattattact acggtggtag ctatgctatg gactactggg gccaaggaac ctcagtcacc     780
gtctcctcaa atccaaaccc caaccaccct agttcctccg gtagcttttc agatgctgac     840
cttgcggatg gcgtttcagg tgagaagga aaaggaggca gtgatggtgg aggcagccac     900
aggaaagaag gggaagaggc cgacgcccca ggcgtgatcc ccgggattgt ggggctgtc     960
gtggtcgccg tggctggagc catctctagc ttcattgctt accagaaaaa gaagctatgc    1020
ttcaaagaaa ataaacgggg cagaaagaaa ctcctgtata tattcaaaca accatttatg    1080
agaccagtac aaactactca agaggaagat ggctgtagct gccgatttcc agaagaagaa    1140
gaaggaggat gtgaactgag agtgaagttc agcaggagcg cagacgcccc cgcgtacaag    1200
cagggccaga accagctcta taacgagctc aatctaggac gaagagagga gtacgatgtt    1260
ttggacaaga cgtggccg ggaccctgag atgggggaa agccgagaag gaagaaccct    1320
caggaaggcc tgtacaatga actgcagaaa gataagatgg cggaggccta cagtgagatt    1380
gggatgaaag gcgagcgccg gaggggcaag gggcacgatg cctttaccca gggtctcagt    1440
acagccacca aggacaccta cgacgccctt cacatgcagg ccctgccccc tcgctaa       1497
```

<210> SEQ ID NO 31
<211> LENGTH: 488
<212> TYPE: PRT
<213> ORGANISM: Artificial Sequence
<220> FEATURE:
<223> OTHER INFORMATION: F35BBz

<400> SEQUENCE: 31

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
```

```
            35                  40                  45
Asp Ile Ser Lys Tyr Leu Asn Trp Tyr Gln Gln Lys Pro Asp Gly Thr
 50                  55                  60

Val Lys Leu Leu Ile Tyr His Thr Ser Arg Leu His Ser Gly Val Pro
 65                  70                  75                  80

Ser Arg Phe Ser Gly Ser Gly Ser Gly Thr Asp Tyr Ser Leu Thr Ile
                 85                  90                  95

Ser Asn Leu Glu Gln Glu Asp Ile Ala Thr Tyr Phe Cys Gln Gln Gly
                100                 105                 110

Asn Thr Leu Pro Tyr Thr Phe Gly Gly Gly Thr Lys Leu Glu Ile Thr
                115                 120                 125

Gly Gly Gly Gly Ser Gly Gly Gly Ser Gly Gly Gly Ser Glu
                130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
                180                 185                 190

Val Ile Trp Gly Ser Glu Thr Thr Tyr Tyr Asn Ser Ala Leu Lys Ser
                195                 200                 205

Arg Leu Thr Ile Ile Lys Asp Asn Ser Lys Ser Gln Val Phe Leu Lys
210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Gly Ser Phe Ser Asp Ala Asp Leu Ala
                260                 265                 270

Asp Gly Val Ser Gly Gly Glu Gly Lys Gly Gly Ser Asp Gly Gly Gly
                275                 280                 285

Ser His Arg Lys Glu Gly Glu Glu Ala Asp Ala Pro Gly Val Ile Pro
290                 295                 300

Gly Ile Val Gly Ala Val Val Val Ala Val Ala Gly Ala Ile Ser Ser
305                 310                 315                 320

Phe Ile Ala Tyr Gln Lys Lys Lys Leu Cys Phe Lys Glu Asn Lys Arg
                325                 330                 335

Gly Arg Lys Lys Leu Leu Tyr Ile Phe Lys Gln Pro Phe Met Arg Pro
                340                 345                 350

Val Gln Thr Thr Gln Glu Glu Asp Gly Cys Ser Cys Arg Phe Pro Glu
                355                 360                 365

Glu Glu Glu Gly Gly Cys Glu Leu Arg Val Lys Phe Ser Arg Ser Ala
                370                 375                 380

Asp Ala Pro Ala Tyr Lys Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
                420                 425                 430

Gly Leu Tyr Asn Glu Leu Gln Lys Asp Lys Met Ala Glu Ala Tyr Ser
                435                 440                 445

Glu Ile Gly Met Lys Gly Glu Arg Arg Arg Gly Lys Gly His Asp Gly
                450                 455                 460
```

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 32
<211> LENGTH: 1467
<212> TYPE: DNA
<213> ORGANISM: Artificial Sequence
<220> FEATURE:
<223> OTHER INFORMATION: F35BBz

<400> SEQUENCE: 32

```
atggccttac cagtgaccgc cttgctcctg ccgctggcct tgctgctcca cgccgccagg      60
ccggacatcc agatgacaca gactacatcc tccctgtctg cctctctggg agacagagtc     120
accatcagtt gcagggcaag tcaggacatt agtaaatatt taaattggta tcagcagaaa     180
ccagatggaa ctgttaaact cctgatctac catacatcaa gattacactc aggagtccca     240
tcaaggttca gtggcagtgg gtctggaaca gattattctc tcaccattag caacctggag     300
caagaagata ttgccactta cttttgccaa caggtaata cgcttccgta cacgttcgga     360
ggggggacca agctggagat cacaggtggc ggtggctcgg gcggtggtgg gtcgggtggc     420
ggcggatctg aggtgaaact gcaggagtca ggacctggcc tggtggcgcc ctcacagagc     480
ctgtccgtca catgcactgt ctcaggggtc tcattacccg actatggtgt aagctggatt     540
cgccagcctc cacgaaaggg tctggagtgg ctgggagtaa tatggggtag tgaaaccaca     600
tactataatt cagctctcaa atccagactg accatcatca aggacaactc caagagccaa     660
gttttcttaa aaatgaacag tctgcaaact gatgacacag ccatttacta ctgtgccaaa     720
cattattact acggtggtag ctatgctatg gactactggg gccaaggaac ctcagtcacc     780
gtctcctcag gtagcttttc agatgctgac cttgcggatg gcgtttcagg tggagaagga     840
aaaggaggca gtgatggtgg aggcagccac aggaaagaag gggaagaggc cgacgcccca     900
ggcgtgatcc ccgggattgt gggggctgtc gtggtcgccg tggctggagc catctctagc     960
ttcattgctt accagaaaaa gaagctatgc ttcaaagaaa taaacggggc agaaagaaa    1020
ctcctgtata tattcaaaca accatttatg agaccagtac aaactactca agaggaagat    1080
ggctgtagct gccgatttcc agaagaagaa gaaggaggat gtgaactgag agtgaagttc    1140
agcaggagcg cagacgcccc cgcgtacaag cagggccaga accagctcta taacgagctc    1200
aatctaggac gaagagagga gtacgatgtt ttggacaaga cgtggccgg gaccctgag    1260
atgggggaa agccgagaag gaagaaccct caggaaggcc tgtacaatga actgcagaaa    1320
gataagatgg cggaggccta cagtgagatt gggatgaaag cgagcgccg gaggggcaag    1380
gggcacgatg gcctttacca gggtctcagt acagccacca ggacaccta cgacgccctt    1440
cacatgcagg ccctgccccc tcgctaa                                        1467
```

<210> SEQ ID NO 33
<211> LENGTH: 488
<212> TYPE: PRT
<213> ORGANISM: Artificial Sequence
<220> FEATURE:
<223> OTHER INFORMATION: F35BBz-1

<400> SEQUENCE: 33

Met Ala Leu Pro Val Thr Ala Leu Leu Leu Pro Leu Ala Leu Leu Leu
1               5                   10                  15

```
His Ala Ala Arg Pro Asp Ile Gln Met Thr Gln Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Ser Glu
130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Gly Ser Phe Ser Asp Ala Asp Leu Ala
            260                 265                 270

Asp Gly Val Ser Gly Gly Glu Gly Lys Gly Gly Ser Asp Gly Gly Gly
        275                 280                 285

Ser His Arg Lys Glu Gly Glu Glu Ala Asp Ala Pro Gly Val Ile Pro
    290                 295                 300

Gly Ile Val Gly Ala Val Val Ala Val Ala Gly Ala Ile Ser Ser
305                 310                 315                 320

Phe Ile Ala Tyr Gln Lys Lys Lys Leu Cys Phe Lys Glu Asn Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430
```

```
Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485
```

<210> SEQ ID NO 34
<211> LENGTH: 1467
<212> TYPE: DNA
<213> ORGANISM: Artificial Sequence
<220> FEATURE:
<223> OTHER INFORMATION: F35BBz-1

<400> SEQUENCE: 34

| | | | | | |
|---|---|---|---|---|---|
| atggccttac | cagtgaccgc | cttgctcctg | ccgctggcct | tgctgctcca | cgccgccagg | 60 |
| ccggacatcc | agatgacaca | gactacatcc | tccctgtctg | cctctctggg | agacagagtc | 120 |
| accatcagtt | gcagggcaag | tcaggacatt | agtaaatatt | taaattggta | tcagcagaaa | 180 |
| ccagatggaa | ctgttaaact | cctgatctac | catacatcaa | gattacactc | aggagtccca | 240 |
| tcaaggttca | gtggcagtgg | gtctgggaca | gattattctc | tcaccattag | caacctggag | 300 |
| caagaagata | ttgccactta | cttttgccaa | cagggtaata | cgcttccgta | cacgttcgga | 360 |
| ggggggacca | agctggagat | cacaggtggc | ggtggctcgg | gcggtggtgg | gtcgggtggc | 420 |
| ggcggatctg | aggtgaaact | gcaggagtca | ggacctggcc | tggtggcgcc | ctcacagagc | 480 |
| ctgtccgtca | catgcactgt | ctcaggggtc | tcattacccg | actatggtgt | aagctggatt | 540 |
| cgccagcctc | cacgaaaggg | tctggagtgg | ctgggagtaa | tatggggtag | tgaaaccaca | 600 |
| tactataatt | cagctctcaa | atccagactg | accatcatca | aggacaactc | caagagccaa | 660 |
| gttttcttaa | aaatgaacag | tctgcaaact | gatgacacag | ccatttacta | ctgtgccaaa | 720 |
| cattattact | acggtggtag | ctatgctatg | gactactggg | gccaaggaac | ctcagtcacc | 780 |
| gtctcctcag | gtagcttttc | agatgctgac | cttgcggatg | cgtttcagg | tggagaagga | 840 |
| aaaggaggca | gtgatggtgg | aggcagccac | aggaaagaag | gggaagaggc | cgacgcccca | 900 |
| ggcgtgatcc | ccgggattgt | gggggctgtc | gtggtcgccg | tggctggagc | catctctagc | 960 |
| ttcattgctt | accagaaaaa | gaagctatgc | ttcaaagaaa | ataaacgggg | cagaaagaaa | 1020 |
| ctcctgtata | tattcaaaca | accatttatg | agaccagtac | aaactactca | agaggaagat | 1080 |
| ggctgtagct | gccgatttcc | agaagaagaa | gaaggaggat | gtgaactgag | agtgaagttc | 1140 |
| agcaggagcg | cagacgcccc | cgcgtaccag | cagggccaga | accagctcta | taacgagctc | 1200 |
| aatctaggac | gaagagagga | gtacgatgtt | ttggacaaga | gacgtggccg | ggaccctgag | 1260 |
| atggggggaa | agccgagaag | gaagaaccct | caggaaggcc | tgtacaatga | actgcagaaa | 1320 |
| gataagatgg | cggaggccta | cagtgagatt | gggatgaaag | gcgagcgccg | gaggggcaag | 1380 |
| gggcacgatg | gcctttacca | gggtctcagt | acagccacca | aggacaccta | cgacgccctt | 1440 |
| cacatgcagg | ccctgccccc | tcgctaa | | | | 1467 |

<210> SEQ ID NO 35
<211> LENGTH: 186
<212> TYPE: PRT
<213> ORGANISM: Artificial Sequence
<220> FEATURE:
<223> OTHER INFORMATION: CD99 WT

<400> SEQUENCE: 35

```
Met Ala Arg Ala Ala Met Glu Ala Ala Thr Val Val Leu Ala Leu
1               5                   10                  15

Ala Leu Leu Gly Ala Ala Arg Gly Ala Ala Glu Gln Lys Leu Ile
            20                  25                  30

Ser Glu Glu Asp Leu Asn Ser Asp Asp Phe Asn Leu Gly Asp Ala Leu
                35                  40                  45

Glu Asp Pro Asn Met Lys Pro Thr Pro Lys Ala Pro Thr Pro Lys Lys
        50                  55                  60

Pro Ser Gly Gly Phe Asp Leu Glu Asp Ala Leu Pro Gly Gly Gly Gly
65                  70                  75                  80

Gly Gly Ala Gly Glu Lys Pro Gly Asn Arg Pro Gln Pro Asp Pro Lys
                85                  90                  95

Pro Pro Arg Pro His Gly Asp Ser Gly Gly Ile Ser Asp Ser Asp Leu
            100                 105                 110

Ala Asp Ala Ala Gly Gln Gly Gly Gly Ala Gly Arg Arg Gly Ser
                115                 120                 125

Gly Asp Glu Gly Gly His Gly Gly Ala Gly Gly Ala Glu Pro Glu Gly
    130                 135                 140

Thr Pro Gln Gly Leu Val Pro Gly Val Val Ala Ala Val Ala Ala
145                 150                 155                 160

Val Ala Gly Ala Val Ser Ser Phe Val Ala Tyr Gln Arg Arg Arg Leu
                165                 170                 175

Cys Phe Arg Glu Gly Gly Ser Ala Pro Val
            180                 185
```

<210> SEQ ID NO 36
<211> LENGTH: 187
<212> TYPE: PRT
<213> ORGANISM: Artificial Sequence
<220> FEATURE:
<223> OTHER INFORMATION: CD99 TM mutant

<400> SEQUENCE: 36

```
Met Ala Arg Ala Ala Met Glu Ala Ala Thr Val Val Leu Ala Leu
1               5                   10                  15

Ala Leu Leu Gly Ala Ala Arg Gly Ala Ala Glu Gln Lys Leu Ile
            20                  25                  30

Ser Glu Glu Asp Leu Asn Ser Asp Asp Phe Asn Leu Gly Asp Ala Leu
                35                  40                  45

Glu Asp Pro Asn Met Lys Pro Thr Pro Lys Ala Pro Thr Pro Lys Lys
        50                  55                  60

Pro Ser Gly Gly Phe Asp Leu Glu Asp Ala Leu Pro Gly Gly Gly Gly
65                  70                  75                  80

Gly Gly Ala Gly Glu Lys Pro Gly Asn Arg Pro Gln Pro Asp Pro Lys
                85                  90                  95

Pro Pro Arg Pro His Gly Asp Ser Gly Gly Ile Ser Asp Ser Asp Leu
            100                 105                 110

Ala Asp Ala Ala Gly Gln Gly Gly Gly Ala Gly Arg Arg Gly Ser
                115                 120                 125

Gly Asp Glu Gly Gly His Gly Gly Ala Gly Gly Ala Glu Pro Glu Gly
    130                 135                 140

Thr Pro Gln Gly Ala Leu Ile Val Leu Gly Gly Val Ala Gly Leu Leu
145                 150                 155                 160
```

Leu Phe Ile Gly Leu Gly Ile Phe Phe Cys Ala Tyr Gln Arg Arg Arg
            165                 170                 175

Leu Cys Phe Arg Glu Gly Gly Ser Ala Pro Val
            180                 185

<210> SEQ ID NO 37
<211> LENGTH: 177
<212> TYPE: PRT
<213> ORGANISM: Artificial Sequence
<220> FEATURE:
<223> OTHER INFORMATION: CD99 Cyt mutant

<400> SEQUENCE: 37

Met Ala Arg Ala Ala Met Glu Ala Ala Thr Val Val Leu Ala Leu
1               5                   10                  15

Ala Leu Leu Gly Ala Ala Ala Arg Gly Ala Ala Glu Gln Lys Leu Ile
            20                  25                  30

Ser Glu Glu Asp Leu Asn Ser Asp Asp Phe Asn Leu Gly Asp Ala Leu
        35                  40                  45

Glu Asp Pro Asn Met Lys Pro Thr Pro Lys Ala Pro Thr Pro Lys Lys
50                  55                  60

Pro Ser Gly Gly Phe Asp Leu Glu Asp Ala Leu Pro Gly Gly Gly Gly
65                  70                  75                  80

Gly Gly Ala Gly Glu Lys Pro Gly Asn Arg Pro Gln Pro Asp Pro Lys
                85                  90                  95

Pro Pro Arg Pro His Gly Asp Ser Gly Gly Ile Ser Asp Ser Asp Leu
            100                 105                 110

Ala Asp Ala Ala Gly Gln Gly Gly Gly Gly Ala Gly Arg Arg Gly Ser
            115                 120                 125

Gly Asp Glu Gly His Gly Gly Ala Gly Gly Ala Glu Pro Glu Gly
        130                 135                 140

Thr Pro Gln Gly Leu Val Pro Gly Val Val Ala Ala Val Ala Ala
145                 150                 155                 160

Val Ala Gly Ala Val Ser Ser Phe Val Val Arg Cys Arg His Arg Arg
                165                 170                 175

Arg

<210> SEQ ID NO 38
<211> LENGTH: 189
<212> TYPE: PRT
<213> ORGANISM: Artificial Sequence
<220> FEATURE:
<223> OTHER INFORMATION: CD99 TMrst-S mutant

<400> SEQUENCE: 38

Met Ala Arg Ala Ala Met Glu Ala Ala Thr Val Val Leu Ala Leu
1               5                   10                  15

Ala Leu Leu Gly Ala Ala Ala Arg Gly Ala Ala Glu Gln Lys Leu Ile
            20                  25                  30

Ser Glu Glu Asp Leu Asn Ser Asp Asp Phe Asn Leu Gly Asp Ala Leu
        35                  40                  45

Glu Asp Pro Asn Met Lys Pro Thr Pro Lys Ala Pro Thr Pro Lys Lys
50                  55                  60

Pro Ser Gly Gly Phe Asp Leu Glu Asp Ala Leu Pro Gly Gly Gly Gly
65                  70                  75                  80

Gly Gly Ala Gly Glu Lys Pro Gly Asn Arg Pro Gln Pro Asp Pro Lys
                85                  90                  95

-continued

Pro Pro Arg Pro His Gly Asp Ser Gly Gly Ile Ser Asp Ser Asp Leu
            100                 105                 110

Ala Asp Ala Ala Gly Gln Gly Gly Gly Ala Gly Arg Arg Gly Ser
        115                 120                 125

Gly Asp Glu Gly Gly His Gly Gly Ala Gly Gly Ala Glu Pro Glu Gly
        130                 135                 140

Thr Pro Gln Gly Ala Leu Ile Val Leu Gly Gly Val Ala Gly Leu Leu
145                 150                 155                 160

Leu Phe Ile Gly Leu Gly Ala Val Ser Ser Phe Val Ala Tyr Gln Arg
                165                 170                 175

Arg Arg Leu Cys Phe Arg Glu Gly Gly Ser Ala Pro Val
            180                 185

<210> SEQ ID NO 39
<211> LENGTH: 188
<212> TYPE: PRT
<213> ORGANISM: Artificial Sequence
<220> FEATURE:
<223> OTHER INFORMATION: CD99 TMrst-L mutant

<400> SEQUENCE: 39

Met Ala Arg Ala Ala Met Glu Ala Ala Ala Thr Val Val Leu Ala Leu
1               5                   10                  15

Ala Leu Leu Gly Ala Ala Ala Arg Gly Ala Ala Glu Gln Lys Leu Ile
            20                  25                  30

Ser Glu Glu Asp Leu Asn Ser Asp Asp Phe Asn Leu Gly Asp Ala Leu
        35                  40                  45

Glu Asp Pro Asn Met Lys Pro Thr Pro Lys Ala Pro Thr Pro Lys Lys
    50                  55                  60

Pro Ser Gly Gly Phe Asp Leu Glu Asp Ala Leu Pro Gly Gly Gly Gly
65                  70                  75                  80

Gly Gly Ala Gly Glu Lys Pro Gly Asn Arg Pro Gln Pro Asp Pro Lys
                85                  90                  95

Pro Pro Arg Pro His Gly Asp Ser Gly Gly Ile Ser Asp Ser Asp Leu
            100                 105                 110

Ala Asp Ala Ala Gly Gln Gly Gly Gly Ala Gly Arg Arg Gly Ser
        115                 120                 125

Gly Asp Glu Gly Gly His Gly Gly Ala Gly Gly Ala Glu Pro Glu Gly
        130                 135                 140

Thr Pro Gln Gly Ala Leu Ile Val Leu Gly Gly Val Ala Gly Leu Val
145                 150                 155                 160

Ala Ala Val Ala Gly Ala Val Ser Ser Phe Val Ala Tyr Gln Arg Arg
                165                 170                 175

Arg Leu Cys Phe Arg Glu Gly Gly Ser Ala Pro Val
            180                 185

<210> SEQ ID NO 40
<211> LENGTH: 180
<212> TYPE: PRT
<213> ORGANISM: Artificial Sequence
<220> FEATURE:
<223> OTHER INFORMATION: CD99 CytJuxt mutant

<400> SEQUENCE: 40

Met Ala Arg Ala Ala Met Glu Ala Ala Ala Thr Val Val Leu Ala Leu
1               5                   10                  15

Ala Leu Leu Gly Ala Ala Ala Arg Gly Ala Ala Glu Gln Lys Leu Ile
            20                  25                  30

-continued

```
Ser Glu Glu Asp Leu Asn Ser Asp Asp Phe Asn Leu Gly Asp Ala Leu
            35                  40                  45

Glu Asp Pro Asn Met Lys Pro Thr Pro Lys Ala Pro Thr Pro Lys Lys
 50                  55                  60

Pro Ser Gly Gly Phe Asp Leu Glu Asp Ala Leu Pro Gly Gly Gly Gly
 65                  70                  75                  80

Gly Gly Ala Gly Glu Lys Pro Gly Asn Arg Pro Gln Pro Asp Pro Lys
                85                  90                  95

Pro Pro Arg Pro His Gly Asp Ser Gly Ile Ser Asp Ser Asp Leu
            100                 105                 110

Ala Asp Ala Ala Gly Gln Gly Gly Gly Ala Gly Arg Arg Gly Ser
            115                 120                 125

Gly Asp Glu Gly His Gly Gly Ala Gly Ala Glu Pro Glu Gly
        130                 135                 140

Thr Pro Gln Gly Leu Val Pro Gly Val Val Ala Ala Val Ala Ala
145                 150                 155                 160

Val Ala Gly Ala Val Ser Ser Phe Val Ala Tyr Gln Arg Arg Arg Leu
            165                 170                 175

Cys Phe Arg Glu
            180
```

<210> SEQ ID NO 41
<211> LENGTH: 486
<212> TYPE: PRT
<213> ORGANISM: Artificial Sequence
<220> FEATURE:
<223> OTHER INFORMATION: hCD19BBz

<400> SEQUENCE: 41

```
Met Ala Leu Pro Val Thr Ala Leu Leu Leu Pro Leu Ala Leu Leu Leu
 1               5                  10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
 50                  55                  60

Val Lys Leu Leu Ile Tyr His Thr Ser Arg Leu His Ser Gly Val Pro
 65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
            115                 120                 125

Gly Gly Gly Gly Ser Gly Gly Gly Ser Gly Gly Gly Gly Ser Glu
        130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
            165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
            195                 200                 205
```

Arg Leu Thr Ile Ile Lys Asp Asn Ser Lys Ser Gln Val Phe Leu Lys
                210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
                260                 265                 270

Thr Pro Ala Pro Thr Ile Ala Ser Gln Pro Leu Ser Leu Arg Pro Glu
                275                 280                 285

Ala Cys Arg Pro Ala Ala Gly Gly Ala Val His Thr Arg Gly Leu Asp
                290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
                340                 345                 350

Thr Thr Gln Glu Glu Asp Gly Cys Ser Cys Arg Phe Pro Glu Glu Glu
                355                 360                 365

Glu Gly Gly Cys Glu Leu Arg Val Lys Phe Ser Arg Ser Ala Asp Ala
                370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
                435                 440                 445

Gly Met Lys Gly Glu Arg Arg Arg Gly Lys Gly His Asp Gly Leu Tyr
                450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 42
<211> LENGTH: 1461
<212> TYPE: DNA
<213> ORGANISM: Artificial Sequence
<220> FEATURE:
<223> OTHER INFORMATION: hCD19BBz

<400> SEQUENCE: 42
atggccttac cagtgaccgc cttgctcctg ccgctggcct tgctgctcca cgccgccagg     60
ccggacatcc agatgacaca gactacatcc tccctgtctg cctctctggg agacagagtc    120
accatcagtt gcagggcaag tcaggacatt agtaaatatt taaattggta tcagcagaaa    180
ccagatggaa ctgttaaact cctgatctac catacatcaa gattacactc aggagtccca    240
tcaaggttca gtggcagtgg gtctggaaca gattattctc tcaccattag caacctggag    300
caagaagata ttgccactta cttttgccaa cagggtaata cgcttccgta cacgttcgga    360
ggggggacca agctggagat cacaggtggc ggtggctcgg gcggtggtgg gtcgggtggc    420

```
ggcggatctg aggtgaaact gcaggagtca ggacctggcc tggtggcgcc ctcacagagc    480
ctgtccgtca catgcactgt ctcaggggtc tcattacccg actatggtgt aagctggatt    540
cgccagcctc cacgaaaggg tctggagtgg ctgggagtaa tatggggtag tgaaaccaca    600
tactataatt cagctctcaa atccagactg accatcatca aggacaactc caagagccaa    660
gttttcttaa aaatgaacag tctgcaaact gatgacacag ccatttacta ctgtgccaaa    720
cattattact acggtggtag ctatgctatg gactactggg gccaaggaac ctcagtcacc    780
gtctcctcaa ccacgacgcc agcgccgcga ccaccaacac cggcgcccac catcgcgtcg    840
cagcccctgt ccctgcgccc agaggcgtgc cggccagcgg cggggggcgc agtgcacacg    900 aggggggctgg acttcgcctg tgatatctac atctgggcgc ccttggccgg gacttgtggg    960
gtccttctcc tgtcactggt tatcacccct tactgcaaac ggggcagaaa gaaactcctg   1020
tatatattca acaaccatt tatgagacca gtacaaacta ctcaagagga gatggctgt    1080 agctgccgat ttccagaaga agaagaagga ggatgtgaac tgagagtgaa gttcagcagg   1140
agcgcagacg cccccgcgta caagcagggc cagaaccagc tctataacga gctcaatcta   1200
ggacgaagag aggagtacga tgttttggac aagagacgtg gccgggaccc tgagatgggg   1260
ggaaagccga gaaggaagaa ccctcaggaa ggcctgtaca tgaactgca gaaagataag   1320 atggcggagg cctacagtga gattgggatg aaaggcgagc gccggagggg caaggggcac   1380
gatggccttt accagggtct cagtacagcc accaaggaca cctacgacgc ccttcacatg   1440 caggcccctgc cccctcgcta a                                            1461
```

<210> SEQ ID NO 43
<211> LENGTH: 496
<212> TYPE: PRT
<213> ORGANISM: Artificial Sequence
<220> FEATURE:
<223> OTHER INFORMATION: F8TJBBz

<400> SEQUENCE: 43

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175
```

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
            195                 200                 205

Arg Leu Thr Ile Ile Lys Asp Asn Ser Lys Ser Gln Val Phe Leu Lys
            210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
            245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
            290                 295                 300

Ala Asp Ala Pro Gly Val Ile Pro Gly Ile Val Gly Ala Val Val Val
305                 310                 315                 320

Ala Val Ala Gly Ala Ile Ser Ser Phe Ile Ala Tyr Gln Lys Lys Lys
            325                 330                 335

Leu Cys Phe Lys Glu Asn Lys Arg Gly Arg Lys Lys Leu Leu Tyr Ile
            340                 345                 350

Phe Lys Gln Pro Phe Met Arg Pro Val Gln Thr Thr Gln Glu Glu Asp
            355                 360                 365

Gly Cys Ser Cys Arg Phe Pro Glu Glu Glu Gly Gly Cys Glu Leu
            370                 375                 380

Arg Val Lys Phe Ser Arg Ser Ala Asp Ala Pro Ala Tyr Lys Gln Gly
385                 390                 395                 400

Gln Asn Gln Leu Tyr Asn Glu Leu Asn Leu Gly Arg Arg Glu Glu Tyr
            405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
            435                 440                 445

Asp Lys Met Ala Glu Ala Tyr Ser Glu Ile Gly Met Lys Gly Glu Arg
450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
            485                 490                 495

<210> SEQ ID NO 44
<211> LENGTH: 1491
<212> TYPE: DNA
<213> ORGANISM: Artificial Sequence
<220> FEATURE:
<223> OTHER INFORMATION: F8TJBBz

<400> SEQUENCE: 44
atggccttac cagtgaccgc cttgctcctg ccgctggcct tgctgctcca cgccgccagg    60
ccggacatcc agatgacaca gactacatcc tccctgtctg cctctctggg agacagagtc   120
accatcagtt gcagggcaag tcaggacatt agtaaatatt taaattggta tcagcagaaa   180
ccagatggaa ctgttaaact cctgatctac catacatcaa gattacactc aggagtccca   240
tcaaggttca gtggcagtgg gtctgggaca gattattctc tcaccattag caacctggag   300

-continued

```
caagaagata ttgccactta cttttgccaa cagggtaata cgcttccgta cacgttcgga      360
gggggggacca agctggagat cacaggtggc ggtggctcgg gcggtggtgg gtcgggtggc    420
ggcggatctg aggtgaaact gcaggagtca ggacctggcc tggtggcgcc ctcacagagc    480
ctgtccgtca catgcactgt ctcaggggtc tcattacccg actatggtgt aagctggatt    540
cgccagcctc cacgaaaggg tctggagtgg ctgggagtaa tatgggggtag tgaaaccaca    600
tactataatt cagctctcaa atccagactg accatcatca aggacaactc caagagccaa    660
gttttcttaa aaatgaacag tctgcaaact gatgacacag ccatttacta ctgtgccaaa    720
cattattact acggtggtag ctatgctatg gactactggg gccaaggaac ctcagtcacc    780
gtctcctcaa ccacgacgcc agcgccgcga ccaccaacac cggcgcccac catcgcgtcg    840
cagcccctgt ccctgcgccc agaggcgtgc cggccagcgg cggggggcgc agtgcacacg    900
agggggctgg acgccgacgc cccaggcgtg atccccggga ttgtggggc tgtcgtggtc      960
gccgtggctg gagccatctc tagcttcatt gcttaccaga aaagaagct atgcttcaaa    1020
gaaaataaac ggggcagaaa gaaactcctg tatatattca acaaccatt tatgagacca    1080
gtacaaacta ctcaagagga agatggctgt agctgccgat ttccagaaga agaagaagga    1140
ggatgtgaac tgagagtgaa gttcagcagg agcgcagacg cccccgcgta caagcagggc    1200
cagaaccagc tctataacga gctcaatcta ggacgaagag aggagtacga tgttttggac    1260
aagagacgtg gccgggaccc tgagatgggg ggaaagccga gaaggaagaa ccctcaggaa    1320
ggcctgtaca atgaactgca gaaagataag atggcggagg cctacagtga gattgggatg    1380
aaaggcgagc gccggagggg caaggggcac gatggccttt accagggtct cagtacagcc    1440
accaaggaca cctacgacgc ccttcacatg caggccctgc cccctcgcta a             1491
```

IMMUNE SYNAPSE-STABILIZING CHIMERIC ANTIGEN RECEPTOR (CAR) T CELL

SEQUENCE LISTING SUBMISSION VIA EFS-WEB

A computer readable text file, entitled "SequenceListing.txt," created on Oct. 12, 2022 with a file size of 64,923 bytes contains the sequence listing for this application and is hereby incorporated by reference in its entirety.

TECHNICAL FIELD

The present invention relates to a novel chimeric antigen receptor comprising a CD99 region which participates in immune synapse stabilization as a backbone of the chimeric antigen receptor, an immune cell comprising the same, and the uses thereof.

BACKGROUND ART

The development of anticancer therapy using immune cells has been centered on T cells, and as ex-vivo culture and proliferation of tumor-antigen-specific T cells has become possible, anticancer T cell therapy has shown tangible results (Gattinoni L. et al., Nat. Rev. Immunol. 2006; 6(5): 383-93). However, the number of tumor-antigen-specific T cells present in a patient's body is very small, so a long period of one month or more is required to obtain a sufficient number of T cells through ex-vivo proliferation of such T cells, which is undesirable.

Therefore, based on recombinant antibody production technology developed in the field of therapeutic antibodies, technology for obtaining a large amount of tumor-specific T cells within a short period of time has been developed by introducing, into T cells, a chimeric antigen receptor (CAR) gene connecting a recombinant antibody that recognizes a tumor antigen expressed on the surface of cancer cells to a signaling domain that induces T-cell activation, and such T cells are named CAR-T cells (Kershaw M. H. et al., Nat. Rev. Immunol. 2005); 5(12):928-40; Restifo N. P. et al., Nat. Rev. Immunol. 2012; 12(4):269-81).

CAR-T cell therapies are receiving attention because of the dramatic effects thereof in clinical trials targeting hematologic tumors. For CAR-T cell therapy using an antibody recognizing CD19, which is a B-lymphocyte-based hematologic tumor antigen, in early clinical trials, 90% of acute lymphocytic leukemia patients (27 patients out of 30 patients), who failed to respond to conventional therapies, achieved complete remission within one month, and the 6-month overall survival rate was 78%, showing a remarkable therapeutic effect (Maude S. L. et al., N. Engl. J. Med. 2014; 371(16):1507-17). Based on these results, at the end of 2017, two types of CD19 CAR-T cell therapies were successfully commercialized under FDA approval.

Currently, successful cases of CAR-T cell therapy are limited to CD19-positive acute leukemia, and the therapeutic efficiency thereof on solid tumors is reported to be low. Some of the reasons are understood to be that solid tumors create an immunosuppressive tumor microenvironment (Springuel L. et al., BioDrugs. 2019; 33(5):515-37). For example, in the case of CD19-positive hematologic tumors, compared to leukemia, in which tumor cells mainly proliferate in the blood, the therapeutic efficiency of CAR-T cells on lymphoma forming a solid tumor is known to be very low (Sadelain M. et al., Nature. 2017; 545(7655):423-31). Therefore, there is an urgent need for efforts to further improve the function of CAR-T cells (Mardiana S. et al., Sci. Transl. Med. 2019; 11(495)).

A CAR protein is designed in a form in which the variable region (single-chain variable fragment; scFv) of an antibody that recognizes a cancer antigen is connected to an intracellular signaling domain via a backbone (Dotti G. et al., Immunol. Rev. 2014; 257(1):107-26). The intracellular signaling domain is mainly based on the intracellular signaling domain of the CD3 zeta (ζ) chain, which is a signaling subunit of the T-cell receptor (first-generation CAR), and the CAR has been developed in a form in which the intracellular signaling domain of a co-stimulatory molecule, which promotes growth and differentiation of T cells, is added thereto.

To date, efforts have been made to improve the function of CAR-T cells through the modification of CAR proteins, and most of them have been carried out in the form of replacing or adding the signaling domain of a co-stimulatory molecule. For example, two currently commercially available CAR-T cell therapies use the intracellular signaling domains of CD28 and 4-1BB co-stimulatory molecules, respectively (second-generation CAR), followed by attempts for CAR simultaneously including the intracellular signaling domains of CD28 and 4-1BB (third-generation CAR) (van der Stegen S. J. et al., Nat. Rev. Drug Discov. 2015; 14(7):499-509). However, the backbone including the transmembrane domain has been used to date only for the physical function of connecting the scFv to the intracellular signaling domain, and there are few reports of CAR designs in which functionality is imparted to such a region.

In the present invention, it has been ascertained that the membrane protein CD99 improves T cell function through a new mechanism of immune synapse stabilization, and also that the function of CAR-T cells may be improved by using some regions of CD99 as the backbone of the CAR protein, leading to the development of a new CAR-T cell therapy using the same.

The information disclosed in the Background section is provided only for better understanding of the background of the present invention, and therefore it may not include information that forms the prior art that is already obvious to those skilled in the art.

SUMMARY OF THE INVENTION

It is an object of the present invention to provide a chimeric antigen receptor, which exhibits an improved therapeutic effect against tumor by stabilizing an immune synapse formed at a contact region between an immune cell and a target cell, and an immune cell comprising the same.

It is another object of the present invention to provide a nucleic acid encoding the chimeric antigen receptor, an expression vector comprising the nucleic acid, and a virus comprising the expression vector.

It is still another object of the present invention to provide a composition for treating cancer comprising the immune cell, a method of treating cancer using the immune cell, the use of the immune cell for the treatment of cancer, and the use of the immune cell for the manufacture of a medicament for the treatment of cancer.

In order to achieve the above objects, the present invention provides a chimeric antigen receptor comprising a transmembrane domain derived from a CD99 protein.

The present invention also provides a nucleic acid encoding the chimeric antigen receptor, an expression vector comprising the nucleic acid, a virus comprising the expression vector, and an immune cell expressing the chimeric antigen receptor.

The present invention also provides a composition for treating cancer comprising the immune cell, a method of treating cancer using the immune cell, the use of the immune cell for the treatment of cancer, and the use of the immune cell for the manufacture of a medicament for the treatment of cancer.

BRIEF DESCRIPTION OF DRAWINGS

FIG. 2A shows graphs of the CFSE dilution factor flow cytometry in the case of cell division on the $2^{nd}$ and $3^{rd}$ days after TCR stimulation (left) and the cell population ratio (%) among total T ells at each division number, measured using the CFSE dilution factor(right), and FIG. 2B shows graphs of the results of analysis of IL-2- or IFN-γ-producing CD8 T cell ratios over time after TCR stimulation. *p<0.05, p<0.01, *p<0.001 in t-test analysis.

FIG. 3A shows a comparison of immune synapse formation between WT cells or CD99-KO T cells and antigen-presenting cells, in which, 30 minutes after co-culture of anti-TCRβ- and LFA-1-antibody-stained T cells and antigen-presenting cells, confocal microscopy images (left) and the ratio of fluorescence intensity values at the intercellular proximal and distal regions of TCRβ and LFA-1 on the images (right) are illustrated, FIG. 3B shows the results of confocal microscopy of F-actin during immune synapse formation, in which, 30 minutes after co-culture of T cells and antigen-presenting cells, microscopic images of F-actin through Phalloidin staining (left) and the proportion of cells showing F-actin clustered within 1 field of view (a total of 5 fields of view or more being measured) (right) are illustrated, and FIGS. 3C to 3G show the results of F-actin dynamic rearrangement analysis during immune synapse formation (real-time confocal microscopy analysis of activated Life-Act fluorescent-protein-expressing WT or CD99-KO T cells on coverslips coated with anti-CD3 antibody), in which FIG. 3C shows a change in intracellular F-actin distribution and cell morphology over time, FIG. 3D shows the time required for initial cell expansion, FIG. 3E shows a change in cross-sectional area of cells over time, and FIGS. 3F and 3G show the results of measurement of a lamellipodia thickness and a distance of an actin microcluster from the center of the cell (FIG. 3F) and the quantitative analysis of the measured results (FIG. 3G). *p<0.05, p<0.01, *p<0.001 in t-test analysis.

FIGS. 4A to 4D show the results of analysis of F-actin and microtubule rearrangement during immune synapse formation in wild-type T cells and CD99-deficient T cells (real-time confocal microscopy analysis of activated T cells on coverslips coated with anti-CD3 antibody after expression of Life-Act fluorescent protein in WT T cells and CD99-KO cells and staining thereof with a SiR-tubulin reagent), FIG. 4A shows a change in distribution of actin (red) and microtubules (cyan blue) over time, FIG. 4B shows the results of quantitative analysis of the number (left) and length (right) of trajectory microtubules present inside a cell in the early stage (5 minutes) and the late stage (20 minutes) of synapse formation, FIG. 4C shows, as a comparison of intracellular F-actin and microtubule arrangement, the relative results of comparative quantitative analysis of actin and microtubules distributed along the transverse cross-section of the cells (intensity: arbitrary fluorescence intensity), the yellow zone indicating the lamellipodia region. FIG. 4D shows, as enlarged images of the lamellipodia region, the distribution images of microtubules (cyan blue) and actin (red) in lamellipodia (left) and quantitative analysis of the co-localization coefficient (Pearson's coefficient) of two fluorescence values on the images (right). FIG. 4E shows the results of co-immunoprecipitation of tubulin and actin, including immunoblotting using an anti-tubulin antibody and an anti-actin antibody of anti-tubulin antibody immunoprecipitates in WT and CD99-KO T cells after stimulation with anti-CD3 antibody (left), immunoblotting of an isotype control IgG immunoprecipitate (center), and immunoblotting of a cell lysate before immunoprecipitation (right). *p<0.05, ****p<0.0001 in t-test analysis.

FIG. 5A shows results confirming the location of CD99 in the immune synapse cell membrane, in which, 1 hour after co-culture of antigen-presenting cells with T cells stained with anti-TCR antibody and anti-CD99 (upper panel) or anti-LAF-1 antibody and anti-CD99 antibody (lower panel), confocal microscopy images (left) and analysis of co-localization constants between CD99 and TCR or CD99 and LFA-1 (right) are illustrated. FIG. 5B shows results confirming the distribution of CD99, F-actin and tubulin in cells in which immune synapses are formed, including confocal microscopy images stained with Phalloidin (upper panel) or anti-tubulin antibody (lower panel) after 15 minutes of activation of T cells expressing WT-CD99-GFP on coverslips coated with anti-CD3 antibody (left) and the results of quantitative analysis of co-localization coefficients of WT CD99-GFP protein with F-actin or tubulin in the selected portions (dashed squares) in the images (right). FIG. 5C shows the results of co-immunoprecipitation analysis of CD99 with actin and tubulin, including immunoblotting using anti-actin and anti-tubulin antibodies of anti-CD99 antibody immunoprecipitates in WT T cells (right lane), immunoblotting of a control IgG antibody immunoprecipitate (center lane), and immunoblotting of a cell lysate before immunoprecipitation (left lane). ***p<0.001 in t-test analysis.

FIG. 6A schematically shows the structural designs of CD99 mutant proteins, for example, cytoplasmic domain mutant (Cyt), transmembrane domain mutant (TM), transmembrane partial replacement mutants ($TM^{rst-S}$, $TM^{rst-L}$), and mutant ($Cyt^{Juxt}$) in which only the juxtamembrane region exists in the cytoplasmic region. FIG. 6B shows, as the distribution of F-actin and microtubules during immune synapse formation of T cells expressing each CD99 mutant protein-GFP, the results of confocal microscopy analysis including single fluorescence and double fluorescence (CD99/tubulin; tubulin/F-actin) and cell morphology (DIC)

images, in which T cells that express a Life-Act fluorescent protein and each mutant protein-GFP are stained with a SiR-tubulin reagent and then activated for 15 minutes on coverslips coated with anti-CD3 antibody, followed by confocal microscopy.

Figure 7:
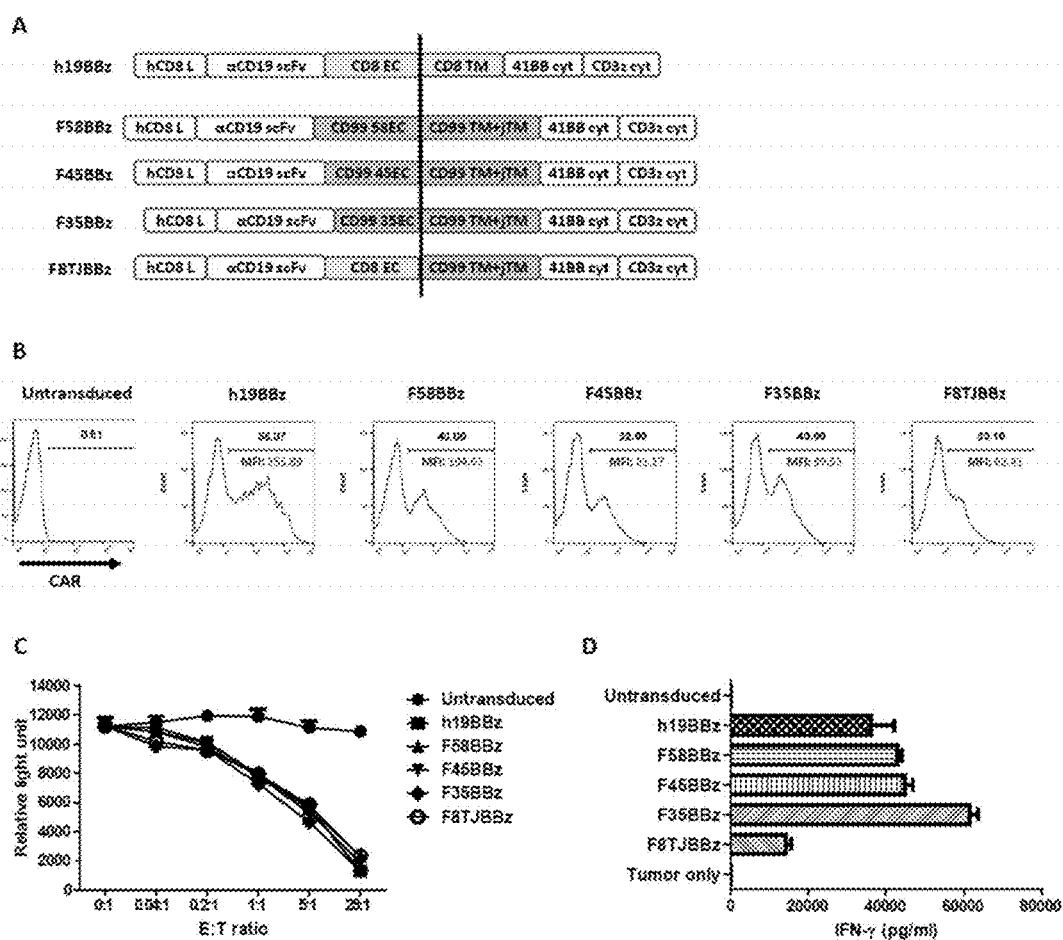

FIG. 7 shows CD99-backbone-based CAR-T cell designs and in-vitro activity verification results.

FIG. 7A schematically shows the structural designs of CAR proteins (hCD8 L: human CD8α leader, αCD19 scFv: anti-CD19 antibody (clone FMC63) single-chain variable fragment, EC: extracellular region, EC58: extracellular 58 amino acid region, EC45: extracellular 45 amino acid region, EC35: extracellular 35 amino acid region, TM: transmembrane region, jTM: juxtamembrane region, and cyt: cytoplasmic region). FIG. 7B shows the expression level of CAR protein on the surface of CAR-T cells (upper number in each graph: ratio of CAR-positive cells (%), and lower number in each graph: MFI (mean fluorescence intensity; mean fluorescence intensity of CAR-positive cells), FIG. 7C is a graph showing the ability of each CAR-T cell to kill Raji-Luc lymphoma cells (relative light unit: luciferase activity value in Raji-Luc cells that survived after overnight culture with CAR-T cells, E:T ratio (effector: target ratio): cell number ratio of co-cultured CAR-T cells (effector) and Raji-Luc cells (target)), and FIG. 7D is a graph showing the amount of IFN-γ that is secreted into the supernatant after co-culture of CAR-T cells and Raji cells.

Figure 8:
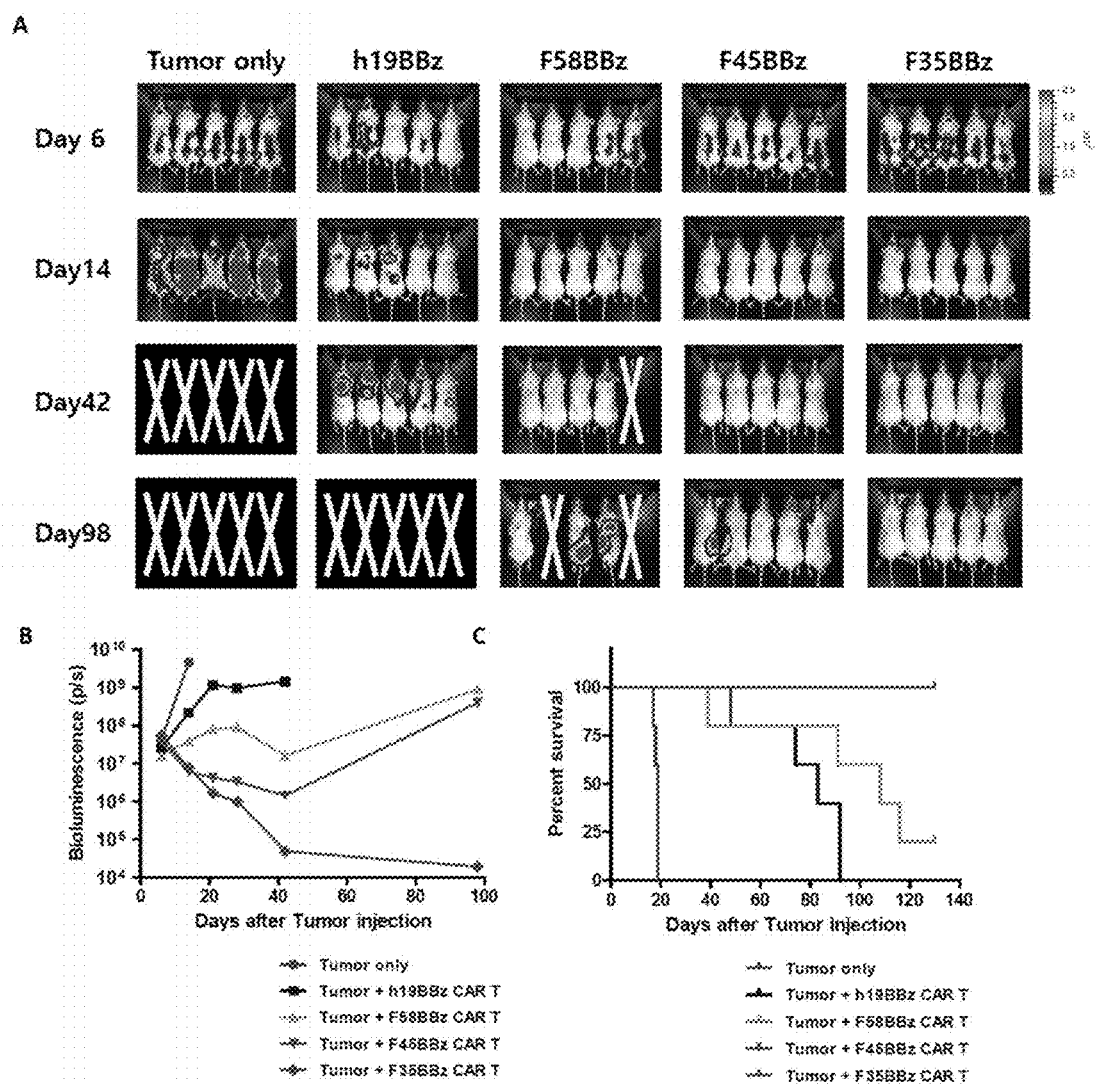

FIG. 8 shows the improving effect of CD99-backbone-based CAR-T cells on tumor removal in vivo.

FIGS. 8A and 8B show representative images over time obtained through bioluminescence imaging of the extent of in-vivo proliferation of tumor cells before injection (day 6) and after injection (days 14-98) of CAR-T cells, at the time of intravenous injection of CAR-T cells on the 7th day after intravenous injection of Raji-Luc cells into NSG mice (day 0) (FIG. 8A) and the results of quantitative measurement thereof (FIG. 8B), and FIG. 8C is a graph showing the survival rate over time of the mice inoculated with Raji-Luc cells and CAR-T cells.

Figure 9:
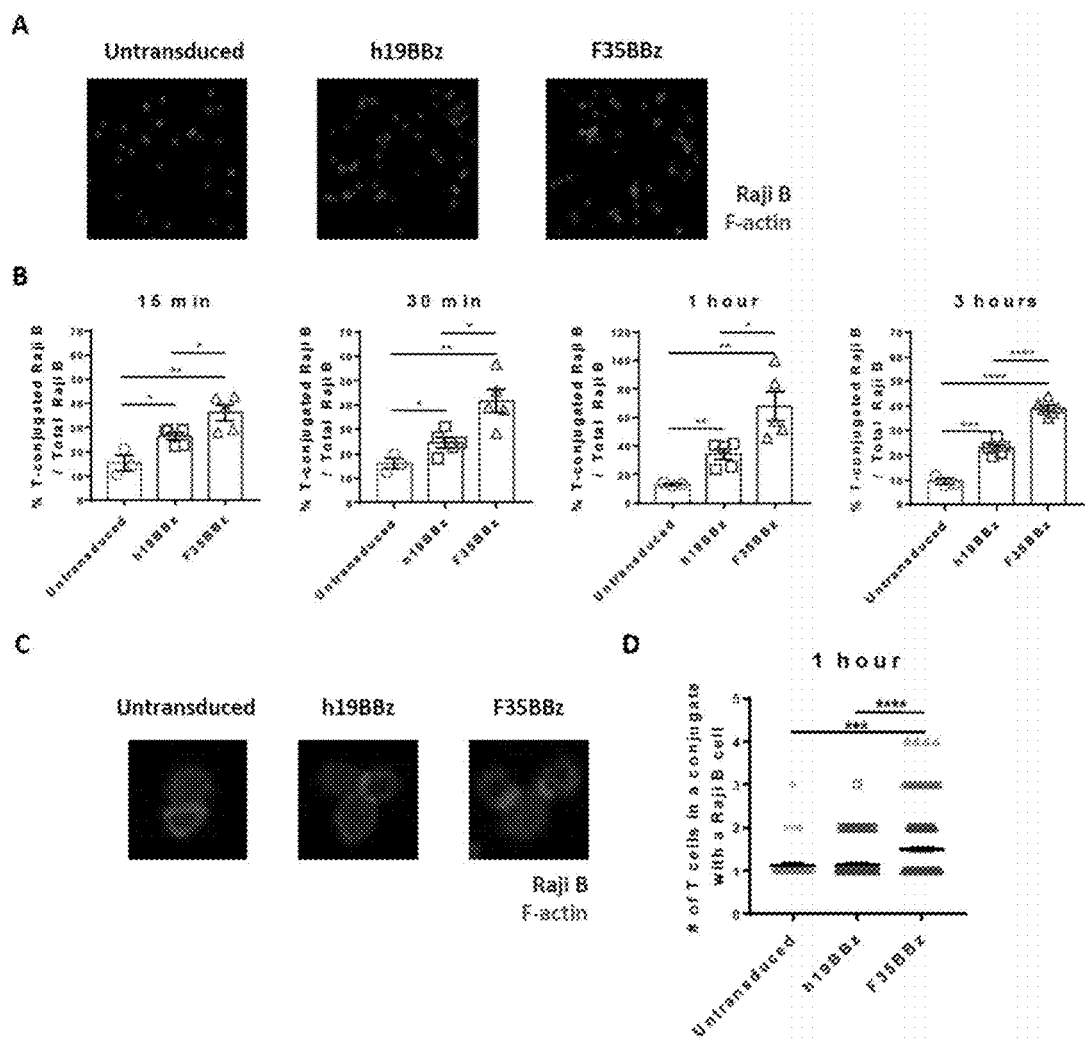

FIG. 9 shows the enhancing effect of CD99-backbone-based CAR-T cells on immune synapse formation.

FIGS. 9A and 9B show confocal microscopy images (after 1 hour) of cells having formed immune synapses during co-culture of CAR-T cells and Raji cells (FIG. 9A) and quantitative changes over time (ratio of Raji cells bound to T cells among Raji cells present per field of view, a total of 3-5 fields of view being measured) (FIG. 9B). FIG. 9C shows representative images (after 1 hour) of Raji cell and CAR-T cell conjugates, and FIG. 9D shows the average number of CAR-T cells that bind to one Raji cell (after 1 hour).

DETAILED DESCRIPTION AND PREFERRED EMBODIMENTS OF THE INVENTION

Unless otherwise defined, all technical and scientific terms used herein have the same meanings as those typically understood by those skilled in the art to which the present invention belongs. Generally, the nomenclature used herein is well known in the art and is typical.

CD99 is a membrane protein expressed in various cell populations, including T cells, and is known to be involved in cell adhesion, cell migration, protein trafficking, and the like (Pasello M. et al., J. Cell. Commun. Signal. 2018; 12(1):55-68). It has been reported that CD99 serves to promote T-cell activation as a co-stimulatory molecule in T cells (Oh K. I. et al., Exp. Mol. Med. 2007; 39(2):176-84), and also that CD99 promotes cell surface expression of cell membrane proteins such as MHC I, TCR, etc. (Sohn H. W. et al., J. Immunol. 2001; 166(2):787-94). As a mechanism of activation of T cells, the possibility that CD99 moves to a lipid raft and regulates rearrangement of the actin cytoskeleton inside T cells has been suggested, but the specific molecular mechanism thereof has not been studied (Yoon S. S. et al., FEBS Lett. 2003; 540(1-3):217-22).

When T cells come into contact with antigen-presenting cells such as dendritic cells, they recognize the peptide antigen presented by the antigen-presenting cells through a T-cell receptor (TCR) and are activated by transmitting the TCR signal to the inside. Here, the cell membrane region of the T cells maintains strong contact with the cell membrane region of the antigen-presenting cells for a considerable period of time, and this contact region is collectively referred to as an immune synapse (Grakoui A. et al., Science. 1999; 285(5425):221-7). It is well known that the formation of immune synapses plays an important role in T-cell activation signaling and also that the actin cytoskeletal rearrangement inside T cells is essential for the formation of immune synapses (Dustin M L, Cooper J A, Nat Immunol. 2000; 1(1):23-9). In addition, recently, along with actin, the microtubule cytoskeleton has also been found to be involved in immune synapses, but studies have not clarified the relationship therebetween (Martin-Cofreces N. B., Sanchez-Madrid F., Front. Immunol. 2018; 9:1174; Dogterom M., Koenderink G. H., Nat. Rev. Mol. Cell. Biol. 2019; 20(1): 38-54).

In the present invention, it has been demonstrated that CD99 plays an important role in the formation of immune synapses, and also that CD99 mediates cytoskeletal rearrangement inside cells. Moreover, as a specific mechanism, it has been investigated that CD99 acts as a bridge molecule connecting the actin cytoskeleton to the microtubule cytoskeleton, which has not been well studied.

Moreover, it has been confirmed that the transmembrane domain and the intracellular juxtamembrane domain of the CD99 molecule play independent roles in binding to microtubule and actin, respectively.

It is known for CAR-T cells that, when the antibody region of the CAR protein comes into contact with the antigen on the surface of tumor cells, immune synapses are formed, similar to when wild-type T cells and antigen-presenting cells are in contact, and it has been reported that the formation of immune synapses is associated with the activity of CAR-T cells (Davenport A. J. et al., Proc. Natl. Acad. Sci. USA. 2018; 115(9): E2068-E76). Therefore, a CAR protein design that promotes immune synapse formation is capable of greatly increasing the activity of CAR-T cells.

Based on experimental results showing that CD99 plays an important role in cytoskeletal rearrangement and immune synapse formation, whether the function of CAR-T cells is improved when replacing the CAR backbone comprising the transmembrane domain in the structure of the current CAR protein with a structure comprising the transmembrane domain of CD99 was tested. As a result, it has been confirmed that CAR-T cells expressing a CAR protein comprising the extracellular domain, transmembrane domain, and intracellular juxtamembrane domain of CD99 exhibit vastly superior tumor therapeutic efficiency compared to conventional CAR-T cells using a CD8 protein region. In addition, it has been confirmed that CAR-T cells comprising a CD99-derived backbone have vastly superior immune synapse formation ability compared to conventional CD8 backbone CAR-T cells.

Ultimately, the present invention is intended to provide a new concept of CAR-T cells having improved function through enhancement of immune synapse formation by introducing a CAR protein comprising a CD99 region.

Accordingly, in one aspect, the present invention is directed to a chimeric antigen receptor (CAR) comprising
(a) an antigen-binding domain;
(b) a backbone comprising an extracellular spacer domain and a transmembrane domain; and
(c) an intracellular signaling domain;
wherein the transmembrane domain comprises a CD99-derived transmembrane domain.

As used herein, the term "backbone" refers to a region comprising an extracellular spacer domain and a transmembrane domain.

As used herein, the term "extracellular spacer domain" refers to a region connecting the antigen-binding domain to the transmembrane domain.

In the present invention, the transmembrane domain (TM) may comprise all or part of a CD99-derived transmembrane domain, and the CD99 is preferably human CD99 having the sequence of SEQ ID NO: 1, but is not limited thereto.

Human CD99 having the sequence of SEQ ID NO: 1 may be encoded by the nucleotide sequence of SEQ ID NO: 2 or a degenerative sequence thereof, but the present invention is not limited thereto.

The CD99-derived extracellular domain may comprise all or part of the amino acid sequence represented by SEQ ID NO: 5, but is not limited thereto. The human CD99-derived extracellular domain having the sequence of SEQ ID NO: 5 may be encoded by the nucleotide sequence of SEQ ID NO: 6 or a degenerative sequence thereof, but the present invention is not limited thereto.

In the present invention, the CD99-derived extracellular domain is represented by the amino acid sequence of SEQ ID NO: 5 or an amino acid sequence comprising contiguous 20 to 70 amino acid residues, and preferably 30 to 60 amino acid residues, in the amino acid sequence represented by SEQ ID NO: 5.

More preferably, the CD99-derived extracellular domain may comprise the amino acid sequence represented by SEQ ID NO: 5, 7, 9, or 11, but is not limited thereto.

Also, in the present invention, the chimeric antigen receptor may further comprise a CD99-derived intracellular juxtamembrane domain.

In the present invention, the "intracellular juxtamembrane domain" may be located between the transmembrane domain and the intracellular signaling domain of the chi-

TABLE 1

Amino acid sequence of human CD99 and nucleotide sequence encoding the same

| Sequence | SEQ ID NO: |
|---|---|
| MARGAALALL LFGLLGVLVA APDGGFDLSD ALPDNENKKP TAIPKKPSAG DDFDLGDAVV DGENDDPRPP NPPKPMPNPN PNHPSSSGSF SDADLADGVS GGEGKGGSDG GGSHRKEGEE ADAPGVIPGI VGAVVVAVAG AISSFIAYQK KKLCFKENAE QGEVDMESHR NANAEPAVQR TLLEK | 1 |
| atggcccgcg gggctgcgct ggcgctgctg ctcttcggcc tgctgggtgt tctggtcgcc gccccggatg gtggtttcga tttatccgat gcccttcctg acaatgaaaa caagaaaccc actgcaatcc ccaagaaacc cagtgctggg gatgactttg acttaggaga tgctgttgtt gatggagaaa atgacgaccc acgaccaccg aacccaccca aaccgatgcc aaatccaaac cccaaccacc ctagttcctc cggtagcttt tcagatgctg accttgcgga tggcgtttca ggtggagaag gaaaaggagg cagtgatggt ggaggcgcc acaggaaaga aggggaagag gccgacgccc caggcgtgat cccggggatt gtggggctg tcgtggtcgc cgtggctgga gccatctcta gcttcattgc ttaccagaaa aagaagctat gcttcaaaga aaatgcagaa caaggggagg tggacatgga gagccaccgg aatgccaacg cagagccagc tgttcagcgt actctttag agaaatag | 2 |

In human CD99 having the amino acid sequence of SEQ ID NO: 1, the amino acid sequences from D23 to D122 correspond to the extracellular domain of CD99, the amino acid sequences from A123 to A147 correspond to the transmembrane domain of CD99, and the amino acid sequences from Y148 to N158 correspond to the juxtamembrane domain of CD99.

A representation in which a one-letter code of an amino acid and a number are coupled, such as "D23", means an amino acid residue at the position of the number. That is, D23 means that the 23$^{rd}$ amino acid is aspartic acid (D).

Preferably, the CD99-derived transmembrane domain comprises the amino acid sequence represented by SEQ ID NO: 3, but is not limited thereto. The human CD99-derived transmembrane domain having the sequence of SEQ ID NO: 3 may be encoded by the nucleotide sequence of SEQ ID NO: 4 or a degenerative sequence thereof, but the present invention is not limited thereto.

In the present invention, the extracellular spacer domain may comprise a CD99-derived and/or CD8-derived extracellular domain, and preferably comprises a human CD99-derived extracellular domain.

meric antigen receptor. In an embodiment of the present invention, it has been confirmed that the CD99-derived intracellular juxtamembrane domain contributes to stabilization of immune synapse formation by mediating interaction with actin.

The CD99-derived intracellular juxtamembrane domain may comprise all or part of the CD99-derived intracellular juxtamembrane domain, and preferably comprises the amino acid sequence represented by SEQ ID NO: 13.

TABLE 2

Sequences of human CD99-derived transmembrane domain and extracellular domain

| Classification | Sequence | SEQ ID NO: |
|---|---|---|
| CD99 TM | APGVIPGIVG AVVVAVAGAI SSFIA | 3 |
| | gccccaggcg tgatccccgg gattgtgggg gctgtcgtgg tcgccgtggc tggagccatc tctagcttca ttgct | 4 |

TABLE 2-continued

Sequences of human CD99-derived transmembrane domain and extracellular domain

| Classification | Sequence | | | SEQ ID NO: |
|---|---|---|---|---|
| CD99 EC | DGGFDLSDAL | PDNENKKPTA | IPKKPSAGDD | 5 |
| | FDLGDAVVDG | ENDDPRPPNP | PKPMPNPNPN | |
| | HPSSSGSFSD | ADLADGVSGG | EGKGGSDGGG | |
| | SHRKEGEEAD | | | |
| | gatggtggtt | tcgatttatc | cgatgccctt | 6 |
| | cctgacaatg | aaaacaagaa | acccactgca | |
| | atccccaaga | aacccagtgc | tggggatgac | |
| | tttgacttag | gagatgctgt | tgttgatgga | |
| | gaaaatgacg | acccacgacc | accgaaccca | |
| | cccaaaccga | tgccaaatcc | aaaccccaac | |
| | caccctagtt | cctccggtag | cttttcagat | |
| | gctgaccttg | cggatggcgt | ttcaggtgga | |
| | gaaggaaaag | gaggcagtga | tggtggaggc | |
| | agccacagga | aagaagggga | agaggccgac | |
| CD99 58EC | DDPRPPNPPK | PMPNPNPNHP | SSSGSFSDAD | 7 |
| | LADGVSGGEG | KGGSDGGGSH | RKEGEEAD | |
| | gacgaccac | gaccaccgaa | cccacccaaa | 8 |
| | ccgatgccaa | atccaaaccc | caaccaccct | |
| | agttcctccg | gtagcttttc | agatgctgac | |
| | cttgcggatg | gcgtttcagg | tggagaagga | |
| | aaaggaggca | gtgatggtgg | aggcagccac | |
| | aggaagaag | gggaagaggc | cgac | |
| CD99 45EC | NPNPNHPSSS | GSFSDADLAD | GVSGGEGKGG | 9 |
| | SDGGGSHRKE | GEEAD | | |
| | aatccaaacc | ccaaccaccc | tagttcctcc | 10 |
| | ggtagctttt | cagatgctga | ccttgcggat | |
| | ggcgtttcag | gtggagaagg | aaaaggaggc | |
| | agtgatggtg | gaggcagcca | caggaaagaa | |
| | ggggaagagg | ccgac | | |
| CD99 35EC | GSFSDADLAD | GVSGGEGKGG | SDGGGSHRKE | 11 |
| | GEEAD | | | |
| | ggtagctttt | cagatgctga | ccttgcggat | 12 |
| | ggcgtttcag | gtggagaagg | aaaaggaggc | |
| | agtgatggtg | gaggcagcca | caggaaagaa | |
| | ggggaagagg | ccgac | | |
| CD99 jTM | YQKKKLCFKE | N | | 13 |
| | taccagaaaa | agaagctatg | cttcaaagaa | 14 |
| | aat | | | |
| CD8 EC | TTTPAPRPPT | PAPTIASQPL | SLRPEACRPA | 15 |
| | AGGAVHTRGL | D | | |
| | accacgacc | cagcgccgcg | accaccaaca | 16 |
| | ccgcgccca | ccatccgtc | gcagccctg | |
| | tccctgcgcc | cagaggcgtg | ccggccagcg | |
| | gcggggggcg | cagtgcacac | gaggggctg | |
| | gac | | | |

In the present invention, the extracellular spacer domain may further comprise a hinge domain.

The hinge domain may be comprised of any oligopeptide or polypeptide, and may comprise 1 to 100 amino acid residues, and preferably 10 to 70 amino acid residues, and preferably comprises all or part of a CD8-derived hinge domain comprising the amino acid sequence represented by SEQ ID NO: 15, but is not limited thereto.

In the present invention, the intracellular signaling domain is a portion located in the cytoplasm, which is the inside of the cell membrane of an immune cell, and is a region that activates the immune response of immune cells by transmitting a signal into the cells when the antigen-binding domain included in the extracellular domain binds to a target antigen.

In the present invention, the intracellular signaling domain is preferably at least one intracellular signaling domain selected from the group consisting of CD3 zeta (ζ), CD3 gamma (γ), CD3 delta (δ), CD3 epsilon (ε), FcR gamma, FcR beta, CD5, CD22, CD79a, CD79b, and CD66d, but is not limited thereto, and is more preferably CD3 zeta (ζ). The CD3 zeta (ζ) intracellular signaling domain according to the present invention may comprise the amino acid sequence of SEQ ID NO: 17 or the amino acid sequence of SEQ ID NO: 19 in which, glutamine (Q) which is the 14$^{th}$ amino acid residue in the sequence of SEQ ID NO: 17, is substituted with lysine (K), but is not limited thereto.

In addition, the intracellular signaling domain according to the present invention may further comprise a co-stimulatory domain, but is not limited thereto. The co-stimulatory domain according to the present invention is preferably at least one co-stimulatory domain selected from the group consisting of CD2, CD7, CD27, CD28, CD30, CD40, 4-1BB (CD137), OX40 (CD134), ICOS, LFA-1, GITR, MyD88, DAP1, PD-1, LIGHT, NKG2C, B7-H3, and ligands specifically binding to CD83, but is not limited thereto.

Preferably, the intracellular signaling domain according to the present invention comprises a CD3 zeta (ζ) intracellular signaling domain comprising the amino acid sequence of SEQ ID NO: 17 or 19, and a 4-1BB co-stimulatory domain comprising the amino acid sequence represented by SEQ ID NO: 21, but is not limited thereto.

TABLE 3

Sequences of CD3 zeta (G) intracellular signaling domain and 4-1BB co-stimulatory domain

| Classification | Sequence | | | SEQ ID NO: |
|---|---|---|---|---|
| CD3 zeta intracellular signaling domain (wild type) | RVKFSRSADA | PAYQQGQNQL | YNELNLGRRE | 17 |
| | EYDVLDKRRG | RDPEMGGKPR | RKNPQEGLYN | |
| | ELQKDKMAEA | YSEIGMKGER | RRGKGHDGLY | |
| | QGLSTATKDT | YDALHMQALP | PR | |
| | agagtgaagt | tcagcaggag | cgcagacgcc | 18 |
| | cccgcgtacc | agcagggcca | gaaccagctc | |
| | tataacgagc | tcaatctagg | acgaagagag | |
| | gagtacgatg | ttttggacaa | gagacgtggc | |
| | cgggaccctg | agatgggggg | aaagccgaga | |
| | aggaagaacc | ctcaggaagg | cctgtacaat | |
| | gaactgcaga | aagataagat | ggcggaggcc | |
| | tacagtgaga | ttgggatgaa | aggcgagcgc | |
| | cggaggggca | aggggcacga | tggcctttac | |
| | cagggtctca | gtacagccac | caaggacacc | |
| | tacgacgccc | ttcacatgca | ggccctgccc | |
| | cctcgc | | | |
| CD3 zeta intracellular signaling domain (mutant) | RVKFSRSADA | PAYKQGQNQL | YNELNLGRRE | 19 |
| | EYDVLDKRRG | RDPEMGGKPR | RKNPQEGLYN | |
| | ELQKDKMAEA | YSEIGMKGER | RRGKGHDGLY | |
| | QGLSTATKDT | YDALHMQALP | PR | |
| | agagtgaagt | tcagcaggag | cgcagacgcc | 20 |
| | cccgcgtaca | agcagggcca | gaaccagctc | |
| | tataacgagc | tcaatctagg | acgaagagag | |
| | gagtacgatg | ttttggacaa | gagacgtggc | |
| | cgggaccctg | agatgggggg | aaagccgaga | |
| | aggaagaacc | ctcaggaagg | cctgtacaat | |
| | gaactgcaga | aagataagat | ggcggaggcc | |
| | tacagtgaga | ttgggatgaa | aggcgagcgc | |
| | cggaggggca | aggggcacga | tggcctttac | |
| | cagggtctca | gtacagccac | caaggacacc | |
| | tacgacgccc | ttcacatgca | ggccctgccc | |
| | cctcgc | | | |
| 4-1BB co-stimulatory domain | KRGRKKLLYI | FKQPFMRPVQ | TTQEEDGCSC | 21 |
| | RFPEEEEGGC | EL | | |
| | aaacgggca | gaaagaaact | cctgtatata | 22 |
| | ttcaaacaac | catttatgag | accagtacaa | |
| | actactcaag | aggaagatgg | ctgtagctgc | |
| | cgatttccag | aagaagaaga | aggaggatgt | |
| | gaactg | | | |

In particular, the chimeric antigen receptor according to the present invention may comprise at least one intracellular signaling domain and at least one co-stimulatory domain.

When the chimeric antigen receptor according to the present invention comprises at least one intracellular signaling domain and at least one co-stimulatory domain, at least one intracellular signaling domain and at least one co-stimulatory domain may be connected in series to each other. As such, each domain may be directly linked, or may be linked optionally or via an oligopeptide linker composed of 2 to 10 amino acid residues or a polypeptide linker, and the linker sequence preferably comprises a contiguous glycine-serine sequence.

In the present invention, the chimeric antigen receptor may further comprise a T-cell-immune-function-promoting factor, and examples of the T-cell-immune-function-promoting factor may comprise, but are not limited to, IL-7 (interleukin 7), IL-12, IL-15, IL-18, IL-21, and CCL19. Reference may be made to WO 2016/056228 A regarding the T-cell-immune-function-promoting factor.

In the present invention, the chimeric antigen receptor may further comprise an interleukin receptor chain comprising a JAK binding motif and a STAT 3/5 association motif, and an example thereof may include, but is not limited to, IL-2Rβ. In this regard, reference may be made to WO 2016/127257 A.

The first-generation CAR comprises an extracellular domain comprising a region that recognizes an antigen specifically expressed in cancer cells, a transmembrane domain, and an intracellular signaling domain, and uses only CD3 as the signaling domain, but the therapeutic effect thereof on cancer is insignificant, and the duration of the effect is short, which is undesirable. This first-generation CAR is specifically described in U.S. Pat. No. 6,319,494, which is incorporated herein by reference.

The second-generation CAR comprising a co-stimulatory domain (CD28 or CD137/4-1BB) and CD3ζ, which are coupled to each other, was prepared in order to improve the response to immune cells, and the number of CAR-containing immune cells remaining in the body was significantly increased compared to the first-generation CAR. The second-generation CAR used one co-stimulatory domain, whereas the third-generation CAR used two or more co-stimulatory domains. The co-stimulatory domain may be coupled with 4-1BB, CD28, or OX40 in order to achieve expansion and persistence of immune cells comprising CAR in vivo. The second-generation CAR is specifically described in U.S. Pat. Nos. 7,741,465, 7,446,190 and 9,212,229, and the third-generation CAR is specifically described in U.S. Pat. No. 8,822,647, all of which are incorporated herein by reference.

In the fourth-generation CAR, an additional gene encoding cytokine such as IL-12 or IL-15 is included to allow additional expression of the CAR-based immune protein of cytokine, and the fifth-generation CAR further includes an interleukin receptor chain such as IL-2Rβ in order to enhance immune cells. The fourth-generation CAR is specifically described in U.S. Pat. No. 10,316,102, and the fifth-generation CAR is specifically described in U.S. Pat. No. 10,336,810, both of which are incorporated herein by reference.

In the present invention, the antigen-binding domain may comprise, but is not limited to, an antibody or antigen-binding fragment thereof that specifically binds to an antigen selected from the group consisting of:

4-1BB, B cell maturation antigen (BCMA), B-cell activating factor (BAFF), B7-H3, B7-H6, carbonic anhydrase 9 (CA9; also known as CAIX or G250), cancer/testis antigen 1B (CTAG1B; also known as NY-ESO-1 or LAGE2B), carcinoembryonic antigen (CEA), cyclin, cyclin A2, cyclin B1, C-C motif chemokine ligand 1 (CCL-1), CCR4, CD3, CD4, CD19, CD20, CD22, CD23, CD24, CD30, CD33, CD38, CD40, CD44, CD44v6, CD44v7/8, CD52, CD58, CD62, CD79A, CD79B, CD80, CD123, CD133, CD138, CD171, chondroitin sulfate proteoglycan 4 (CSPG4), claudin-18 (CLDN18), CLDN6, cytotoxic T-lymphocyte-associated protein 4 (CTLA-4), tyrosine-protein kinase Met (c-Met), DLL3, epidermal growth factor receptor (EGFR), truncated epidermal growth factor receptor (tEGFR), type III epidermal growth factor receptor mutation (EGFRvIII), epithelial glycoprotein 2 (EPG-2), epithelial glycoprotein 40 (EPG-40), ephrin B2, ephrin receptor A2 (EPHA2), estrogen receptor, Fc receptor, Fc-receptor-like 5 (FCRL5; also known as Fc receptor homolog 5 or FCRH5), fibroblast growth factor 23 (FGF23), folate binding protein (FBP), folate receptor alpha (FOLR1), folate receptor beta (FOLR2), GD2 (ganglioside GD2, O-acetylated GD2 (OGD2)), ganglioside GD3, glycoprotein 100 (gp100), glypican-3 (GPC3), G protein-coupled receptor 5D (GPCR5D), granulocyte-macrophage colony-stimulating factor (GM-CSF), Her2/neu (receptor tyrosine kinase erbB2), Her3 (erb-B3), Her4 (erb-B4), erbB dimers, human high-molecular-weight melanoma-associated antigen (HMW-MAA), hepatitis B surface antigen (HBsAg), human leukocyte antigen A1 (HLA-A1), human leukocyte antigen A2 (HLA-A2), IL-22 receptor alpha (IL-22Ra), IL-13 receptor alpha 2 (IL-13Ra2), inducible T-cell costimulator (ICOS), insulin-like growth factor 1 receptor (IGF-1 receptor), integrin αvβ6, interferon receptor, IFNγ, interleukin-2 receptor (IL-2R), interleukin-4 receptor (IL-4R), interleukin-5 receptor (IL-5R), interleukin-6 receptor (IL-6R), interleukin-17 receptor A (IL-17RA), interleukin-31 receptor (IL-31R), interleukin-36 receptor (IL-36R), kinase insert domain receptor (kdr), L1 cell adhesion molecule (L1-CAM), CE7 epitope of L1-CAM, leucine-rich repeat-containing 8 family member A (LRRC8A), Lewis Y, lymphocyte-activation gene 3 (LAG3), melanoma-associated antigen (MAGE) A1, MAGEA3, MAGEA6, MAGEA10, mesothelin (MSLN), murine cytomegalovirus (CMV), mucin 1 (MUC1), natural killer group 2 member D (NKG2D) ligands, melan A (MART-1), nerve growth factor (NGF), neural cell adhesion molecule (NCAM), neuropilin-1 (NRP-1), neuropilin-2 (NRP-2), oncofetal antigen, PD-L1, preferentially expressed antigen of melanoma (PRAME), progesterone receptor, prostate-specific antigen, prostate stem cell antigen (PSCA), prostate-specific membrane antigen (PSMA), receptor activator of nuclear factor kappa-B ligand (RANKL), receptor-tyrosine-kinase-like orphan receptor 1 (ROR1), SLAM family member 7 (SLAMF7), survivin, trophoblast glycoprotein (TPBG; also known as 5T4), tumor-associated glycoprotein 72 (TAG72), tyrosine-related protein 1 (TRP1; also known as TYRP1 or gp75), tyrosine-related protein 2 (TRP2; also known as dopachrome tautomerase, dopachrome delta-isomerase or DCT), and Wilms' tumor 1 (WT1).

In the present invention, the "fragment" of an antibody is a fragment having an antigen-binding function, and is used to have a meaning comprising scFv, Fab, F(ab')2, Fv, and nanobody fragments.

A "single-chain Fv" or "scFv" antibody fragment comprises the VH and VL domains of an antibody, and such domains are present within a single polypeptide chain. The Fv polypeptide may further comprise a polypeptide linker between the VH and VL domains that enables scFv to form the desired structure for antigen binding.

An "Fv" fragment is an antibody fragment comprising complete antibody recognition and binding sites. This region is comprised of a dimer in which one heavy-chain variable domain and one light-chain variable domain are tightly and substantially covalently associated with, for example, an scFv.

A "Fab" fragment comprises the variable and constant domains of a light chain and the variable and first constant domains (CH1) of a heavy chain. "F(ab')$_2$" antibody fragments generally comprise a pair of Fab fragments that are covalently linked near the carboxy terminus thereof by a hinge cysteine therebetween.

A "nanobody" is a fragment comprising a monomeric variable antibody domain. It is mainly comprised of a low-molecular-weight fragment derived from a camelid antibody domain that shows target specificity only with a monomeric heavy chain.

In the present invention, the antigen-binding fragment is a single-chain variable fragment (scFv) or nanobody of an antibody.

In the present invention, the antigen-binding domain preferably comprises an anti-CD19 antibody or an scFv thereof, and the scFv of the anti-CD19 antibody comprises the amino acid sequence represented by SEQ ID NO: 23, but is not limited thereto.

TABLE 4 scFv sequence of anti-CD19 antibody

| Classification | Sequence | SEQ ID NO: |
|---|---|---|
| aCD19 scFv | DIQMTQTTSS LSASLGDRVT ISCRASQDIS KYLNWYQQKP DGTVKLLIYH TSRLHSGVPS RFSGSGSGTD YSLTISNLEQ EDIATYFCQQ GNTLPYTFGG GTKLEITGGG GSGGGGSGGG GSEVKLQESG PGLVAPSQSL SVTCTVSGVS LPDYGVSWIR QPPRKGLEWL GVIWGSETTY YNSALKSRLT IIKDNSKSQV FLKMNSLQTD DTAIYYCAKH YYYGGSYAMD YWGQGTSVTV SS | 23 |
| | gacatccaga tgacacagac tacatcctcc ctgtctgcct ctctgggaga cagagtcacc atcagttgca gggcaagtca ggacattagt aaatatttaa attggtatca gcagaaacca gatggaactg ttaaactcct gatctaccat acatcaagat tacactcagg agtcccatca aggttcagtg gcagtgggtc tggaacagat tattctctca ccattagcaa cctggagcaa gaagatattg ccacttactt ttgccaacag ggtaatacgc ttccgtacac gttcggaggg gggaccaagc tggagatcaa aggtggcggt ggctcgggcg gtggtgggtc gggtggcggc ggatctgagg tgaaactgca ggagtcagga cctggcctgg tggcgccctc acagagcctg tccgtcacat gcactgtctc aggggtctca ttacccgact atggtgtaag ctggattcgc cagcctccac gaaagggtct ggagtggctg ggagtaatat ggggtagtga aaccacatac tataattcag ctctcaaatc cagactgacc atcatcaagg acaactccaa gagccaagtt | 24 |

TABLE 4-continued scFv sequence of anti-CD19 antibody

| Classification | Sequence | SEQ ID NO: |
|---|---|---|
| | ttcttaaaaa tgaacagtct gcaaactgat gacacagcca tttactactg tgccaaacat tattactacg gtggtagcta tgctatggac tactggggcc aaggaacctc agtcaccgtc tcctca | |

In the present invention, a signal peptide (SP) is further comprised at the N-terminus of the antigen-binding domain. In the present invention, the signal peptide may be derived from a molecule selected from the group consisting of CD8α, GM-CSF receptor α, Ig-kappa, and IgG1 heavy chain, but is not limited thereto, and is preferably a CD8α signal peptide, and the CD8α signal peptide may comprise the amino acid sequence represented by SEQ ID NO: 25.

TABLE 5

Sequence of CD8a signal peptide

| Classification | Sequence | SEQ ID NO: |
|---|---|---|
| hCD8L | MALPVTALLL PLALLLHAAR P | 25 |
| | atggccttac cagtgaccgc cttgctcctg ccgctggcct tgctgctcca cgccgccagg ccg | 26 |

In a preferred embodiment, the chimeric antigen receptor according to the present invention comprises
  a CD99-derived extracellular domain represented by SEQ ID NO: 5, 7, 9, or 11;
  a CD99-derived transmembrane domain represented by SEQ ID NO: 3; and
  a CD99-derived intracellular juxtamembrane domain represented by SEQ ID NO: 13.

In addition, the chimeric antigen receptor according to the present invention may further comprise
  a 4-1BB co-stimulatory domain represented by SEQ ID NO: 21;
  a CD3 zeta (ζ) intracellular signaling domain represented by SEQ ID NO: 17 or 19; and/or
  a CD8 signal peptide represented by SEQ ID NO: 25, but is not limited thereto.

In an exemplary embodiment of the present invention, the chimeric antigen receptor comprising an antigen-binding domain for CD19 may comprise the amino acid sequence represented by SEQ ID NO: 27, 29, 31, or 33, or a variant thereof having sequence identity of 80% or more, preferably 90% or more, more preferably 95% or more, and most preferably 99% or more to the amino acid sequence described above.

TABLE 6

Sequence of chimeric antigen receptor protein according to the present invention

| Classification | Sequence | SEQ ID NO: |
|---|---|---|
| F58BBz | MALPVTALLL PLALLLHAAR PDIQMTQTTS SLSASLGDRV TISCRASQDI SKYLNWYQQK PDGTVKLLIY HTSRLHSGVP SRFSGSGSGT | 27 |

TABLE 6-continued

Sequence of chimeric antigen receptor protein according to the present invention

| Classification | Sequence | SEQ ID NO: |
|---|---|---|
| | DYSLTISNLE QEDIATYFCQ QGNTLPYTFG GGTKLEITGG GGSGGGGSGG GGSEVKLQES GPGLVAPSQS LSVTCTVSGV SLPDYGVSWI RQPPRKGLEW LGVIWGSETT YYNSALKSRL TIIKDNSKSQ VFLKMNSLQT DDTAIYYCAK HYYYGGSYAM DYWGQGTSVT VSSDDPRPPN PPKPMPNPNP NHPSSSGSFS DADLADGVSG GEGKGGSDGG GSHRKEGEEA DAPGVIPGIV GAVVVAVAGA ISSFIAYQKK KLCFKENKRG RKKLLYIFKQ PFMRPVQTTQ EEDGCSCRFP EEEEGGCELR VKFSRSADAP AYKQGQNQLY NELNLGRREE YDVLDKRRGR DPEMGGKPRR KNPQEGLYNE LQKDKMAEAY SEIGMKGERR RGKGHDGLYQ GLSTATKDTY DALHMQALPP R | |
| | atggccttac cagtgaccgc cttgctcctg ccgctggcct tgctgctcca cgccgccagg ccggacatcc agatgacaca gactacatcc tccctgtctg cctctctggg agacagagtc accatcagtt gcagggcaag tcaggacatt agtaaatatt taaattggta tcagcagaaa ccagatggaa ctgttaaact cctgatctac catacatcaa gattacactc aggagtccca tcaaggttca gtggcagtgg gtctggaaca gattattctc tcaccattag caacctggag caagaagata ttgccactta cttttgccaa cagggtaata cgcttccgta cacgttcgga ggggggacca agctggagat cacaggtggc ggtggctcgg gcggtggtgg gtcgggtggc ggcggatctg aggtgaaact gcaggagtca ggacctggcc tggtggcgcc ctcacagagc ctgtccgtca catgcactgt ctcagggtc tcattacccg actatggtgt aagctggatt cgccagcctc cacgaaaggg tctggagtgg ctgggagtaa tatggggtag tgaaaccaca tactataatt cagctctcaa atccagactg accatcatca aggacaactc caagagccaa gttttcttaa aaatgaacag tctgcaaact gatgacacag ccatttacta ctgtgccaaa cattattact acggtggtag ctatgctatg gactactggg gccaaggaac ctcagtcacc gtctcctcag acgacccacg accaccgaac ccacccaaac cgatgccaaa tccaaacccc aaccaccta gttcctccgg tagcttttca gatgctgacc ttgcggatgg cgtttcaggt ggagaaggaa aaggaggcag tgatggtgga ggcagccaca ggaaagaagg ggaagaggcc gacgccccag gcgtgatccc cgggattgtg ggggctgtcg tggtcgccgt ggctggagcc atctctagct tcattgctta ccagaaaaag aagctatgct tcaaagaaaa taaacggggc agaaagaaac tcctgtatat attcaaacaa ccatttatga gaccagtaca aactactcaa gaggaagatg gctgtagctg ccgatttcca gaagaagaag aaggaggatg tgaactgaga gtgaagttca gcaggagcgc agacgccccc gcgtacaagc agggccagaa ccagctctat aacgagctca atctaggacg aagagaggag tacgatgttt tggacaagag acgtggccgg gaccctgaga tgggggaaa gccgagaagg aagaaccctc aggaaggcct gtacaatgaa ctgcagaaag ataagatggc ggaggcctac agtgagattg ggatgaaagg cgagcgccgg aggggcaagg ggcacgatgg cctttaccag ggtctcagta cagccaccaa ggacacctac gacgcccttc acatgcaggc cctgccccct cgctaa | 28 |
| F45BBz | MALPVTALLL PLALLLHAAR PDIQMTQTTS SLSASLGDRV TISCRASQDI SKYLNWYQQK PDGTVKLLIY HTSRLHSGVP SRFSGSGSGT DYSLTISNLE QEDIATYFCQ QGNTLPYTFG GGTKLEITGG GGSGGGGSGG GGSEVKLQES | 29 |

TABLE 6-continued

Sequence of chimeric antigen receptor protein according to the present invention

| Classification | Sequence | SEQ ID NO: |
|---|---|---|
| | GPGLVAPSQS LSVTCTVSGV SLPDYGVSWI RQPPRKGLEW LGVIWGSETT YYNSALKSRL TIIKDNSKSQ VFLKMNSLQT DDTAIYYCAK HYYYGGSYAM DYWGQGTSVT VSSNPNPNHP SSSGSFSDAD LADGVSGGEG KGGSDGGGSH RKEGEEADAP GVIPGIVGAV VVAVAGAISS FIAYQKKKLC FKENKRGRKK LLYIFKQPFM RPVQTTQEED GCSCRFPEEE EGGCELRVKF SRSADAPAYK QGQNQLYNEL NLGRREEYDV LDKRRGRDPE MGGKPRRKNP QEGLYNELQK DKMAEAYSEI GMKGERRRGK GHDGLYQGLS TATKDTYDAL HMQALPPR | |
| | atggccttac cagtgaccgc cttgctcctg ccgctggcct tgctgctcca cgccgccagg ccggacatcc agatgacaca gactacatcc tccctgtctg cctctctggg agacagagtc accatcagtt gcagggcaag tcaggacatt agtaaatatt taaattggta tcagcagaaa ccagatggaa ctgttaaact cctgatctac catacatcaa gattacactc aggagtccca tcaaggttca gtggcagtgg gtctggaaca gattattctc tcaccattag caacctggag caagaagata ttgccactta cttttgccaa cagggtaata cgcttccgta cacgttcgga ggggggacca agctggagat cacaggtggc ggtggctcgg gcggtggtgg gtcgggtggc ggcggatctg aggtgaaact gcaggagtca ggacctggcc tggtggcgcc ctcacagagc ctgtccgtca catgcactgt ctcaggggtc tcattacccg actatggtgt aagctggatt cgccagcctc cacgaaaggg tctggagtgg ctgggagtaa tatgggggtag tgaaaccaca tactataatt cagctctcaa atccagactg accatcatca aggacaactc caagagccaa gttttcttaa aaatgaacag tctgcaaact gatgacacag ccatttacta ctgtgccaaa cattattact acggtggtag ctatgctatg gactactggg gccaaggaac ctcagtcacc gtctcctcaa atccaaaccc caaccaccct agttcctccg gtagcttttc agatgctgac cttgcggatg gcgtttcagg tggagaagga aaaggaggca gtgatggtgg aggcagccac aggaaagaag gggaagaggc cgacgcccca ggcgtgatcc ccgggattgt ggggctgtc gtggtcgccg tggctggagc catctctagc ttcattgctt accagaaaaa gaagctatgc ttcaaagaaa ataaacgggg cagaaagaaa ctcctgtata tattcaaaca accatttatg agaccagtac aaactactca agaggaagat ggctgtagct gccgatttcc agaagaagaa gaaggaggat gtgaactgag agtgaagttc agcaggagcg cagacgcccc cgcgtacaag cagggccaga accagctcta taacgagctc aatctaggac aagagagga gtacgatgtt ttggacaaga gacgtggccg ggaccctgag atgggggaa agccgagaag gaagaaccct caggaaggcc tgtacaatga actgcagaaa gataagatgg cggaggccta cagtgagatt gggatgaaag cgagcgccg gaggggcaag gggcacgatg gcctttacca gggtctcagt acagccacca aggacaccta cgacgccctt cacatgcagg ccctgccccc tcgctaa | 30 |
| F35BBz | MALPVTALLL PLALLLHAAR PDIQMTQTTS SLSASLGDRV TISCRASQDI SKYLNWYQQK PDGTVKLLIY HTSRLHSGVP SRFSGSGSGT DYSLTISNLE QEDIATYFCQ QGNTLPYTFG GGTKLEITGG GGSGGGGSGG GGSEVKLQES GPGLVAPSQS LSVTCTVSGV SLPDYGVSWI RQPPRKGLEW LGVIWGSETT YYNSALKSRL TIIKDNSKSQ VFLKMNSLQT DDTAIYYCAK HYYYGGSYAM DYWGQGTSVT VSSGSFSDAD LADGVSGGEG KGGSDGGGSH RKEGEEADAP | 31 |

TABLE 6-continued

Sequence of chimeric antigen receptor protein according to the present invention

| Classification | Sequence | SEQ ID NO: |
|---|---|---|
| | GVIPGIVGAV VVAVAGAISS FIAYQKKKLC FKENKRGRKK LLYIFKQPFM RPVQTTQEED GCSCRFPEEE EGGCELRVKF SRSADAPAYK QGQNQLYNEL NLGRREEYDV LDKRRGRDPE MGGKPRRKNP QEGLYNELQK DKMAEAYSEI GMKGERRRGK GHDGLYQGLS TATKDTYDAL HMQALPPR | |
| | atggccttac cagtgaccgc cttgctcctg ccgctggcct tgctgctcca cgccgccagg ccggacatcc agatgacaca gactacatcc tccctgtctg cctctctggg agacagagtc accatcagtt gcagggcaag tcaggacatt agtaaatatt taaattggta tcagcagaaa ccagatggaa ctgttaaact cctgatctac catacatcaa gattacactc aggagtccca tcaaggttca gtggcagtgg gtctggaaca gattattctc tcaccattag caacctggag caagaagata ttgccactta cttttgccaa cagggtaata cgcttccgta cacgttcgga gggggggacca agctggagat cacaggtggc ggtggctcgg gcggtggtgg gtcgggtggc ggcggatctg aggtgaaact gcaggagtca ggacctggcc tggtggcgcc ctcacagagc ctgtccgtca catgcactgt ctcaggggtc tcattacccg actatggtgt aagctggatt cgccagcctc cacgaaaggg tctggagtgg ctgggagtaa tatggggtag tgaaaccaca tactataatt cagctctcaa atccagactg accatcatca aggacaactc caagagccaa gttttcttaa aaatgaacag tctgcaaact gatgacacag ccatttacta ctgtgccaaa cattattact acggtggtag ctatgctatg gactactggg gccaaggaac ctcagtcacc gtctcctcag gtagcttttc agatgctgac cttgcggatg gcgtttcagg tggagaagga aaaggaggca gtgatggtgg aggcagccac aggaaagaag gggaagaggc cgacgcccca ggcgtgatcc ccgggattgt gggggctgtc gtggtcgccg tggctggagc catctctagc ttcattgctt accagaaaaa gaagctatgc ttcaaagaaa ataaacgggg cagaaagaaa ctcctgtata tattcaaaca accatttatg agaccagtac aaactactca agaggaagat ggctgtagct gccgatttcc agaagaagaa gaaggaggat gtgaactgag agtgaagttc agcaggagcg cagacgcccc cgcgtacaag cagggccaga accagctcta taacgagctc aatctaggac gaagagagga gtacgatgtt ttggacaaga gacgtggccg ggaccctgag atgggggaa agccgagaag aagaaccct caggaaggcc tgtacaatga actgcagaaa gataagatgg cggaggccta cagtgagatt gggatgaaag cgagcgccg gaggggcaag gggcacgatg gcctttacca gggtctcagt acagccacca aggacaccta cgacgccctt cacatgcagg ccctgccccc tcgctaa | 32 |
| F35BBZ-1 | MALPVTALLL PLALLLHAAR PDIQMTQTTS SLSASLGDRV TISCRASQDI SKYLNWYQQK PDGTVKLLIY HTSRLHSGVP SRFSGSGSGT DYSLTISNLE QEDIATYFCQ QGNTLPYTFG GGTKLEITGG GGSGGGGSGG GGSEVKLQES GPGLVAPSQS LSVTCTVSGV SLPDYGVSWI RQPPRKGLEW LGVIWGSETT YYNSALKSRL TIIKDNSKSQ VFLKMNSLQT DDTAIYYCAK HYYYGGSYAM DYWGQGTSVT VSSGSFSDAD LADGVSGGEG KGGSDGGGSH RKEGEEADAP GVIPGIVGAV VVAVAGAISS FIAYQKKKLC FKENKRGRKK LLYIFKQPFM RPVQTTQEED GCSCRFPEEE EGGCELRVKF SRSADAPAYQ QGQNQLYNEL NLGRREEYDV LDKRRGRDPE | 33 |

TABLE 6-continued

Sequence of chimeric antigen receptor protein according to the present invention

| Classification | Sequence | SEQ ID NO: |
|---|---|---|
| | MGGKPRRKNP QEGLYNELQK DKMAEAYSEI GMKGERRRGK GHDGLYQGLS TATKDTYDAL HMQALPPR | |
| | atggccttac cagtgaccgc cttgctcctg<br>ccgctggcct tgctgctcca cgccgccagg<br>ccggacatcc agatgacaca gactacatcc<br>tccctgtctg cctctctggg agacagagtc<br>accatcagtt gcagggcaag tcaggacatt<br>agtaaatatt taaattggta tcagcagaaa<br>ccagatggaa ctgttaaact cctgatctac<br>catacatcaa gattacactc aggagtccca<br>tcaaggttca gtggcagtgg gtctggaaca<br>gattattctc tcaccattag caacctggag<br>caagaagata ttgccactta cttttgccaa<br>cagggtaata cgcttccgta cacgttcgga<br>ggggggacca agctggagat cacaggtggc<br>ggtggctcgg gcggtggtgg gtcgggtggc<br>ggcggatctg aggtgaaact gcaggagtca<br>ggacctggcc tggtggcgcc ctcacagagc<br>ctgtccgtca catgcactgt ctcaggggtc<br>tcattacccg actatggtgt aagctggatt<br>cgccagcctc cacgaaaggg tctggagtgg<br>ctgggagtaa tatggggtag tgaaaccaca<br>tactataatt cagctctcaa atccagactg<br>accatcatca aggacaactc caagagccaa<br>gttttcttaa aaatgaacag tctgcaaact<br>gatgacacag ccatttacta ctgtgccaaa<br>cattattact acggtggtag ctatgctatg<br>gactactggg gccaaggaac ctcagtcacc<br>gtctcctcag gtagcttttc agatgctgac<br>cttgcggatg gcgtttcagg tggagaagga<br>aaaggaggca gtgatggtgg aggcagccac<br>aggaaagaag gggaagaggc cgacgcccca<br>ggcgtgatcc ccgggattgt ggggctgtc<br>gtggtcgccg tggctggagc catctctagc<br>ttcattgctt accagaaaaa gaagctatgc<br>ttcaaagaaa ataaacgggg cagaaagaaa<br>ctcctgtata tattcaaaca accatttatg<br>agaccagtac aaactactca agaggaagat<br>ggctgtagct gccgatttcc agaagaagaa<br>gaaggaggat gtgaactgag agtgaagttc<br>agcaggagcg cagacgcccc cgcgtaccag<br>cagggccaga accagctcta taacgagctc<br>aatctaggac gaagagagga gtacgatgtt<br>ttggacaaga gacgtggccg ggaccctgag<br>atgggggaa agccgagaag gaagaaccct<br>caggaaggcc tgtacaatga actgcagaaa<br>gataagatgg cggaggccta cagtgagatt<br>gggatgaaag gcgagcgccg gaggggcaag<br>gggcacgatg gccttacca gggtctcagt<br>acagccacca aggacaccta cgacgccctt<br>cacatgcagg ccctgccccc tcgctaa | 34 |

In another aspect, the present invention is directed to a nucleic acid encoding the chimeric antigen receptor.

The nucleic acid (polynucleotide) encoding the chimeric antigen receptor according to the present invention may be modified through codon optimization, which is due to the degeneracy of codons, and the presence of many nucleotide sequences encoding the polypeptides or variant fragments thereof may be well understood by those of ordinary skill in the art. Some of these polynucleotides (nucleic acids) retain minimal homology with the nucleotide sequence of any naturally occurring gene.

In particular, polynucleotides (nucleic acids) that vary due to differences in codon usage, for example, polynucleotides (nucleic acids) optimized for codon selection in humans, primates and/or mammals, are preferred.

In the present invention, the nucleic acid encoding the chimeric antigen receptor comprises a nucleotide sequence encoding the CD99-derived extracellular domain and represented by SEQ ID NO: 6, 8, 10, or 12;

a nucleotide sequence encoding the CD99-derived transmembrane domain and represented by SEQ ID NO: 4 and a nucleotide sequence encoding the CD99-derived intracellular juxtamembrane domain and represented by SEQ ID NO: 14, and further comprises a nucleotide sequence encoding the 4-1BB co-stimulatory domain and represented by SEQ ID NO: 22;

a nucleotide sequence encoding the CD3 zeta (ζ) intracellular signaling domain and represented by SEQ ID NO: 18 or 20; and/or a nucleotide sequence encoding the CD8 signal peptide and represented by SEQ ID NO: 26, but the present invention is not limited thereto.

Preferably, the nucleic acid further comprises a nucleotide sequence encoding the single-chain variable fragment (scFv) of an anti-CD19 antibody and represented by SEQ ID NO: 24.

In a preferred embodiment, the nucleic acid sequence encoding the chimeric antigen receptor according to the present invention comprises the nucleotide sequence represented by SEQ ID NO: 28, 30, 32 or 34, or a variant thereof having sequence identity of 80% or more, preferably 90% or more, more preferably 95% or more, and most preferably 99% or more to the nucleotide sequence described above.

In still another aspect, the present invention is directed to an expression vector comprising the nucleic acid and a virus comprising the expression vector.

As used herein, the term "vector" refers to a nucleic acid molecule capable of transferring or transporting another nucleic acid molecule. The transferred nucleic acid is generally linked to a vector nucleic acid molecule, and, for example is inserted into a vector nucleic acid molecule. The vector may comprise a sequence that directs autonomous replication in the cells, or may comprise a sequence sufficient to permit integration into host cell DNA. The vector may be selected from the group consisting of DNA, RNA, plasmids, lentiviral vectors, adenoviral vectors, and retroviral vectors, but is not limited thereto.

In the present invention, the nucleic acid or the vector is transfected into a viral packaging cell line. A variety of different techniques that are commonly used to introduce exogenous nucleic acid (DNA or RNA) into prokaryotic or eukaryotic host cells for "transfection", for example, electrophoresis, calcium phosphate precipitation, DEAE-dextran transfection, lipofection, etc., may be used.

In the present invention, the virus produced from the viral packaging cell line is transduced into immune cells. The nucleic acid of the virus that is "transduced" into the cells is used to produce a chimeric antigen receptor protein, either in the state of being inserted into the genome of the cells or not.

In yet another aspect, the present invention is directed to an immune cell expressing the chimeric antigen receptor on the surface thereof.

In the present invention, the immune cells may be T cells, NK cells, NKT cells, or macrophages, but are not limited thereto, and are preferably T cells.

The immune cells expressing the chimeric antigen receptor according to the present invention may be CAR-T cells (chimeric antigen receptor T cells), CAR-NK cells (chimeric antigen receptor natural killer cells), CAR-NKT cells (chimeric antigen receptor natural killer T cells), or CAR-macrophages (chimeric antigen receptor macrophages).

In the present invention, the T cells may be selected from the group consisting of CD4-positive T cells, CD8-positive cytotoxic T lymphocytes (CTL), gamma-delta T cells, tumor-infiltrating lymphocytes (TIL), and T cells isolated from peripheral blood mononuclear cells (PBMCs).

In still yet another aspect, the present invention is directed to a composition for treating cancer comprising the immune cells (e.g. T cells) expressing the chimeric antigen receptor.

In the present invention, "cancer" and "tumor" are used to have the same meaning, and refer to or mean a physiological condition in mammals, typically characterized by unregulated cell growth and proliferation.

The types of cancer that may be treated using the CAR of the present invention include not only vascularized tumors but also non-vascularized or not yet vascularized tumors. The cancer may include non-solid tumors (e.g. hematologic tumors such as leukemia and lymphoma), or may include solid tumors. The types of cancer that may be treated using the CAR of the present invention include carcinoma, blastoma, sarcoma, and certain leukemia or lymphoid malignancies, benign and malignant tumors, for example, sarcoma, carcinoma and melanoma, but are not limited thereto. Also included are adult tumors/cancer and pediatric tumors/cancer.

Hematologic cancer is cancer of the blood or bone marrow. Examples of hematologic (or hematopoietic) cancer include acute leukemia (e.g. acute lymphocytic leukemia, acute myeloid leukemia, myeloblastic leukemia, prolymphocytic leukemia, myeloid monocytic leukemia, monocytic leukemia, and erythroleukemia), chronic leukemia (e.g. chronic lymphocytic (granulocytic) leukemia, chronic myeloid leukemia, and chronic lymphocytic leukemia), polycythemia vera, lymphoma, Hodgkin's disease, non-Hodgkin's lymphoma (delayed and high-stage forms), multiple myeloma, Waldenstrom's macroglobulinemia, heavy-chain disease, myelodysplastic syndrome, hair-cell leukemia, and leukemia including myelodysplasia.

Solid tumors are abnormal masses of tissue that generally do not include cysts or liquid zones. Solid tumors may be benign or malignant. Different types of solid tumors are named for the types of cells that form them (e.g. sarcomas, carcinomas, and lymphomas). Examples of solid tumors such as sarcomas and carcinomas include fibrosarcoma, myxosarcoma, liposarcoma, chondrosarcoma, osteosarcoma, other sarcomas, synovioma, mesothelioma, Ewing tumor, leiomyosarcoma, rhabdomyosarcoma, rectal carcinoma, lymphoid malignancy, colorectal cancer, stomach cancer, pancreatic cancer, breast cancer, lung cancer, ovarian cancer, prostate cancer, pharyngeal cancer, hepatocellular carcinoma, squamous cell carcinoma, basal cell carcinoma, adenocarcinoma, sweat gland carcinoma, medullary thyroid carcinoma, papillary thyroid carcinoma, pheochromocytoma, sebaceous adenocarcinoma, papillary carcinoma, papillary adenocarcinoma, medullary carcinoma, bronchial carcinoma, renal cell carcinoma, liver tumor, cholangiocarcinoma, choriocarcinoma, Wilms' tumor, cervical cancer, testicular tumors, seminoma, bladder cancer, melanoma, and CNS tumors (e.g. gliomas (e.g. brainstem glioma and mixed glioma), glioblastoma (also known as glioblastoma multiforme), astrocytoma, CNS lymphoma, germinoma, medullary blastoma, schwannoma craniopharyngioma, ependymoma, pinealoma, hemangioblastoma, acoustic neuroma, oligodendroglioma, meningioma, neuroblastoma, retinoblastoma, and brain metastasis).

The therapeutic composition of the present invention is a composition for the prevention or treatment of cancer, and the term "prevention" of the present invention refers to any action that inhibits cancer or delays the progression of cancer by administration of the composition of the present invention, and "treatment" means inhibiting the development of cancer and alleviating or eliminating symptoms thereof.

The pharmaceutical composition comprising the immune cells expressing the chimeric antigen receptor according to the present invention may further comprise a pharmaceutically acceptable excipient. Examples of such excipients include surfactants, preferably nonionic surfactants such as polysorbate series, buffers such as neutral buffered saline, phosphate buffered saline and the like, sugars or sugar alcohols such as glucose, mannose, sucrose, dextran, mannitol and the like, amino acids, proteins or polypeptides such as glycine, histidine and the like, antioxidants, chelating agents such as EDTA or glutathione, penetrants, supplements, and preservatives, but are not limited thereto.

The composition of the present invention may be formulated using methods known in the art in order to provide rapid, sustained or delayed release of the active ingredient after administration to a mammal other than a human. A formulation may be in the form of a powder, granule, tablet, emulsion, syrup, aerosol, soft or hard gelatin capsule, sterile injectable solution, or sterile powder.

In further another aspect, the present invention is directed to a method of treating cancer comprising administering immune cells expressing the chimeric antigen receptor to a subject.

The present invention is also directed to the use of the immune cells for the treatment of cancer.

The present invention is also directed to the use of the immune cells for the manufacture of a medicament for the treatment of cancer.

The subject may be a mammal having a tumor, particularly a human, but is not limited thereto.

The immune cells expressing the chimeric antigen receptor according to the present invention or the composition comprising the same may be administered orally or through infusion, intravenous injection, intramuscular injection, subcutaneous injection, intraperitoneal injection, intrarectal administration, topical administration, intranasal injection, etc., but the present invention is not limited thereto.

The dosage of the active ingredient may be appropriately selected depending on various factors, such as the route of administration, the age, gender, and weight of the patient, and the severity of the disease, and the therapeutic composition according to the present invention may be administered in combination with a known compound effective at preventing, ameliorating or treating cancer symptoms.

Hereinafter, the present invention will be described in more detail with reference to examples. However, it will be obvious to those skilled in the art that these examples are provided only for illustration of the present invention, and should not be construed as limiting the scope of the present invention.

Example 1

Study of Function of CD99-Derived Transmembrane Protein

Example 1-1

Mouse and Cell Line

CD99-knockout mice (B6.Cd99$^{Gt(pU-21T)44Imeg}$) were purchased from the Institute of Resource Development and Analysis, Kumamoto University, and H60 congenic mice (B6.CH60) were obtained from Dr. Derry Roopenian of Jackson laboratory, USA. Immunodeficient NSG mice were purchased from Jackson laboratory. Raji lymphoma cells were purchased from ATCC.

Example 1-2

Establishment of WT and CD99-KO Mouse CD8 T-Cell Line

After intraperitoneal injection of $2\times10^7$ cells/300 μl of splenocytes isolated from B6.CH60 mice into CD99 wild-type (WT) B6 mice and CD99-deficient (CD99-KO) B6 mice, splenocytes ($2.5\times10^6$ cells/ml) removed from each mouse on the 30th day and irradiated (2000 rad) B6.CH60 splenocytes ($3.5\times10^6$ cells/ml) were cultured together in the presence of human IL-2 (50 U/ml, Sigma-Aldrich), and WT and CD99-KO H60-specific CD8 T cells were allowed to proliferate. By inducing reactivation by culturing such T cells together with irradiated B6.CH60 splenocytes in the presence of human IL-2 (50 U/ml) every week, an H60-specific wild-type CD8 T-cell line and a CD99-deficient CD8 T-cell line were established.

Example 1-3

Preparation of Retrovirus Vector for Expression of Mouse CD99 Wild-Type Protein and Mutant Protein cDNA encoding the mouse CD99 wild-type protein (WT) and the transmembrane domain (TM) and intracellular signaling domain (Cyt) mutant proteins was prepared through PCR and cloned into the EcoRI restriction enzyme site of a pcDNA3-YFP plasmid (Addgene #13033). From this plasmid, CD99-YFP DNA was cleaved with HindIII/XbaI restriction enzymes and extracted, and a MSCV Puro plasmid (Addgene #68469) was cleaved with an XhoI restriction enzyme, followed by Klenow enzyme treatment and blunt-end cloning to construct pMSCV-CD99-YFP, pMSCV-CD99TM-YFP, and pMSCV-CD99Cyto-YFP vectors. The amino acid sequence of each CD99 protein is shown in Table 7 below.

TABLE 7

Sequences of Myc-tag-labeled mouse CD99 WT protein and mutant proteins

| Protein name | Amino acid sequence | | | | SEQ ID NO: |
|---|---|---|---|---|---|
| CD99 WT | MARAAMEAAA | TVVLALALLG | AAARGAAEQK | LISEEDLNSD | 35 |
| | DFNLGDALED | PNMKPTPKAP | TPKKPSGGFD | LEDALPGGGG | |
| | GGAGEKPGNR | PQPDPKPPPRP | HGDSGGISDS | DLADAAGQGG | |
| | GGAGRRGSGD | EGGHGGAGGA | EPEGTPQGLV | PGVVAAVVAA | |
| | VAGAVSSFVA | YQRRRLCFRE | GGSAPV | | |

TABLE 7-continued

Sequences of Myc-tag-labeled mouse CD99 WT protein and mutant proteins

| Protein name | Amino acid sequence | SEQ ID NO: |
|---|---|---|
| CD99 TM mutant | MARAAMEAAA TVVLALALLG AAARGAAEQK LISEEDLNSD DFNLGDALED PNMKPTPKAP TPKKPSGGFD LEDALPGGGG GGAGEKPGNR PQPDPKPPRP HGDSGGISDS DLADAAGQGG GGAGRRGSGD EGGHGGAGGA EPEGTPQGAL IVLGGVAGLL LFIGLGIFFC AYQRRRLCFR EGGSAPV | 36 |
| CD99 Cyt mutant | MARAAMEAAA TVVLALALLG AAARGAAEQK LISEEDLNSD DFNLGDALED PNMKPTPKAP TPKKPSGGFD LEDALPGGGG GGAGEKPGNR PQPDPKPPRP HGDSGGISDS DLADAAGQGG GGAGRRGSGD EGGHGGAGGA EPEGTPQGLV PGVVAAVVAA VAGAVSSFVV RCRHRRR | 37 |
| CD99 TMrst-S mutant | MARAAMEAAA TVVLALALLG AAARGAAEQ KLISEEDLNS DDFNLGDALE DPNMKPTPKA PTPKKPSGGF DLEDALPGGG GGGAGEKPGN RPQPDPKPPR PHGDSGGISD SDLADAAGQG GGGAGRRGSG DEGGHGGAGG AEPEGTPQGA LIVLGGVAGL LLFIGLGAVS SFVAYQRRRL CFREGGSAPV | 38 |
| CD99 TMrst-L mutant | MARAAMEAAA TVVLALALLG AAARGAAEQK LISEEDLNSD DFNLGDALED PNMKPTPKAP TPKKPSGGFD LEDALPGGGG GGAGEKPGNR PQPDPKPPRP HGDSGGISDS DLADAAGQGG GGAGRRGSGD EGGHGGAGGA EPEGTPQGAL IVLGGVAGLV AAVAGAVSSF VAYQRRRLCF REGGSAPV | 39 |
| CD99 CytJuxt mutant | MARAAMEAAA TVVLALALLG AAARGAAEQK LISEEDLNSD DFNLGDALED PNMKPTPKAP TPKKPSGGFD LEDALPGGGG GGAGEKPGNR PQPDPKPPRP HGDSGGISDS DLADAAGQGG GGAGRRGSGD EGGHGGAGGA EPEGTPQGLV PGVVAAVVAA VAGAVSSFVA YQRRRLCFRE | 40 |

Example 1-4

Production of Retrovirus for CD99 Expression and Transduction Into Mouse T Cells Each WT or mutant CD99-YFP expression retroviral plasmid was transfected into Platinum-E cells (Cell Biolabs) as a retroviral packaging cell line using polyethyleneimine (Polysciences), and the culture supernatant containing the retrovirus secreted for 24-48 hours was harvested and filtered (0.45-μm filter). The culture supernatant was added to the activated CD99-KO CD8 T-cell line in the presence of polybrene (4 μg/ml, Santa Cruz) to transduce a retrovirus. Subsequently, these cells were treated with puromycin (1 mg/ml, Georgiachem) so as to select only the transduced cells. Thereafter, cells expressing the YFP fusion protein were separated using a flow cytometer (FACS-Aria II, BD Biosciences) to establish each T-cell line, and cell lines were maintained through periodic activation.

Example 1-5

Confirmation of T-Cell Division and Cytokine Production Ability

The cells obtained from lymph nodes of wild-type mice and CD99-deficient mice were labeled with CFSE (5 μM, eBioscience), added to a 96-well plate coated with an anti-CD3 antibody (145-2C11, 1 μg/ml, BD PharmMingen) (5×10⁵ cells/well), and then co-cultured with an anti-CD28 antibody (37.51, 0.5 μg/ml, BD PharmMingen) to activate T cells. 24 hours, 48 hours, and 72 hours after activation, the cells were harvested, and the cell surface was stained with an anti-CD8 antibody (53-6.7, eBioscience), after which cell division was confirmed by measuring the extent of dilution of CFSE stained on CD8 T cells using flow cytometry (FACS-LSRII, BD Bioscience).

In order to confirm the ability of T cells to produce cytokine, for each time period after activation, cells treated with brefeldin A (3 μg/ml, eBioscience) for 4 hours before harvest were harvested, fixed at room temperature for 20 minutes using paraformaldehyde (4%, CellNest), and then permeabilized using PBS containing Triton-X100 (0.5%, Amresco) and BSA (0.1%, Bovogen), after which the cells were stained with an anti-CD8 antibody, an anti-IL-2 antibody (JES6-5H4, eBioscience), and an anti-IFN-γ antibody (XMG1.2, eBioscience), and the fraction and mean fluorescence intensity of the stained cells were measured through flow cytometry.

Example 1-6

T Cell Confocal Microscopy to Confirm Immune Synapse Formation

In order to observe the formation of immune synapses between T cells and antigen-presenting cells, the DC2.4 cell line with H60 antigen expressed was stained with CMTMR (10 μM, Invitrogen) or anti-ICAM-1 antibody (YN1/1.7.4, eBioscience), and a WT or CD99-KO CD8 T-cell line on the fourth day after activation, through mixed culture with B6.CH60 splenocytes was stained with an anti-TCRβ antibody (H57-597, eBioscience) and an anti-LFA-1 antibody (2D7, BD PharmMingen). Thereafter, the two cell populations were mixed with 1×10⁵ cells/200 μl each and co-cultured for 30 minutes or 1 hour on a coverslip coated with poly-L-lysine. Thereafter, the cells were washed with warm PBS, added with 4% paraformaldehyde, and fixed at room temperature for 20 minutes, and then the coverslip was transferred onto a glass slide and mounted. In order to image F-actin, after fixation, the cells were permeabilized with PBS containing Triton-X100 (0.25%) for 10 minutes. Thereafter, the cells were stained with Phalloidin-Alexa Fluor 647 (Invitrogen) for 30 minutes at room temperature, washed with PBS, transferred onto a glass slide, and mounted.

In order to image the cross section of the immune synapse of T cells, the T cells activated for 7 days were isolated and cultured ($1 \times 10^5$ cells/200 μl) for 15 minutes on a coverslip coated with an anti-CD3 antibody (10 μg/ml), followed by fixing and permeabilization. Thereafter, F-actin and microtubule networks were observed through staining with Phalloidin-Alexa Fluor 647 and anti-α-tubulin antibody (DM1A, Millipore).

In order to image F-actin and microtubule rearrangement in real time, a LifeAct-mCherry vector was transfected into the WT or CD99-KO T-cell line using electroporation (Amaxa), and in order to measure tubulin dynamics, while the cells into which a tubulin-staining probe was penetrated using the SiR-tubulin Kit (Cytoskeleton) were cultured on a coverslip coated with an anti-CD3 antibody (10 μg/ml), the rearrangement of F-actin and microtubules, during which immune synapses were formed by T cells, was photographed using a confocal microscope in real time every 20 seconds. All microscopy was performed using a FluoView1000 or FluoView3000 confocal microscope (Olympus), and image analysis was performed using FluoView software (Olympus), cellSens software (Olympus), or ImageJ (NIH).

Example 1-7

Immunoprecipitation and Immunoblotting

Only live CTLs were harvested from CD99 WT or deficient T-cell lines activated for 4 days using Ficoll-Paque (GE healthcare), and cultured at 37° C. for 15 minutes with an anti-CD3 antibody (10 μg/ml) to induce activation. Thereafter, stimulation was stopped through washing with cold PBS, and the cells were harvested and lysed with a lysis buffer containing NP-40 (1%, Biosesang) at 4° C. for 20 minutes, after which 100 μg of the cell lysate was mixed with protein G-sepharose beads (35 μl, BioVision) and pre-cleaned at 4° C. for 1 hour. Subsequently, after treatment with an anti-α-tubulin antibody, mouse IgG isotype antibody, anti-CD99 antibody (EJ2), or rat IgG isotype antibody at 4° C., immunoprecipitation was performed using protein G-sepharose beads. The immunoprecipate was subjected to SDS-PAGE, transferred to a PVDF membrane, and stained with anti-β-actin (4C2, Sigma-Aldrich), anti-α-tubulin, an anti-CD99 antibody, and an anti-mouse IgG-HRP antibody, and luminescence was made to radiate therefrom using a West-Femto reagent (Thermo Fisher). The band of the corresponding protein was detected using an LAS-4000 mini (GE Healthcare).

Example 1-8

Preparation of Retroviral Vector for CAR Expression

CD19-targeting CD8 backbone CAR (h19BBz) ORF cDNA was prepared by requesting DNA synthesis of a previously published sequence (U.S. Patent Publication No. 2013/0287748 A) (Integrated DNA Technologies). CD19-targeting CD99 backbone CAR ORF cDNA (F58BBz, F45BBz, F35BBz, F35BBz-1) was prepared by extracting the sequences of the CD99 extracellular domain, transmembrane domain, and juxtamembrane domain from the human CD99 ORF sequence (NM_002414.4) of an NCBI database and linking such sequences with an anti-CD19 scFv (clone FMC63), a human 4-1BB intracellular signaling domain, and a human CD3 zeta chain intracellular signaling domain through DNA synthesis (Integrated DNA Technologies) and PCR. F8TJBBz was prepared by linking a CD19 scFv and a human CD8 extracellular domain with a human CD99 transmembrane domain, juxtamembrane domain, human 4-1BB intracellular signaling domain, and human CD3 zeta chain intracellular signaling domain through PCR. Each retroviral vector for CAR expression was prepared by cloning each CAR ORF cDNA into a HindIII/SalI restriction enzyme site after removal of the insert from the MSCV Hu Acceptor retroviral plasmid (Addgene #64269).

The sequence information of the domains used to prepare the CAR according to the present Example is as described in Tables 2 to 5, and the amino acid sequence and nucleic acid sequence of each CAR protein are as described in Table 6 and Table 8 below.

TABLE 8

Amino acid sequence and nucleic acid sequence of chimeric antigen receptor protein

| Classification | Sequence | SEQ ID NO: |
|---|---|---|
| h19BBz | MALPVTALLL PLALLLHAAR PDIQMTQTTS SLSASLGDRV TISCRASQDI SKYLNWYQQK PDGTVKLLIY HTSRLHSGVP SRFSGSGSGT DYSLTISNLE QEDIATYFCQ QGNTLPYTFG GGTKLEITGG GGSGGGGSGG GGSEVKLQES GPGLVAPSQS LSVTCTVSGV SLPDYGVSWI RQPPRKGLEW LGVIWGSETT YYNSALKSRL TIIKDNSKSQ VFLKMNSLQT DDTAIYYCAK HYYYGGSYAM DYWGQGTSVT VSSTTTPAPR PPTPAPTIAS QPLSLRPEAC RPAAGGAVHT RGLDFACDIY IWAPLAGTCG VLLLSLVITL YCKRGRKKLL YIFKQPFMRP VQTTQEEDGC SCRFPEEEEG GCELRVKFSR SADAPAYKQG QNQLYNELNL GRREEYDVLD KRRGRDPEMG GKPRRKNPQE GLYNELQKDK MAEAYSEIGM KGERRRGKGH DGLYQGLSTA TKDTYDALHM QALPPR | 41 |

TABLE 8-continued

Amino acid sequence and nucleic acid sequence of chimeric antigen receptor protein

| Classification | Sequence | SEQ ID NO: |
|---|---|---|
| | atggccttac cagtgaccgc cttgctcctg<br>ccgctggcct tgctgctcca cgccgccagg<br>ccggacatcc agatgacaca gactacatcc<br>tccctgtctg cctctctggg agacagagtc<br>accatcagtt gcagggcaag tcaggacatt<br>agtaaatatt taaattggta tcagcagaaa<br>ccagatggaa ctgttaaact cctgatctac<br>catacatcaa gattacactc aggagtccca<br>tcaaggttca gtggcagtgg gtctggaaca<br>gattattctc tcaccattag caacctggag<br>caagaagata ttgccactta cttttgccaa<br>cagggtaata cgcttccgta cacgttcgga<br>ggggggacca agctggagat cacaggtggc<br>ggtggctcgg gcggtggtgg gtcgggtggc<br>ggcggatctg aggtgaaact gcaggagtca<br>ggacctggcc tggtggcgcc ctcacagagc<br>ctgtccgtca catgcactgt ctcaggggtc<br>tcattacccg actatggtgt aagctggatt<br>cgccagcctc cacgaaaggg tctggagtgg<br>ctgggagtaa tatgggctag tgaaaccaca<br>tactataatt cagctctcaa atccagactg<br>accatcatca aggacaactc caagagccaa<br>gttttcttaa aaatgaacag tctgcaaact<br>gatgacacag ccatttacta ctgtgccaaa<br>cattattact acggtggtag ctatgctatg<br>gactactggg gccaaggaac ctcagtcacc<br>gtctcctcaa ccacgacgcc agcgccgcga<br>ccaccaacac cggcgcccac catcgcgtcg<br>cagcccctgt ccctgcgccc agaggcgtgc<br>cggccagcgg cggggggcgc agtgcacacg<br>agggggctgg acttcgcctg tgatatctac<br>atctgggcgc ccttggccgg gacttgtggg<br>gtccttctcc tgtcactggt tatcaccctt<br>tactgcaaac ggggcagaaa gaaactcctg<br>tatatattca acaaccatt tatgagacca<br>gtacaaacta ctcaagagga agatggctgt<br>agctgccgat ttccagaaga agaagaagga<br>ggatgtgaac tgagagtgaa gttcagcagg<br>agcgcagacg cccccgcgta caagcagggc<br>cagaaccagc tctataacga gctcaatcta<br>ggacgaagag aggagtacga tgttttggac<br>aagagacgtg gccgggaccc tgagatgggg<br>ggaaagccga aaggaagaa ccctcaggaa<br>ggcctgtaca tgaactgca gaaagataag<br>gaaagataag gattgggatg gattgggatg<br>aaaggcgagc gccggagggg caaggggcac<br>gatggccttt accagggtct cagtacagcc<br>accaaggaca cctacgacgc ccttcacatg<br>caggccctgc cccctcgcta a | 42 |
| F8TJBBz | MALPVTALLL PLALLLHAAR PDIQMTQTTS<br>SLSASLGDRV TISCRASQDI SKYLNWYQQK<br>PDGTVKLLIY HTSRLHSGVP SRFSGSGSGT<br>DYSLTISNLE QEDIATYFCQ QGNTLPYTFG<br>GGTKLEITGG GGSGGGGSGG GGSEVKLQES<br>GPGLVAPSQS LSVTCTVSGV SLPDYGVSWI<br>RQPPRKGLEW LGVIWGSETT YYNSALKSRL<br>TIIKDNSKSQ VFLKMNSLQT DDTAIYYCAK<br>HYYYGGSYAM DYWGQGTSVT VSSTTTPAPR<br>PPTPAPTIAS QPLSLRPEAC RPAAGGAVHT<br>RGLDADAPGV IPGIVGAVVV AVAGAISSFI<br>AYQKKKLCFK ENKRGRKKLL YIFKQPFMRP<br>VQTTQEEDGC SCRFPEEEEG GCELRVKFSR<br>SADAPAYKQG QNQLYNELNL GRREEYDVLD<br>KRRGRDPEMG GKPRRKNPQE GLYNELQKDK<br>MAEAYSEIGM KGERRRGKGH DGLYQGLSTA<br>TKDTYDALHM QALPPR | 43 |
| | atggccttac cagtgaccgc cttgctcctg<br>ccgctggcct tgctgctcca cgccgccagg<br>ccggacatcc agatgacaca gactacatcc<br>tccctgtctg cctctctggg agacagagtc<br>accatcagtt gcagggcaag tcaggacatt<br>agtaaatatt taaattggta tcagcagaaa | 44 |

TABLE 8-continued

Amino acid sequence and nucleic acid sequence of chimeric antigen receptor protein

| Classification | Sequence | SEQ ID NO: |
|---|---|---|
| | ccagatggaa ctgttaaact cctgatctac | |
| | catacatcaa gattacactc aggagtccca | |
| | tcaaggttca gtggcagtgg gtctggaaca | |
| | gattattctc tcaccattag caacctggag | |
| | caagaagata ttgccactta cttttgccaa | |
| | cagggtaata cgcttccgta cacgttcgga | |
| | gggggacca agctggagat cacaggtggc | |
| | ggtggctcgg gcggtggtgg gtcgggtggc | |
| | ggcggatctg aggtgaaact gcaggagtca | |
| | ggacctggcc tggtggcgcc ctcacagagc | |
| | ctgtccgtca catgcactgt ctcagggggtc | |
| | tcattacccg actatggtgt aagctggatt | |
| | cgccagcctc cacgaaaggg tctggagtgg | |
| | ctgggagtaa tatgggtag tgaaaccaca | |
| | tactataatt cagctctcaa atccagactg | |
| | accatcatca aggacaactc caagagccaa | |
| | gttttcttaa aaatgaacag tctgcaaact | |
| | gatgacacag ccatttacta ctgtgccaaa | |
| | cattattact acggtggtag ctatgctatg | |
| | gactactggg gccaaggaac ctcagtcacc | |
| | gtctcctcaa ccacgacgcc agcgccgcga | |
| | ccaccaacac cggcgcccac catcgcgtcg | |
| | cagcccctgt ccctgcgccc agaggcgtgc | |
| | cggccagcgg cggggggcgc agtgcacacg | |
| | aggggggctgg acgccgacgc cccaggcgtg | |
| | atccccggga ttgtggggc tgtcgtggtc | |
| | gccgtggctg gagccatctc tagcttcatt | |
| | gcttaccaga aaaagaagct atgcttcaaa | |
| | gaaaataaac ggggcagaaa gaaactcctg | |
| | tatatattca aacaaccatt tatgagacca | |
| | gtacaaacta ctcaagagga agatggctgt | |
| | agctgccgat ttccagaaga agaagaagga | |
| | ggatgtgaac tgagagtgaa gttcagcagg | |
| | agcgcagacg cccccgcgta caagcagggc | |
| | cagaaccagc tctataacga gctcaatcta | |
| | ggacgaagag aggagtacga tgttttggac | |
| | aagagacgtg gccgggaccc tgagatgggg | |
| | ggaaagccga gaaggaagaa ccctcaggaa | |
| | ggcctgtaca atgaactgca gaaagataag | |
| | atggcggagg cctacagtga gattgggatg | |
| | aaaggcgagc gccggagggg caaggggcac | |
| | gatggcctt accagggtct cagtacagcc | |
| | accaaggaca cctacgacgc ccttcacatg | |
| | caggccctgc ccctcgcta a | |

Example 1-9

Production of Retrovirus for CAR Expression

After transfection of each retroviral plasmid into the Phoenix ECO cell line (ATCC) using Lipofectamine 3000 (Invitrogen), the culture supernatant containing the ecotropic retrovirus secreted for 24-48 hours was added to a PG13 retroviral packaging cell line (ATCC), followed by spin infection (2500 rpm, 90 min). The culture supernatant of the PG13 retroviral packaging cell line thus prepared was harvested, filtered (0.45-μm filter) to remove remaining cell particles, concentrated 4-fold using a centrifugal filtration device (Millipore Amicon 100KD cut-off), and then used as a retroviral concentrate for CAR-T cell production.

Example 1-10

Preparation of CAR-T Cells

The leukocytes obtained from a normal person through leukapheresis were added along with an anti-CD28 antibody (CD28.2, 2 μg/ml, BD Biosciences) to a 24-well plate coated with an anti-CD3 antibody (OKT3, 10 μg/ml, BioXcell), followed by culture for 48 hours to activate T cells. The activated T cells were washed two times and then used for retroviral transduction. Coating overnight with RetroNectin (20 μg/ml, TaKaRa) at 4° C., addition of 2% BSA-DPBS to the washed 24-well plate, blocking at 37° C. for 30 minutes, and washing were performed, after which 1 ml of the retroviral concentrate was added thereto, and centrifugation was performed at 2000×g at 32° C. for 2 hours, so the retrovirus was attached to the bottom of the wells. After removing the viral concentrate and washing the wells, 1 ml of the activated T cells (1×10$^6$ cells/ml) was added to each well and centrifuged for 10 minutes (1000×g, 32° C.) to attach the cells to the retrovirus. Subsequently, the cells were cultured for 48 hours in the presence of human IL-2 (300 IU/ml, Proleukin, Novartis). The retrovirus-transduced T cells were washed two times, added with a fresh culture medium containing human IL-2 (200 IU/ml), proliferated for 3-6 days, and used as CAR-T cells. For the expression of CAR protein on the cell surface, the CAR-T cells proliferated for 3 days after retroviral transduction were stained with a CD19-Ck protein (a fusion protein of CD19 extracellular region and human immunoglobulin kappa chain constant region (Ck)) and APC-labeled anti-Ck antibody (anti-Ck-APC, BioLegend), and then expression was measured through flow cytometry (FACS-Calibur, BD Biosciences).

Example 1-11

Preparation of Luciferase-Expressing Raji Cells (Raji-Luc)

In order to artificially express luciferase in cells, a lentiviral vector capable of simultaneously expressing luciferase and GFP was prepared. Firefly luciferase ORF cDNA cleaved and extracted from a pGL3-basic plasmid (Promega) was cloned into the multi-cloning site of a bicistronic lentiviral vector (pLECE3) having both a multi-cloning site under the EF1α promoter and cloned GFP under the CMV promoter (Lee S. H. et al., PLoS One. 2020; 15(1): e0223814) to prepare a pLECE3-Luc vector. The pLECE3-Luc plasmid was transfected along with three types of lentiviral packaging plasmids (pMDLg/pRRE, pRSVrev, pMD.G) into a lentiviral packaging cell line (293FT cell, Invitrogen) using a Lipofectamine 2000 reagent. After 24-48 hours, the culture supernatant containing the secreted lentivirus was harvested and concentrated 10-fold using a centrifugal filtration device. The lentiviral concentrate was added to Raji cells and transduced through centrifugation at 2500 rpm at room temperature for 90 minutes in the presence of polybrene (6 μg/ml, Sigma-Aldrich). Among the transduced Raji cells, GFP-positive cells were separated and purified using a flow cytometer (FACS-Aria II, BD Biosciences) and used as Raji-Luc cells.

Example 1-12

Measurement of Ability of CAR-T Cells to Kill Tumors and Activation Thereof

CAR-T cells ($1.2 \times 10^3$ to $7.5 \times 10^5$ cells/100 μl/well) proliferated for 3 days after retroviral transduction were mixed with Raji-Luc cells ($3 \times 10^4$ cells/50 μl/well) at various ratios (0.04-25:1), co-cultured overnight in a 96-well plate, added with 50 μl of D-luciferin (600 μg/ml, Promega), and cultured at 37° C. for 10 minutes, thus inducing luciferase enzyme activity in the surviving Raji-Luc cells. The luminescence of these cells was measured using a luminometer (Tecan) and compared with the luminescence of Raji-Luc cells not treated with CAR-T cells to calculate the survival rate of tumor cells, thereby determining the ability of CAR-T cells to kill tumors.

In order to measure the extent of activation of CAR-T cells, CAR-T cells and Raji cells were mixed in equal numbers ($3 \times 10^4$ cells) and co-cultured in a 96-well plate for 24 hours, after which the culture supernatant was harvested. The amount of IFN-γ secreted into the supernatant was measured through ELISA (human IFN-γ ELISA kit, BD Biosciences).

Example 1-13

Evaluation of In-Vivo Efficacy of CAR-T Cells 7 days after intravenous injection of Raji-Luc cells ($5 \times 10^5$ cells per mouse) into immunodeficient NSG mice, CAR-T cells ($5 \times 10^6$ cells per mouse) proliferated for 8 days after retroviral transduction were intravenously injected thereto. Then, after periodic intraperitoneal injection of D-luciferin (2 mg per mouse, Promega), changes in tumor burden were observed by measuring in-vivo luminescence using a bioluminescence imaging machine (IVIS, Perkin Elmer).

Example 1-14

Evaluation of Ability of CAR-T Cells to Form Immune Synapses with Raji Cells

In order to observe the formation of immune synapses between CAR-T cells and tumor cells (Raji), CAR-T cells ($2 \times 10^5$ cells/200 μl) and Raji cells ($1 \times 10^5$ cells/200 μl) stained with CMTMR (10 μM, Invitrogen) at 37° C. for 30 minutes were co-cultured on a poly-L-lysine-coated coverslip and fixed at 15 minutes, 30 minutes, 1 hour, or 3 hours. After F-actin staining in the same manner as for confocal microscopy described above, images were taken with a FlowView3000 confocal microscope (Olympus) and analyzed using ImageJ (NIH).

Example 2

Figure 1:
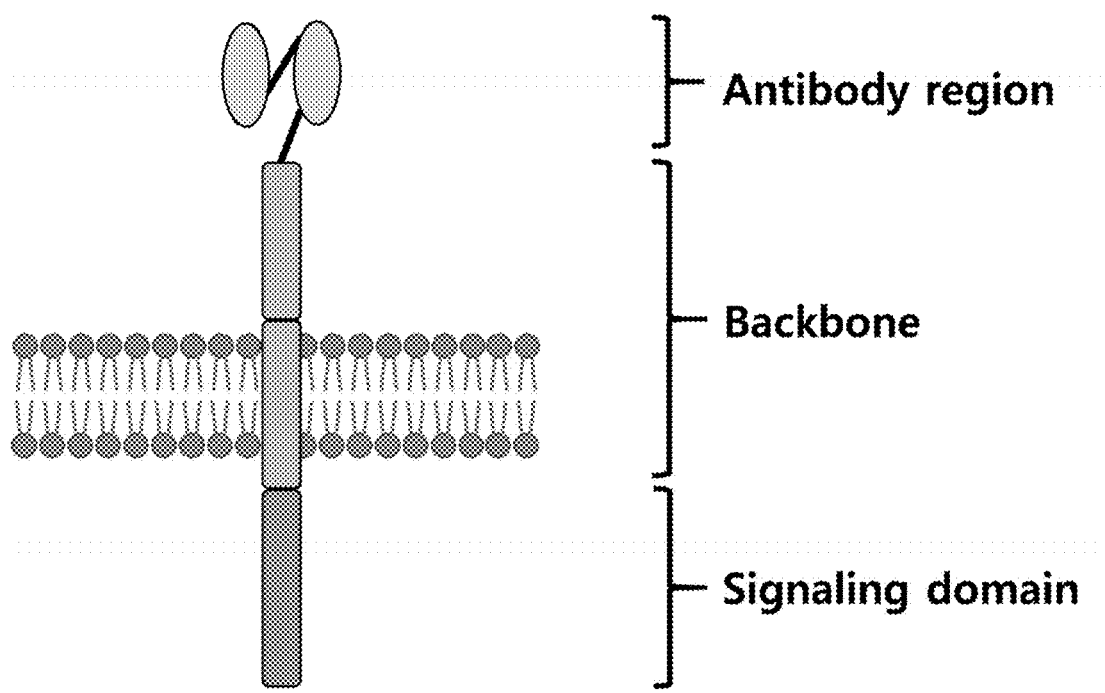
FIG. 1 schematically shows a chimeric antigen receptor (CAR).
Figure 2:
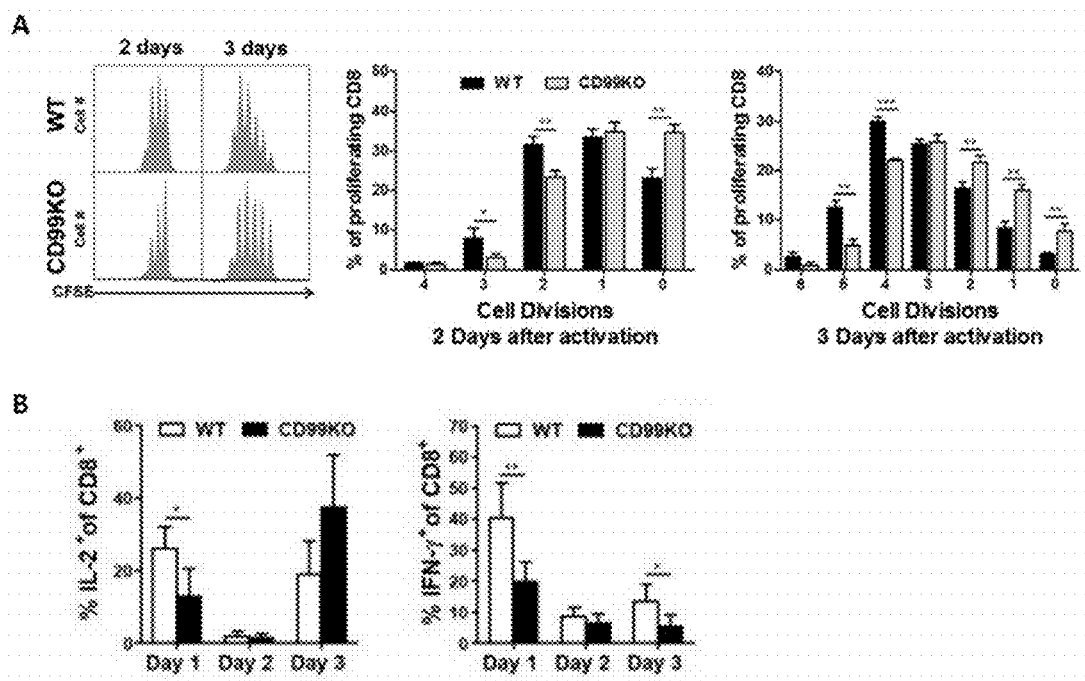
FIG. 2 shows the impairment of activation of CD99-deficient T cells caused by TCR stimulation, particularly the results of analysis of TCR-stimulated division ability of CD8 T cells isolated from wild-type mouse (WT) and CD99 knockout mouse (CD99 KO) lymph nodes and labeled with CFSE, and of cytokine secretion ability thereof.

Confirmation of Impairment of T-Cell Immune Synapse Formation Due to CD99 Deficiency Based on previous studies in which CD99 stimulation in T cells increases T-cell activation and CD99 is present in lipid raft fractions including actin cytoskeletons (Wingett D. et al., Cell Immunol. 1999; 193(1): 17-23), in order to verify the role of CD99 in the formation of immune synapses, the processes of activation and immune synapse formation of CD99-deficient T cells due to TCR stimulation were analyzed. With regard to analysis of cell division induced by anti-CD3/CD28 antibody stimulation of T cells isolated from CD99 knockout mice, it was observed that initial cell division was significantly delayed compared to wild-type CD8 T cells and also that the initial ability of CD99-deficient T cells to produce cytokine was decreased compared to wild-type T cells. Therefore, it was confirmed that CD99 was involved in the process of activation of T cells through TCR stimulation (FIGS. 2A and 2B).

Figure 3:
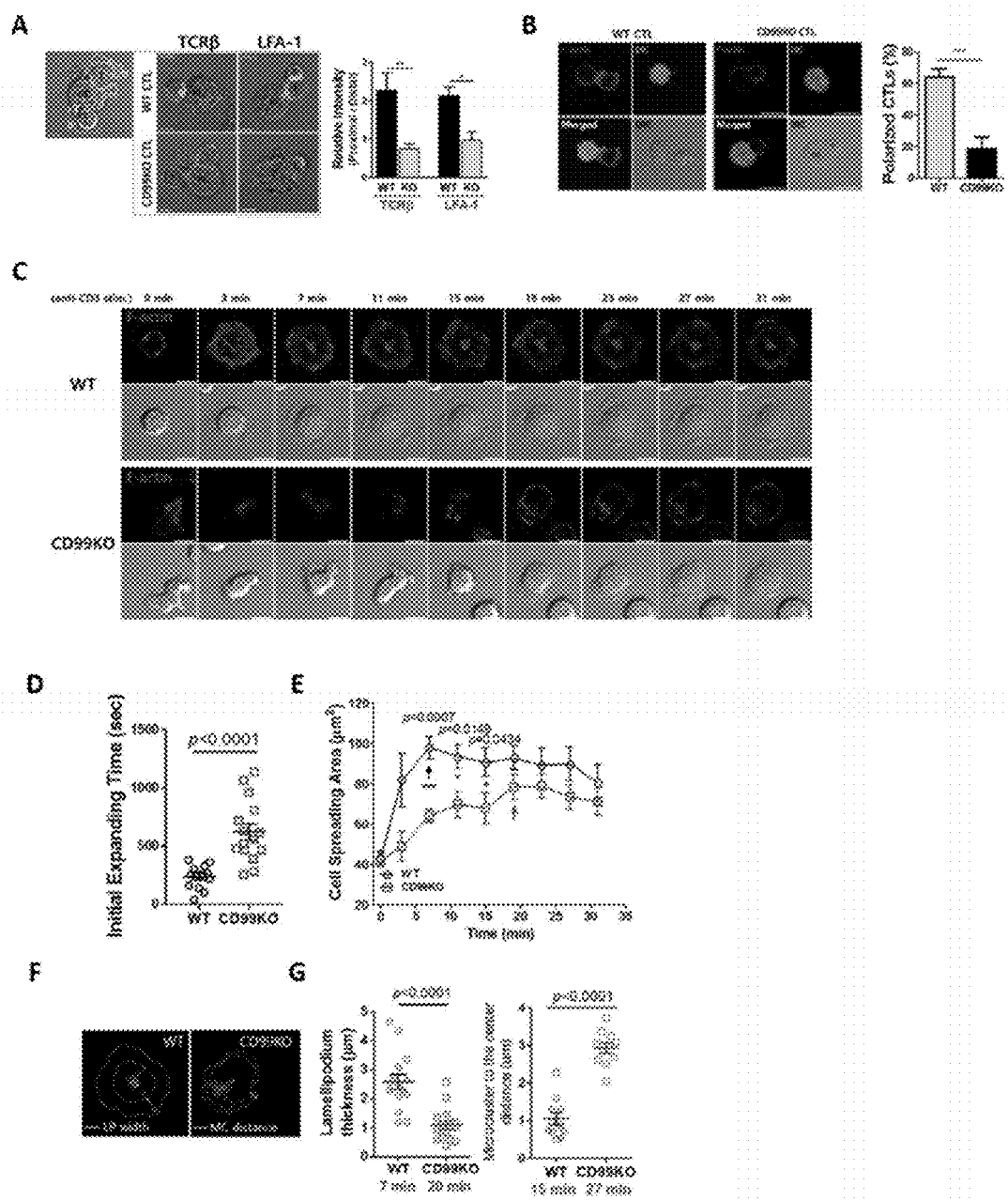
FIG. 3 shows the immune synapse impairment of CD99-deficient T cells.

As for the specific mechanism thereof, based on the results of observation of the process of forming immune synapses through co-culture of T cells and antigen-presenting cells, it was confirmed that the clustering of TCR and LFA-1 constituting immune synapses to the antigen-presenting cell contact region was significantly reduced in CD99-deficient T cells compared to wild-type T cells (FIG. 3A). Also, it was observed that the synapse clustering of actin, which provides the cytoskeleton for immune synapse formation, was significantly reduced due to CD99 deficiency (FIG. 3B). In order to observe the rearrangement of actin cytoskeletons in the immune synapses in more detail, in an experimental system in which a slide surface coated with an anti-CD3 antibody was assumed to be the surface of antigen-presenting cells and also in which the slide contact region of T cells was assumed to be an immune synapse, when actin rearrangement was observed depending on the time of T-cell contact with the slide surface using real-time confocal microscopy, it was confirmed that CD99 deficiency delayed the formation of the T-cell contact surface through actin polymerization and also that the area of the T-cell contact surface was also greatly reduced (FIGS. 3C-3E). Moreover, in CD99-deficient T cells, the thickness of the lamellipodia related to cell spreading was greatly reduced, and structural abnormality of the immune synapses was also observed, such as the actin microcluster being located in the peripheral portion of the immune synapse rather than in the proximal portion thereof (FIGS. 3F and 3G), indicating that CD99 plays a key role in the formation of immune synapses.

Example 3

Figure 4:
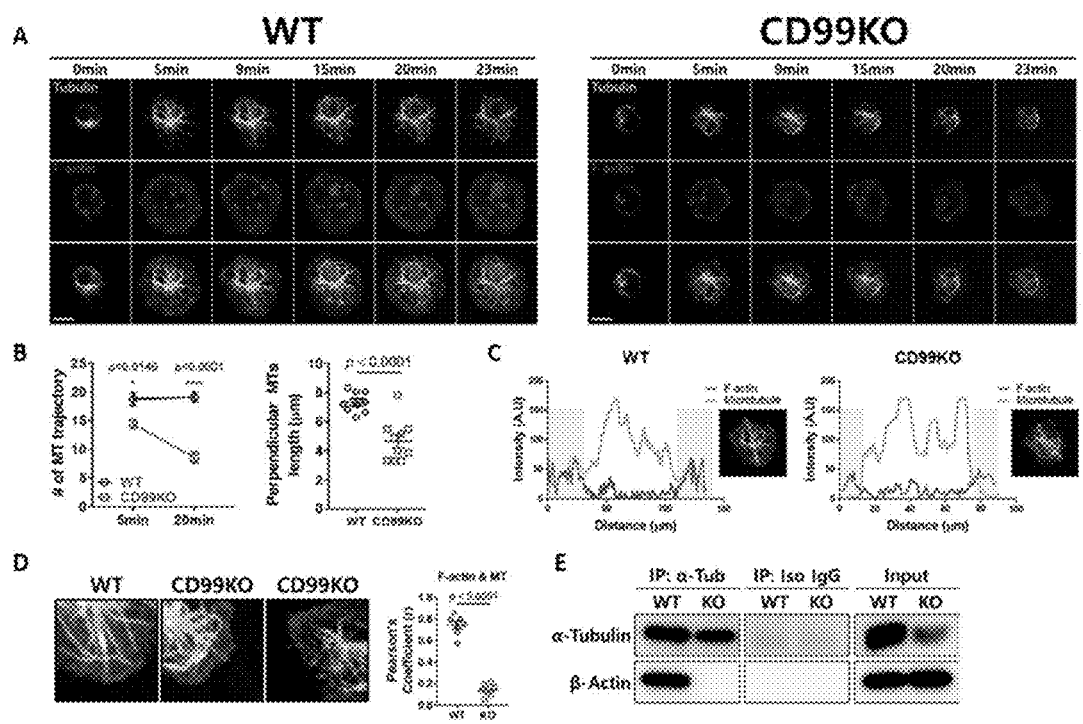
FIG. 4 shows the impairment of actin and microtubule network formation in CD99-deficient T-cell immune synapses.

Confirmation of Impairment of Actin-Microtubule Interaction Due to CD99 Deficiency Although the importance of formation of microtubule networks along with actin cytoskeletal rearrangement in the formation of immune synapses has recently begun to be spotlighted, not much is known about the actin-microtubule interaction. Accordingly, as a result of tracking the formation of microtubule networks in T-cell immune synapses in the case of CD99 deficiency, instability of formation of microtubule networks was observed. Specifically, upon T-cell activation, microtubules are newly generated from the microtubule-organizing center (MTOC), and the growing microtubules radially extend toward the cell membrane, but in the case of CD99 deficiency, it was observed that the formation of radial microtubules was not efficient, and was rapidly reduced (FIGS. 4A and 4B). Furthermore, the shift of the MTOC to the center of the immune synapse observed during T-cell activation was not observed in CD99-deficient T cells. In particular, some microtubules extend perpendicularly into the actin-rich lamellipodia and are fixed to the cell membrane through interaction with actin present in the cell membrane, but CD99 deficiency greatly decreases the number of microtubules entering lamellipodia, indicative of the likelihood of inhibition of actin-microtubule interaction (FIGS. 4C and 4D). As evidence therefor, actin and tubulin co-immunoprecipitated and interacted in the cell lysate of wild-type cells, whereas co-immunoprecipitation thereof was not observed in CD99-deficient cells (FIG. 4E), indicating that CD99 contributes to the physical actin-microtubule interaction.

Example 4

Analysis of Interaction of CD99 with Actin and Microtubules

Figure 5:
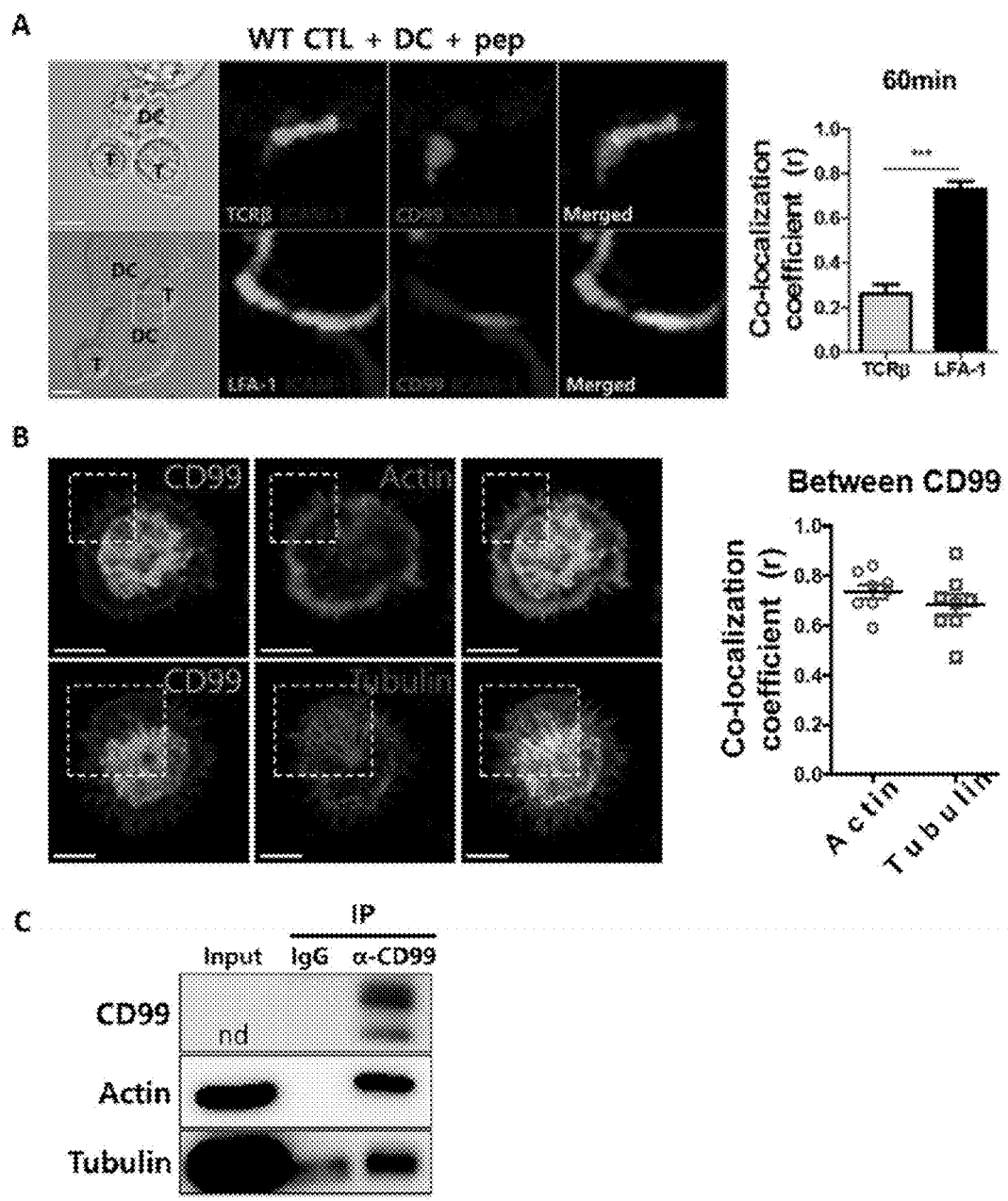
FIG. 5 shows the results of analysis of the correlation between the location of CD99 in the immune synapse cell membrane and the distribution of actin and microtubules in the cytoplasm in wild-type cells.

Based on the above results, in order to confirm whether CD99 is located at the immune synapse and mediates actin-microtubule interaction, the presence of CD99 at the immune synapse was observed using a confocal microscope. Thereby, CD99 was observed to migrate to the immune synapse site upon T-cell activation, and in particular, co-localization with LFA-1 distributed in the actin-rich area was observed (FIG. 5A). In the positional relationship with the cytoskeleton, a site in which CD99 was co-localized with each of actin and microtubules was observed (FIG. 5B). Moreover, CD99 was confirmed to co-immunoprecipitate with both actin and tubulin in the activated T-cell lysate (FIG. 5C). Therefore, it was construed that CD99 is a membrane protein that functions as a bridge molecule mediating the actin-microtubule interaction, which has not been found for a long time.

Example 5

Figure 6:
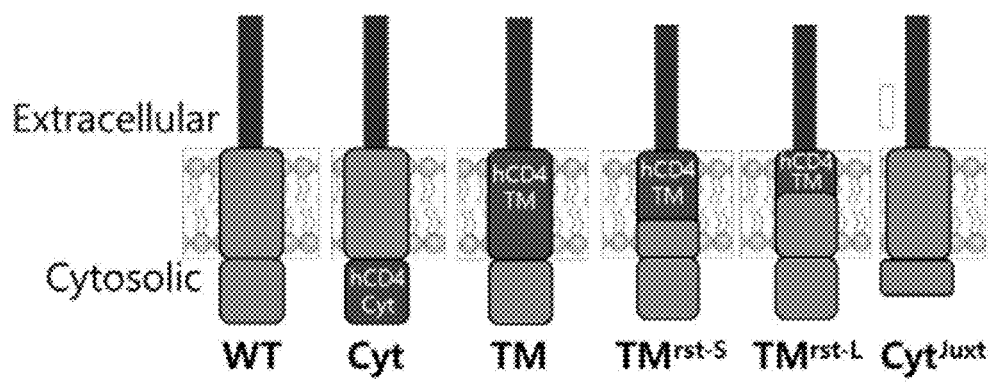
FIG. 6 shows results confirming the interaction sites of the CD99 protein with actin and microtubules.
Figure 6:
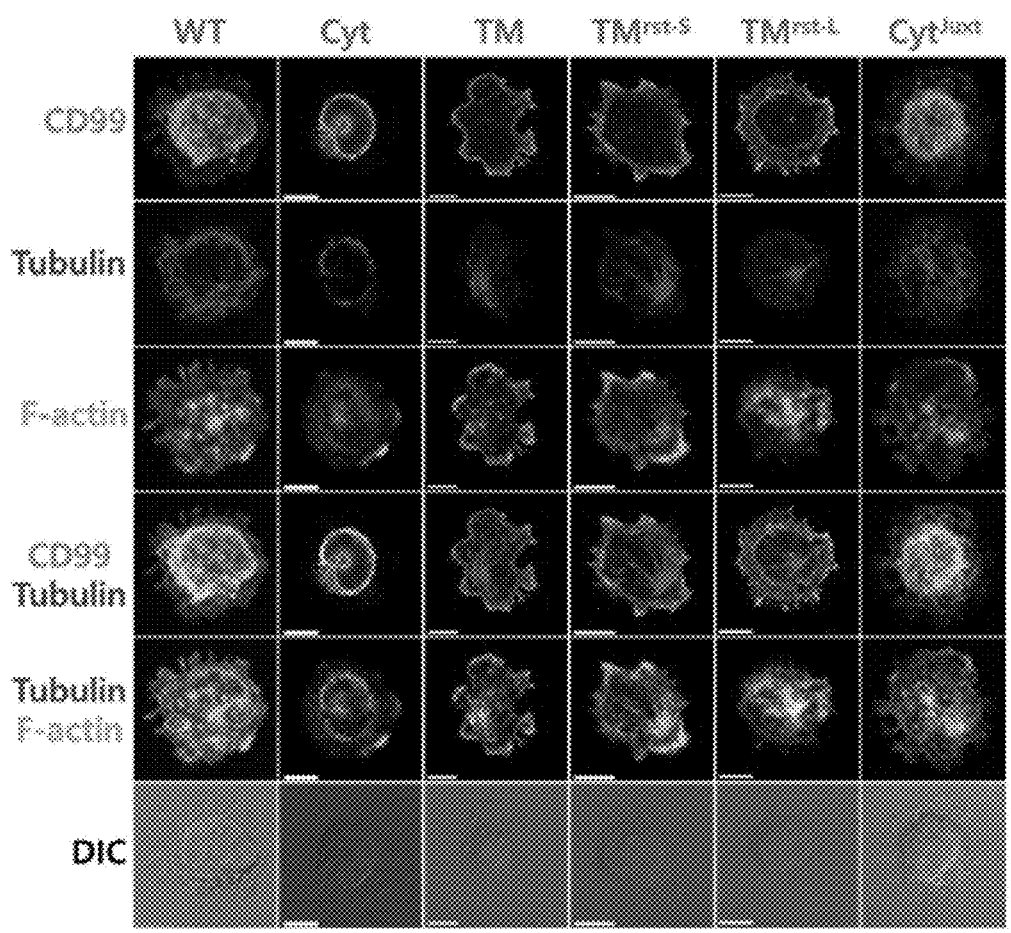

Function of CD99 Transmembrane Domain and Cytoplasmic Domain in the Interaction of CD99 with Actin and Microtubules In order to identify the binding site of CD99 to actin and microtubules, mutant proteins in which the transmembrane domain or cytoplasmic domain of CD99 was substituted with the corresponding site of CD4, which is an unrelated protein, were designed, after which these proteins were expressed in CD99-deficient T cells. The protein in which the CD99 transmembrane domain was substituted with the corresponding site of CD4 was called a "CD99 TM mutant", and the protein in which the CD99 cytoplasmic domain was substituted with the cytoplasmic domain of CD4 was called a "CD99 Cyt mutant" (FIG. 6A). Upon observation of co-localization of each mutant protein with actin and microtubules through confocal microscopy, the CD99 Cyt mutant was co-localized with microtubules, but was not accompanied by microtubule growth into the expanding lamellipodia and was not fixed to the plasma membrane, and also, co-localization thereof with actin did not occur, indicating that such phenomena were caused by the loss of the interaction between CD99 Cyt mutant and actin. On the other hand, the CD99 TM mutant maintained co-localization with actin, but the tension and stability of the grown and extended microtubules were deteriorated, lamellipodia retraction and catastrophe were not induced, and the co-localization between the C99 TM mutant and the microtubules was lost (FIG. 6B). Accordingly, it was proven that the cytoplasmic domain of CD99 is essential for interaction with actin and promotes co-growth of actin and microtubules, and also that the transmembrane domain is essential for interaction with microtubules and promotes co-contraction of actin and microtubules. In order to confirm whether a specific subregion of the CD99 transmembrane domain is critical for binding to microtubules, a mutant in which a portion of the CD99 transmembrane domain was introduced again into the CD4 transmembrane domain of the TM mutant was prepared and tested, and thereby, it was confirmed that the entire CD99 transmembrane domain is essential for binding to microtubules. For the CD99 cytoplasmic domain, a mutant in which the membrane distal region was removed from the cell membrane region and the juxtamembrane region was maintained, prepared and tested, and thereby, it was observed that the interaction with actin and microtubules was maintained, like the wild-type CD99 protein, indicating that the juxtamembrane region was crucial for the interaction with actin (FIGS. 6A and 6B). In conclusion, CD99 was important for the co-contraction of actin and microtubules using the transmembrane domain and acted on the co-growth of actin and microtubules using the intracellular juxtamembrane region, and thus mediated overall actin-microtubule interaction and contributed to dynamic instability.

Example 6

Preparation of CAR-T Cells Transfected with CD99

Recently, CAR-T cell therapies have been receiving attention due to high therapeutic efficacy (complete remission rate of 70-80%) for CD19-positive acute leukemia, but it is known that the therapeutic efficiency thereof on CD19-positive lymphoma growing as a solid tumor is low (complete remission rate of about 50%). Therefore, the efficacy of CAR-T cells on solid tumors, including CD19-positive lymphoma, needs to be greatly improved.

T-cell activation of the currently available CAR protein mainly relies on activation of the intracellular signaling domain, and the CD8 extracellular and transmembrane domains, which are the backbone connecting the antibody region to the intracellular signaling domain, are responsible only for a physical connection function. According to Examples 2 to 5, it was demonstrated that the cell membrane and the intracellular juxtamembrane region of CD99 contribute to the stabilization of immune synapse formation by mediating the actin-microtubule interaction. Therefore, when the cell membrane and the juxtamembrane region of CD99 are introduced into the conventional CAR protein design, manufacture of improved CAR-T cells having an additional function of immune synapse stabilization, in addition to the conventional signaling function, can be expected.

In this Example, for the CAR protein targeting the CD19 antigen, several CAR proteins using the extracellular domain, transmembrane domain, and juxtamembrane region of CD99 were designed, and CAR-T cells expressing such new CAR proteins were prepared. In particular, as the extracellular domain of the CAR protein, CD99 extracellular domains (F58BBz, F45BBz, F35BBz, F35BBz-1) having various lengths (58, 45, and 35 amino acid residues) or a CAR protein (F8TJBBz) using the CD8 extracellular domain of the conventional CAR protein were designed (Tables 6 and 8, FIG. 7A). Thereafter, a retrovirus for gene expression of such a protein was prepared and transduced into human T cells to prepare CAR-T cells.

Based on the results of analysis of the phenotype and in vitro function of the CAR-T cells thus prepared, it was confirmed through flow cytometry that each CAR protein was expressed on the surface of T cells (FIG. 7B). In such CD99-backbone-based CAR-T cells, transduction efficiency, measured as a percentage of CAR-positive cells, and the amount of CAR expressed per cell, measured as mean fluorescent intensity (MFI), were low compared to conventional CD8-backbone-based CAR-T cells (h19BBz) (FIG. 7B), but in the cell-killing ability test on CD19-positive lymphoma cells (Raji cells), the killing ability of CD99-backbone-based CAR-T cells was comparable to that of conventional CAR-T cells (FIG. 7C). In the subsequent experiment on the cytokine secretion of T cells, all CD99-backbone-based CAR-T cells, except for F8TJBBz CAR-T cells, exhibited similar or improved IFN-γ secretion compared to conventional CAR-T cells (FIG. 7D). In particular, F35BBz CAR-T cells having the shortest extracellular domain length exhibited very high ability to produce IFN-γ compared to conventional CAR-T cells. Therefore, it was confirmed that CD99-backbone-based CAR-T cells have tumor-killing ability and activation functionality comparable to those of conventional CAR-T cells, despite the low CAR expression rate thereof. However, F8TJBBz CAR-T cells were excluded from subsequent experiments because of the very low CAR expression and cytokine secretion.

Example 7

Confirmation of Improvement in Anticancer Efficacy of CD99-Backbone-Based CAR-T Cells In Vivo In order to confirm the in vivo anticancer efficacy of the CD99-backbone-based CAR-T cells of Example 6, after administration of CAR-T cells to immunodeficient mice (NSG mice) inoculated with lymphoma cells, the in vivo proliferation of tumors and the rate of survival of mice were measured. In order to efficiently track in vivo proliferation of tumors, human lymphoma cells having artificially expressed luciferase (Raji-Luc cells) were injected intravenously, and bioluminescence imaging (BLI) was used to measure the extent of luminescence, so the intensity of luminescence radiated from the tumor cell populations was periodically measured.

When CAR-T cells were injected for therapeutic purposes 7 days after tumor inoculation, it was observed that conventional h19BBz CAR-T cells significantly inhibited tumor growth. However, regrowth of tumors over time was observed in the group administered with the conventional CAR-T cells, and eventually all subjects died, indicating limited therapeutic efficacy. However, in the groups administered with CD99-backbone-based CAR-T cells, the regrowth of tumors was significantly delayed, and particularly, in the group administered with F35BBz CAR-T cells, all tumor cells were removed, and no tumor recurrence was observed (FIGS. 8A and 8B). All subjects died within 90 days of tumor inoculation in the group administered with the conventional h19BBz CAR-T cells, but the mice administered with F35BBz CAR-T cells and F45BBz CAR-T cells did not show any death until 140 days after tumor inoculation, and in the group administered with F35BBz CAR-T cells, all subjects survived until the $153^{rd}$ day, at which the experiment was terminated (FIG. 8C). Therefore, it was confirmed that CD99-backbone-based CAR-T cells, particularly F35BBz CAR-T cells, exhibited significantly improved therapeutic efficacy compared to conventional CAR-T cells.

Example 8

Improvement in Ability of CAR-T Cells Introduced with CD99 to Form Immune Synapse In order to test the possibility that the in vivo antitumor effect of F35BBz CAR-T cells observed above was due to the effect of enhancing immune synapses through the CD99 backbone, CAR-T cells were co-cultured with tumor cells (Raji cells), and the ability thereof to form immune synapses was compared with that of h19BBz CAR-T cells. Thereby, the ratio of tumor cells forming immune synapses with CAR-T cells was significantly increased in the group administered with F35BBz CAR-T cells compared to the group administered with h19BBz CAR-T cells having a CD8 backbone (FIGS. 9A and 9B). Unusually, for the F35BBz T cells, the number of CAR-T cells bound per tumor cell was much higher than that of the h19BBz CAR-T cells (FIGS. 9C and 9D). Thus, it was verified that F35BBz CAR-T cells were capable of forming greatly enhanced immune synapses with tumor cells. Therefore, the effect of the transmembrane domain and juxtamembrane region of CD99 on mediating the formation of immune synapses was reproduced in CAR-T cells, strongly suggesting that the increased potency of CD99-backbone-based CAR-T cells is an effect resulting from immune synapse stabilization.

INDUSTRIAL APPLICABILITY

According to the present invention, the immune synapse stabilization function of CD99 among conventional T-cell surface proteins is confirmed, and a novel chimeric antigen receptor comprising the transmembrane domain of CD99 as a backbone is prepared. Such CD99-based CAR-T cells are capable of forming very stable immune synapses with tumor cells compared to conventional backbone-based CAR-T cells, and can exhibit improved tumor therapeutic efficiency, making them useful for immune cell therapy for the treatment of cancer.

Although specific configurations of the present invention have been disclosed in detail, it will be obvious to those skilled in the art that the description is merely of preferable exemplary embodiments and is not to be construed as limiting the scope of the present invention. Therefore, the substantial scope of the present invention is defined by the accompanying claims and equivalents thereto.

SEQUENCE LISTING FREE TEXT

An electronic file is attached.

The invention claimed is:

1. A chimeric antigen receptor (CAR) comprising:
  (a) an antigen-binding domain;
  (b) a backbone comprising an extracellular spacer domain and a transmembrane domain; and
  (c) an intracellular signaling domain,
  wherein the transmembrane domain comprises a CD99 transmembrane domain, and wherein the chimeric antigen receptor comprises a CD99 intracellular juxtamembrane domain.

2. The chimeric antigen receptor according to claim 1, wherein the CD99 transmembrane domain comprises an amino acid sequence represented by SEQ ID NO: 3.

3. The chimeric antigen receptor according to claim 1, wherein the extracellular spacer domain comprises a CD99 extracellular domain.

4. The chimeric antigen receptor according to claim 3, wherein the CD99 extracellular domain is represented by an amino acid sequence of SEQ ID NO: 5 or an amino acid sequence comprising contiguous 20 to 70 amino acid residues in the amino acid sequence of SEQ ID NO: 5.

5. The chimeric antigen receptor according to claim 3, wherein the CD99 extracellular domain comprises an amino acid sequence represented by SEQ ID NO: 5, 7, 9, or 11.

6. The chimeric antigen receptor according to claim 1, wherein the CD99 intracellular juxtamembrane domain comprises an amino add sequence represented by SEQ ID NO: 13.

7. The chimeric antigen receptor according to claim 1, wherein the intracellular signaling domain comprises:

an intracellular signaling domain selected from the group consisting of CD3 Zeta (ζ), CD3 gamma (γ), CD3 delta (δ), CD3 epsilon (ε), FcR gamma, FcR beta, CD5, CD22, CD79a, CD79b, and CD66d; and/or
a co-stimulatory domain selected from the group consisting of CD2, CD7, CD27, CD28, CD30, CD40, 4-1 BB (CD137), OX40 (CD134), ICOS, LFA-1, GITR, MyD88, DAP1, PD-1, LIGHT, NKG2C, B7-H3, and a ligand specifically binding to CD83.

8. The chimeric antigen receptor according to claim 7, wherein the CD3 Zeta (ζ) intracellular signaling domain comprises an amino acid sequence of SEQ ID NO: 17 or 19.

9. The chimeric antigen receptor according to claim 1, wherein the antigen-binding domain comprises an antibody or antigen-binding fragment thereof that specifically binds to an antigen selected from the group consisting of:
  4-18B, BCMA, BAFF, B7-H3, B7-H6, CA9, CTAG1B, CEA, cyclin, cyclin A2, cyclin B1, CCL-1, CCR4, CD3, CD4, CD19, CD20, CD22, CD23, CD24, CD30, CD33, CD38, CD40, CD44, CD44v6, CD44v7/8, CD52, CD58, CD62, CD79A, CD79B, CD80, CD123, CD133, CD138, CD171, CSPG4, CLDN18, CLDN6, CTLA-4, c-Met, DLL3, EGFR, tEGFR, EGFRvIII, EPG-2, EPG-40, ephrin B2, EPHA2, estrogen receptor, Fc receptor, FCRL5, FGF23, FBP, FOLR1, FOLR2, GD2, ganglioside GD3, gp100, GPC3, GPCR5D, GM-CSF, Her2/neu, Hera, Her4, erbB dimer, HMW-MAA, HBsAg, HLA-A1, HLA-A2, IL-22Ra, IL-13Ra2, ICOS, IGF-1 receptor, integrin αvβ6, interferon receptor, IFNγ, IL-2R, IL-4R, IL-5R, IL-6R, IL-17RA, IL-31IR, IL-36R, kdr, L1-CAM, CE7 epitope of L1-CAM, LRRC8A, Lewis Y, LAG3, MAGEA1, MAGEA3, MAGEA6, MAGEA10, MSLN, CMV, MUC1, NKG2D ligand, MART-I, NGF, NCAM, NRP-1, NRP-2, carcinoembryonic antigen, PD-L1, PRAME, progesterone receptor, prostate-specific antigen, PSCA, PSMA, RANKL, ROR1, SLAMF7, survivin, TPBG, TAG72, TRP1, TRP2, and Wilms' tumor 1 (WT1).

10. The chimeric antigen receptor according to claim 9, wherein the antigen-binding fragment is a single-chain variable fragment (scFv) or nanobody of an antibody.

11. The chimeric antigen receptor according to claim 1, further comprising a signal peptide at an N-terminus of the antigen-binding domain.

12. The chimeric antigen receptor according to claim 11, wherein the signal peptide is a CD8α signal peptide comprising an amino acid sequence of SEQ ID NO: 25.

13. The chimeric antigen receptor according to claim 1, wherein the chimeric antigen receptor comprises an amino acid sequence represented by SEQ ID NO: 27, 29, 31, or 33.

14. A nucleic acid encoding the chimeric antigen receptor according to claim 1.

15. An expression vector comprising the nucleic acid according to claim 14.

16. A virus comprising the expression vector according to claim 15.

17. An immune cell expressing the chimeric antigen receptor according to claim 1 on a surface thereof.

18. The immune cell according to claim 17, wherein the immune cell is a T cell, NK cell, NKT cell, or macrophage.

19. A composition for treating cancer comprising the immune cell according to claim 18.

* * * * *